US012029921B2

(12) United States Patent
Laurence, Jr. et al.

(10) Patent No.: US 12,029,921 B2
(45) Date of Patent: Jul. 9, 2024

(54) SYSTEMS AND METHODS FOR PATIENT MONITORING FOR RADIOTHERAPY

(71) Applicant: RefleXion Medical, Inc., Hayward, CA (US)

(72) Inventors: Thomas Leroy Laurence, Jr., Benicia, CA (US); Jayakrishnan Janardhanan, Union City, CA (US)

(73) Assignee: RefleXion Medical, Inc., Hayward, CA (US)

( * ) Notice: Subject to any disclaimer, the term of this patent is extended or adjusted under 35 U.S.C. 154(b) by 0 days.

(21) Appl. No.: 17/852,067

(22) Filed: Jun. 28, 2022

(65) Prior Publication Data

US 2022/0395707 A1    Dec. 15, 2022

Related U.S. Application Data

(63) Continuation of application No. 16/191,131, filed on Nov. 14, 2018, now Pat. No. 11,369,806.
(Continued)

(51) Int. Cl.
*A61N 5/00* (2006.01)
*A61B 34/10* (2016.01)
(Continued)

(52) U.S. Cl.
CPC .......... *A61N 5/1049* (2013.01); *A61B 34/10* (2016.02); *A61N 5/1081* (2013.01);
(Continued)

(58) Field of Classification Search
CPC .... A61N 5/1049; A61N 5/1081; A61N 5/107; A61N 2005/105; A61N 2005/1059;
(Continued)

(56) References Cited

U.S. PATENT DOCUMENTS 3,418,475 A   12/1968   Hudgens
3,668,399 A   6/1972    Cahill et al.
(Continued)

FOREIGN PATENT DOCUMENTS

CN   1681436 A   10/2005
CN   1799509 A   7/2006
(Continued)

OTHER PUBLICATIONS

Black, Q.C. et al. (2004). "Defining a Radiotherapy Target with positron emission tomography," Int. J. Radiation Oncology Biol. Phys. 60:1272-1282.
(Continued)

*Primary Examiner* — Shahdeep Mohammed
*Assistant Examiner* — Adam D. Kolkin
(74) *Attorney, Agent, or Firm* — Cooley LLP

(57) ABSTRACT

Disclosed herein are systems and methods for real-time monitoring of patient position and/or location during a radiation treatment session. Images acquired of a patient during a treatment session can be used to calculate the patient's position and/or location with respect to the components of the radiation therapy system. One variation of a radiation therapy system includes a circular gantry with a rotatable ring coupled to a stationary frame, a therapeutic radiation source mounted on the rotatable ring, and a patient-monitoring imaging system mounted on the rotatable ring. The patient-monitoring system may have one or more image sensors or cameras disposed on the rotatable ring within a bore region of the radiation therapy system, and may be configured to acquire image data as the ring rotates.

40 Claims, 15 Drawing Sheets

Related U.S. Application Data

(60) Provisional application No. 62/585,772, filed on Nov. 14, 2017.

(51) Int. Cl.
 *A61N 5/10* (2006.01)
 *A61B 90/00* (2016.01)

(52) U.S. Cl.
 CPC ... *A61B 2034/105* (2016.02); *A61B 2090/367* (2016.02); *A61B 2090/373* (2016.02); *A61N 2005/105* (2013.01); *A61N 2005/1059* (2013.01); *A61N 5/107* (2013.01); *A61N 2005/1074* (2013.01); *A61N 2005/1076* (2013.01)

(58) Field of Classification Search
 CPC .... A61N 2005/1074; A61N 2005/1076; A61B 34/10; A61B 2034/105; A61B 2090/367; A61B 2090/373
 See application file for complete search history.

(56) References Cited

U.S. PATENT DOCUMENTS

| | | | |
|---|---|---|---|
| 3,767,883 | A | 10/1973 | Staats |
| 3,794,840 | A | 2/1974 | Scott |
| 3,869,615 | A | 3/1975 | Hoover et al. |
| 3,906,233 | A | 9/1975 | Vogel |
| 4,361,902 | A | 11/1982 | Brandt et al. |
| 4,389,569 | A | 6/1983 | Hattori et al. |
| 4,503,331 | A | 3/1985 | Kovacs, Jr. et al. |
| 4,529,882 | A | 7/1985 | Lee |
| 4,563,582 | A | 1/1986 | Mullani |
| 4,575,868 | A | 3/1986 | Ueda et al. |
| 4,628,499 | A | 12/1986 | Hammett |
| 4,642,464 | A | 2/1987 | Mullani |
| 4,647,779 | A | 3/1987 | Wong |
| 4,677,299 | A | 6/1987 | Wong |
| 4,771,785 | A | 9/1988 | Duer |
| 4,868,844 | A | 9/1989 | Nunan |
| 5,075,554 | A | 12/1991 | Yunker et al. |
| 5,099,505 | A | 3/1992 | Seppi et al. |
| 5,117,445 | A | 5/1992 | Seppi et al. |
| 5,168,532 | A | 12/1992 | Seppi et al. |
| 5,206,512 | A | 4/1993 | Iwao |
| 5,207,223 | A | 5/1993 | Adler |
| 5,272,344 | A | 12/1993 | Williams |
| 5,317,616 | A | 5/1994 | Swerdloff et al. |
| 5,329,567 | A | 7/1994 | Ikebe |
| 5,351,280 | A | 9/1994 | Swerdloff et al. |
| 5,390,225 | A | 2/1995 | Hawman |
| 5,394,452 | A | 2/1995 | Swerdloff et al. |
| 5,396,534 | A | 3/1995 | Thomas |
| 5,418,827 | A | 5/1995 | Deasy et al. |
| D359,802 | S | 6/1995 | Fontaine |
| 5,442,675 | A | 8/1995 | Swerdloff et al. |
| 5,548,627 | A | 8/1996 | Swerdloff et al. |
| 5,577,026 | A | 11/1996 | Gordon et al. |
| 5,661,773 | A | 8/1997 | Swerdloff et al. |
| 5,668,371 | A | 9/1997 | Deasy et al. |
| 5,724,400 | A | 3/1998 | Swerdloff et al. |
| 5,751,781 | A | 5/1998 | Brown et al. |
| 5,813,985 | A | 9/1998 | Carroll |
| 5,818,902 | A | 10/1998 | Yu |
| 5,851,182 | A | 12/1998 | Sahadevan |
| 5,889,834 | A | 3/1999 | Vilsmeier et al. |
| 5,917,883 | A * | 6/1999 | Khutoryansky ..... A61B 6/4225 378/98.2 |
| 5,937,028 | A | 8/1999 | Tybinkowski et al. |
| 5,946,425 | A | 8/1999 | Bove, Jr. et al. |
| 5,954,647 | A | 9/1999 | Bova et al. |
| 6,137,114 | A | 10/2000 | Rohe et al. |
| 6,180,943 | B1 | 1/2001 | Lange |
| 6,184,530 | B1 | 2/2001 | Hines et al. |
| 6,188,748 | B1 | 2/2001 | Pastyr et al. |
| 6,255,655 | B1 | 7/2001 | McCroskey et al. |
| 6,260,005 | B1 | 7/2001 | Yang et al. |
| 6,271,517 | B1 | 8/2001 | Kroening, Jr. et al. |
| 6,281,505 | B1 | 8/2001 | Hines et al. |
| 6,385,288 | B1 | 5/2002 | Kanematsu |
| 6,396,902 | B2 | 5/2002 | Tybinkowski et al. |
| 6,405,072 | B1 | 6/2002 | Cosman |
| 6,429,578 | B1 | 8/2002 | Danielsson et al. |
| 6,438,202 | B1 | 8/2002 | Olivera et al. |
| 6,449,331 | B1 | 9/2002 | Nutt et al. |
| 6,449,340 | B1 | 9/2002 | Tybinkowski et al. |
| 6,455,856 | B1 | 9/2002 | Gagnon |
| 6,459,769 | B1 | 10/2002 | Cosman |
| 6,504,899 | B2 | 1/2003 | Pugachev et al. |
| 6,560,311 | B1 | 5/2003 | Shepard et al. |
| 6,618,467 | B1 | 9/2003 | Ruchala et al. |
| 6,624,451 | B2 | 9/2003 | Ashley et al. |
| 6,628,744 | B1 * | 9/2003 | Luhta ..... G06T 11/005 378/15 |
| 6,661,866 | B1 | 12/2003 | Limkeman et al. |
| 6,696,694 | B2 | 2/2004 | Pastyr et al. |
| 6,700,949 | B2 | 3/2004 | Susami et al. |
| 6,714,076 | B1 | 3/2004 | Kalb |
| 6,730,924 | B1 | 5/2004 | Pastyr et al. |
| 6,735,277 | B2 | 5/2004 | McNutt et al. |
| 6,778,636 | B1 | 8/2004 | Andrews |
| 6,792,078 | B2 | 9/2004 | Kato et al. |
| 6,794,653 | B2 | 9/2004 | Wainer et al. |
| 6,810,103 | B1 | 10/2004 | Tybinkowski et al. |
| 6,810,108 | B2 | 10/2004 | Clark et al. |
| 6,831,961 | B1 | 12/2004 | Tybinkowski et al. |
| 6,841,784 | B2 | 1/2005 | Brahme et al. |
| 6,865,254 | B2 | 3/2005 | Nafstadius |
| 6,888,919 | B2 | 5/2005 | Graf |
| 6,891,166 | B2 | 5/2005 | Brahme et al. |
| 6,914,959 | B2 | 7/2005 | Bailey et al. |
| 6,934,363 | B2 | 8/2005 | Seufert |
| 6,965,661 | B2 | 11/2005 | Kojima et al. |
| 6,969,194 | B1 | 11/2005 | Nafstadius |
| 6,976,784 | B2 | 12/2005 | Kojima et al. |
| 6,990,175 | B2 | 1/2006 | Nakashima et al. |
| 7,016,522 | B2 | 3/2006 | Bani-Hashemi |
| 7,020,233 | B1 | 3/2006 | Tybinkowski et al. |
| 7,026,622 | B2 | 4/2006 | Kojima et al. |
| 7,085,347 | B2 | 8/2006 | Mihara et al. |
| 7,110,808 | B2 | 9/2006 | Adair |
| 7,120,223 | B2 | 10/2006 | Nafstadius |
| 7,129,495 | B2 | 10/2006 | Williams et al. |
| 7,154,096 | B2 | 12/2006 | Amano |
| 7,167,542 | B2 | 1/2007 | Juschka et al. |
| 7,177,386 | B2 | 2/2007 | Mostafavi et al. |
| 7,188,999 | B2 | 3/2007 | Mihara et al. |
| 7,191,100 | B2 | 3/2007 | Mostafavi |
| 7,199,382 | B2 | 4/2007 | Rigney et al. |
| 7,227,925 | B1 | 6/2007 | Mansfield et al. |
| 7,242,750 | B2 | 7/2007 | Tsujita |
| 7,263,165 | B2 | 8/2007 | Ghelmansarai |
| 7,265,356 | B2 | 9/2007 | Pelizzari et al. |
| 7,280,633 | B2 | 10/2007 | Cheng et al. |
| 7,291,840 | B2 | 11/2007 | Fritzler et al. |
| 7,297,958 | B2 | 11/2007 | Kojima et al. |
| 7,298,821 | B2 | 11/2007 | Ein-Gal |
| 7,301,144 | B2 | 11/2007 | Williams et al. |
| 7,310,410 | B2 | 12/2007 | Sohal et al. |
| 7,331,713 | B2 | 2/2008 | Moyers |
| 7,338,207 | B2 | 3/2008 | Gregerson et al. |
| 7,348,974 | B2 | 3/2008 | Smith et al. |
| 7,356,112 | B2 | 4/2008 | Brown et al. |
| 7,367,955 | B2 | 5/2008 | Zhang et al. |
| 7,386,099 | B1 | 6/2008 | Kasper et al. |
| 7,397,901 | B1 | 7/2008 | Johnsen |
| 7,397,902 | B2 | 7/2008 | Seeber et al. |
| 7,405,404 | B1 | 7/2008 | Shah |
| 7,412,029 | B2 | 8/2008 | Myles |
| 7,433,503 | B2 * | 10/2008 | Cherek ..... A61B 6/469 382/128 |
| 7,439,509 | B1 | 10/2008 | Grazioso et al. |
| 7,446,328 | B2 | 11/2008 | Rigney et al. |

(56) References Cited

U.S. PATENT DOCUMENTS

| | | |
|---|---|---|
| 7,453,983 B2 | 11/2008 | Schildkraut et al. |
| 7,453,984 B2 | 11/2008 | Chen et al. |
| 7,469,035 B2 | 12/2008 | Keall et al. |
| 7,496,181 B2 | 2/2009 | Mazin et al. |
| 7,545,911 B2 | 6/2009 | Rietzel et al. |
| 7,555,103 B2 | 6/2009 | Johnsen |
| 7,558,378 B2 | 7/2009 | Juschka et al. |
| 7,560,698 B2 | 7/2009 | Rietzel |
| 7,564,951 B2 | 7/2009 | Hasegawa et al. |
| 7,596,209 B2 | 9/2009 | Perkins |
| 7,620,444 B2 | 11/2009 | Le et al. |
| 7,627,082 B2 | 12/2009 | Kojima et al. |
| 7,639,853 B2 | 12/2009 | Olivera et al. |
| 7,649,981 B2 | 1/2010 | Seppi et al. |
| 7,656,999 B2 | 2/2010 | Hui et al. |
| 7,657,304 B2 | 2/2010 | Mansfield et al. |
| 7,679,049 B2 | 3/2010 | Rietzel |
| 7,693,256 B2 | 4/2010 | Brahme et al. |
| 7,711,087 B2 | 5/2010 | Mostafavi |
| 7,715,606 B2 | 5/2010 | Jeung et al. |
| 7,742,575 B2 | 6/2010 | Bourne |
| 7,755,054 B1 | 7/2010 | Shah et al. |
| 7,755,055 B2 | 7/2010 | Schilling |
| 7,755,057 B2 | 7/2010 | Kim |
| 7,769,430 B2 | 8/2010 | Mostafavi |
| 7,778,691 B2 | 8/2010 | Zhang et al. |
| 7,792,252 B2 | 9/2010 | Bohn |
| 7,795,590 B2 | 9/2010 | Takahashi et al. |
| 7,800,070 B2 | 9/2010 | Weinberg et al. |
| 7,820,975 B2 | 10/2010 | Laurence et al. |
| 7,820,989 B2 | 10/2010 | Sommer |
| 7,826,593 B2 | 11/2010 | Svensson et al. |
| 7,831,073 B2 | 11/2010 | Fu et al. |
| 7,839,972 B2 | 11/2010 | Ruchala et al. |
| 7,847,274 B2 | 12/2010 | Kornblau et al. |
| 7,869,562 B2 | 1/2011 | Khamene et al. |
| 7,869,862 B2 | 1/2011 | Seppi et al. |
| 7,885,371 B2 | 2/2011 | Thibault et al. |
| 7,939,808 B1 | 5/2011 | Shah et al. |
| 7,942,843 B2 | 5/2011 | Tune et al. |
| 7,952,079 B2 | 5/2011 | Neustadter et al. |
| 7,957,507 B2 | 6/2011 | Cadman |
| 7,965,819 B2 | 6/2011 | Nagata |
| 7,983,380 B2 | 7/2011 | Guertin et al. |
| 8,017,915 B2 | 9/2011 | Mazin |
| 8,019,042 B2 | 9/2011 | Shukla et al. |
| 8,059,782 B2 | 11/2011 | Brown |
| 8,060,177 B2 | 11/2011 | Hamill |
| 8,063,376 B2 | 11/2011 | Maniawski et al. |
| 8,090,074 B2 | 1/2012 | Filiberti et al. |
| 8,093,568 B2 | 1/2012 | Mackie et al. |
| 8,116,427 B2 | 2/2012 | Kojima et al. |
| 8,130,384 B2 | 3/2012 | Kindlein et al. |
| 8,139,713 B2 | 3/2012 | Janbakhsh |
| 8,139,714 B1 | 3/2012 | Sahadevan |
| 8,144,962 B2 | 3/2012 | Busch et al. |
| 8,148,695 B2 | 4/2012 | Takahashi et al. |
| 8,148,703 B2 | 4/2012 | Sommer |
| 8,160,205 B2 | 4/2012 | Saracen et al. |
| 8,193,508 B2 | 6/2012 | Shchory et al. |
| 8,198,600 B2 | 6/2012 | Neustadter et al. |
| 8,232,535 B2 | 7/2012 | Olivera et al. |
| 8,235,530 B2 | 8/2012 | Maad |
| 8,239,002 B2 | 8/2012 | Neustadter et al. |
| 8,269,195 B2 | 9/2012 | Rigney et al. |
| 8,278,633 B2 | 10/2012 | Nord et al. |
| 8,280,002 B2 | 10/2012 | Bani-Hashemi et al. |
| 8,295,435 B2 | 10/2012 | Wang et al. |
| 8,295,906 B2 | 10/2012 | Saunders et al. |
| 8,303,505 B2 | 11/2012 | Webler et al. |
| 8,304,738 B2 | 11/2012 | Gagnon et al. |
| 8,306,185 B2 | 11/2012 | Bal et al. |
| 8,311,185 B2 | 11/2012 | Seppi et al. |
| 8,335,296 B2 | 12/2012 | Dehler et al. |
| 8,357,903 B2 | 1/2013 | Wang et al. |
| 8,384,049 B1 | 2/2013 | Broad |
| 8,395,127 B1 | 3/2013 | Frach et al. |
| 8,406,844 B2 | 3/2013 | Ruchala et al. |
| 8,406,851 B2 | 3/2013 | West et al. |
| 8,442,287 B2 | 5/2013 | Fordyce, II et al. |
| 8,461,538 B2 | 6/2013 | Mazin |
| 8,461,539 B2 | 6/2013 | Yamaya et al. |
| 8,467,497 B2 | 6/2013 | Lu et al. |
| 8,483,803 B2 | 7/2013 | Partain et al. |
| 8,509,383 B2 | 8/2013 | Lu et al. |
| 8,520,800 B2 | 8/2013 | Wilfley et al. |
| 8,536,547 B2 | 9/2013 | Maurer, Jr. et al. |
| 8,537,373 B2 | 9/2013 | Humphrey |
| 8,571,639 B2 | 10/2013 | Mostafavi |
| 8,581,196 B2 | 11/2013 | Yamaya et al. |
| 8,588,367 B2 | 11/2013 | Busch et al. |
| 8,594,769 B2 | 11/2013 | Mostafavi |
| 8,617,422 B2 | 12/2013 | Koschan et al. |
| 8,641,592 B2 | 2/2014 | Yu |
| 8,664,610 B2 | 3/2014 | Chuang |
| 8,664,618 B2 | 3/2014 | Yao |
| 8,712,012 B2 | 4/2014 | O'Connor |
| 8,745,789 B2 | 6/2014 | Saracen et al. |
| 8,748,825 B2 | 6/2014 | Mazin |
| 8,767,917 B2 | 7/2014 | Ruchala et al. |
| 8,788,020 B2 | 7/2014 | Mostafavi et al. |
| 8,816,307 B2 | 8/2014 | Kuusela et al. |
| 8,873,710 B2 | 10/2014 | Ling et al. |
| 8,884,240 B1 | 11/2014 | Shah et al. |
| 8,939,920 B2 | 1/2015 | Maad |
| 8,992,404 B2 | 3/2015 | Graf et al. |
| 9,061,141 B2 | 6/2015 | Brunker et al. |
| 9,179,982 B2 | 11/2015 | Kunz et al. |
| 9,205,281 B2 | 12/2015 | Mazin |
| 9,232,928 B2 | 1/2016 | Mostafavi |
| 9,248,312 B2 | 2/2016 | Li et al. |
| 9,360,570 B2 | 6/2016 | Rothfuss et al. |
| 9,370,672 B2 | 6/2016 | Parsai et al. |
| 9,437,339 B2 | 9/2016 | Echner |
| 9,437,340 B2 | 9/2016 | Echner et al. |
| 9,498,167 B2 | 11/2016 | Mostafavi et al. |
| 9,560,970 B2 | 2/2017 | Rose et al. |
| 9,575,192 B1 | 2/2017 | Ng et al. |
| 9,649,509 B2 | 5/2017 | Mazin et al. |
| 9,697,980 B2 | 7/2017 | Ogura et al. |
| 9,731,148 B2 | 8/2017 | Olivera et al. |
| 9,820,700 B2 | 11/2017 | Mazin |
| 9,878,180 B2 | 1/2018 | Schulte et al. |
| 9,886,534 B2 | 2/2018 | Wan et al. |
| 9,952,878 B2 | 4/2018 | Grimme et al. |
| 9,974,494 B2 | 5/2018 | Mostafavi et al. |
| 10,159,853 B2 | 12/2018 | Kuusela et al. |
| 10,327,716 B2 | 6/2019 | Mazin |
| 10,478,133 B2 | 11/2019 | Levy et al. |
| 10,603,515 B2 | 3/2020 | Olcott et al. |
| 10,617,890 B2 | 4/2020 | Mazin et al. |
| 10,646,188 B2 | 5/2020 | Mostafavi et al. |
| 10,695,583 B2 | 6/2020 | Mazin et al. |
| 10,695,586 B2 | 6/2020 | Harper et al. |
| 10,745,253 B2 | 8/2020 | Saracen et al. |
| 10,795,037 B2 | 10/2020 | Olcott et al. |
| 10,959,686 B2 | 3/2021 | Mazin |
| 11,007,384 B2 | 5/2021 | Olcott et al. |
| 11,285,340 B2 | 3/2022 | Larkin et al. |
| 11,287,540 B2 | 3/2022 | Olcott et al. |
| 11,309,072 B2 | 4/2022 | Carmi |
| 11,369,806 B2 | 6/2022 | Laurence, Jr. et al. |
| 11,504,550 B2 | 11/2022 | Maolinbay |
| 11,511,133 B2 | 11/2022 | Olcott et al. |
| 11,520,415 B2 | 12/2022 | Douglas et al. |
| 11,627,920 B2 | 4/2023 | Mazin |
| 11,642,027 B2 | 5/2023 | Otto |
| 11,675,097 B2 | 6/2023 | Olcott et al. |
| 2002/0051513 A1 | 5/2002 | Pugachev et al. |
| 2002/0085668 A1 | 7/2002 | Blumhofer et al. |
| 2002/0148970 A1 | 10/2002 | Wong et al. |
| 2002/0163994 A1 | 11/2002 | Jones |
| 2002/0191734 A1 | 12/2002 | Kojima et al. |
| 2002/0193685 A1 | 12/2002 | Mate et al. |

(56) References Cited

U.S. PATENT DOCUMENTS

| | | |
|---|---|---|
| 2003/0036700 A1 | 2/2003 | Weinberg |
| 2003/0043951 A1 | 3/2003 | Akers |
| 2003/0058984 A1 | 3/2003 | Susami et al. |
| 2003/0080298 A1 | 5/2003 | Karplus et al. |
| 2003/0105397 A1 | 6/2003 | Tumer et al. |
| 2003/0128801 A1 | 7/2003 | Eisenberg et al. |
| 2003/0219098 A1 | 11/2003 | McNutt et al. |
| 2004/0002641 A1 | 1/2004 | Sjogren et al. |
| 2004/0024300 A1 | 2/2004 | Graf |
| 2004/0030246 A1 | 2/2004 | Townsend et al. |
| 2004/0037390 A1 | 2/2004 | Mihara et al. |
| 2004/0057557 A1 | 3/2004 | Nafstadius |
| 2004/0158416 A1 | 8/2004 | Slates |
| 2004/0162457 A1 | 8/2004 | Maggiore et al. |
| 2004/0218719 A1 | 11/2004 | Brown et al. |
| 2005/0028279 A1 | 2/2005 | de Mooy |
| 2005/0104001 A1 | 5/2005 | Shah |
| 2005/0213705 A1 | 9/2005 | Hoffman |
| 2005/0228255 A1 | 10/2005 | Saracen et al. |
| 2005/0234327 A1 | 10/2005 | Saracen et al. |
| 2006/0002511 A1 | 1/2006 | Miller et al. |
| 2006/0058637 A1 | 3/2006 | Sommer |
| 2006/0072699 A1 | 4/2006 | Mackie et al. |
| 2006/0113482 A1 | 6/2006 | Pelizzari et al. |
| 2006/0124854 A1 | 6/2006 | Shah |
| 2006/0173294 A1 | 8/2006 | Ein-Gal |
| 2006/0182326 A1 | 8/2006 | Schildkraut et al. |
| 2006/0193435 A1 | 8/2006 | Hara et al. |
| 2006/0237652 A1 | 10/2006 | Kimchy et al. |
| 2007/0003010 A1* | 1/2007 | Guertin ............... A61B 6/4441 378/63 |
| 2007/0003123 A1 | 1/2007 | Fu et al. |
| 2007/0014391 A1 | 1/2007 | Mostafavi et al. |
| 2007/0023669 A1 | 2/2007 | Hefetz et al. |
| 2007/0025496 A1 | 2/2007 | Brown et al. |
| 2007/0025513 A1 | 2/2007 | Ghelmansarai |
| 2007/0043289 A1 | 2/2007 | Adair |
| 2007/0053491 A1 | 3/2007 | Schildkraut et al. |
| 2007/0055144 A1 | 3/2007 | Neustadter et al. |
| 2007/0133749 A1 | 6/2007 | Mazin et al. |
| 2007/0153969 A1 | 7/2007 | Maschke |
| 2007/0164239 A1 | 7/2007 | Terwilliger et al. |
| 2007/0165779 A1 | 7/2007 | Chen et al. |
| 2007/0167801 A1 | 7/2007 | Webler et al. |
| 2007/0211857 A1 | 9/2007 | Urano et al. |
| 2007/0221869 A1 | 9/2007 | Song |
| 2007/0237290 A1 | 10/2007 | Mostafavi |
| 2007/0265230 A1 | 11/2007 | Rousso et al. |
| 2007/0265528 A1 | 11/2007 | Xu et al. |
| 2007/0270693 A1 | 11/2007 | Fiedler et al. |
| 2008/0002811 A1 | 1/2008 | Allison |
| 2008/0031404 A1 | 2/2008 | Khamene et al. |
| 2008/0043910 A1 | 2/2008 | Thomas |
| 2008/0095416 A1 | 4/2008 | Jeung et al. |
| 2008/0103391 A1 | 5/2008 | Dos Santos Varela |
| 2008/0128631 A1 | 6/2008 | Suhami |
| 2008/0130825 A1 | 6/2008 | Fu et al. |
| 2008/0152085 A1 | 6/2008 | Saracen et al. |
| 2008/0156993 A1 | 7/2008 | Weinberg et al. |
| 2008/0164875 A1 | 7/2008 | Haworth et al. |
| 2008/0203309 A1 | 8/2008 | Frach et al. |
| 2008/0205588 A1 | 8/2008 | Kim |
| 2008/0214927 A1 | 9/2008 | Cherry et al. |
| 2008/0217541 A1 | 9/2008 | Kim |
| 2008/0230705 A1 | 9/2008 | Rousso et al. |
| 2008/0240352 A1 | 10/2008 | Brahme et al. |
| 2008/0251709 A1 | 10/2008 | Cooke et al. |
| 2008/0253516 A1 | 10/2008 | Hui et al. |
| 2008/0262473 A1 | 10/2008 | Kornblau et al. |
| 2008/0272284 A1 | 11/2008 | Rietzel |
| 2008/0273659 A1 | 11/2008 | Guertin et al. |
| 2008/0298536 A1 | 12/2008 | Ein-Gal |
| 2009/0003655 A1 | 1/2009 | Wollenweber |
| 2009/0086909 A1 | 4/2009 | Hui et al. |
| 2009/0088622 A1 | 4/2009 | Mostafavi |
| 2009/0116616 A1 | 5/2009 | Lu et al. |
| 2009/0131734 A1 | 5/2009 | Neustadter et al. |
| 2009/0169082 A1 | 7/2009 | Mizuta et al. |
| 2009/0236532 A1 | 9/2009 | Frach et al. |
| 2009/0256078 A1 | 10/2009 | Mazin |
| 2009/0285357 A1 | 11/2009 | Khamene et al. |
| 2009/0309046 A1 | 12/2009 | Balakin |
| 2010/0010343 A1 | 1/2010 | Daghighian et al. |
| 2010/0040197 A1 | 2/2010 | Maniawski et al. |
| 2010/0049030 A1 | 2/2010 | Saunders et al. |
| 2010/0054412 A1 | 3/2010 | Brinks et al. |
| 2010/0063384 A1 | 3/2010 | Kornblau et al. |
| 2010/0065723 A1 | 3/2010 | Burbar et al. |
| 2010/0067660 A1* | 3/2010 | Maurer, Jr. ............ A61B 6/486 378/95 |
| 2010/0069742 A1 | 3/2010 | Partain et al. |
| 2010/0074400 A1 | 3/2010 | Sendai |
| 2010/0074498 A1 | 3/2010 | Breeding et al. |
| 2010/0166274 A1 | 7/2010 | Busch et al. |
| 2010/0176309 A1 | 7/2010 | Mackie et al. |
| 2010/0198063 A1 | 8/2010 | Huber et al. |
| 2010/0237259 A1 | 9/2010 | Wang |
| 2010/0266099 A1 | 10/2010 | Busch et al. |
| 2010/0276601 A1 | 11/2010 | Duraj et al. |
| 2011/0006212 A1 | 1/2011 | Shchory et al. |
| 2011/0044429 A1 | 2/2011 | Takahashi et al. |
| 2011/0073763 A1 | 3/2011 | Subbarao |
| 2011/0092814 A1 | 4/2011 | Yamaya et al. |
| 2011/0105895 A1 | 5/2011 | Kornblau et al. |
| 2011/0105897 A1 | 5/2011 | Kornblau et al. |
| 2011/0118588 A1 | 5/2011 | Kornblau et al. |
| 2011/0198504 A1 | 8/2011 | Eigen |
| 2011/0200170 A1 | 8/2011 | Nord et al. |
| 2011/0210261 A1 | 9/2011 | Maurer, Jr. |
| 2011/0211665 A1 | 9/2011 | Maurer, Jr. et al. |
| 2011/0215248 A1 | 9/2011 | Lewellen et al. |
| 2011/0215259 A1 | 9/2011 | Iwata |
| 2011/0272600 A1 | 11/2011 | Bert et al. |
| 2011/0297833 A1 | 12/2011 | Takayama |
| 2011/0301449 A1 | 12/2011 | Maurer, Jr. |
| 2011/0309252 A1 | 12/2011 | Moriyasu et al. |
| 2011/0309255 A1 | 12/2011 | Bert et al. |
| 2011/0313231 A1 | 12/2011 | Guertin et al. |
| 2011/0313232 A1 | 12/2011 | Balakin |
| 2012/0035470 A1 | 2/2012 | Kuduvalli et al. |
| 2012/0068076 A1 | 3/2012 | Daghighian |
| 2012/0076269 A1 | 3/2012 | Roberts |
| 2012/0083681 A1 | 4/2012 | Guckenburger et al. |
| 2012/0138806 A1 | 6/2012 | Holmes et al. |
| 2012/0161014 A1 | 6/2012 | Yamaya et al. |
| 2012/0174317 A1 | 7/2012 | Saracen et al. |
| 2012/0189102 A1 | 7/2012 | Maurer, Jr. et al. |
| 2012/0213334 A1 | 8/2012 | Dirauf et al. |
| 2012/0230464 A1 | 9/2012 | Ling et al. |
| 2012/0245453 A1 | 9/2012 | Tryggestad et al. |
| 2012/0318989 A1 | 12/2012 | Park et al. |
| 2012/0323117 A1 | 12/2012 | Neustadter et al. |
| 2013/0025055 A1 | 1/2013 | Saracen et al. |
| 2013/0060134 A1 | 3/2013 | Eshima et al. |
| 2013/0092842 A1 | 4/2013 | Zhang et al. |
| 2013/0109904 A1* | 5/2013 | Siljamaki ............ A61N 5/1067 600/1 |
| 2013/0111668 A1 | 5/2013 | Wiggers et al. |
| 2013/0193330 A1 | 8/2013 | Wagadarikar et al. |
| 2013/0266116 A1 | 10/2013 | Abenaim et al. |
| 2013/0279658 A1 | 10/2013 | Mazin |
| 2013/0327932 A1 | 12/2013 | Kim et al. |
| 2013/0343509 A1 | 12/2013 | Gregerson et al. |
| 2014/0029715 A1 | 1/2014 | Hansen et al. |
| 2014/0104051 A1* | 4/2014 | Breed ................ G08G 1/09626 340/435 |
| 2014/0107390 A1 | 4/2014 | Brown et al. |
| 2014/0110573 A1 | 4/2014 | Wang et al. |
| 2014/0163368 A1 | 6/2014 | Rousso et al. |
| 2014/0184197 A1 | 7/2014 | Dolinsky |
| 2014/0193336 A1 | 7/2014 | Rousso et al. |
| 2014/0217294 A1 | 8/2014 | Rothfuss et al. |
| 2014/0224963 A1 | 8/2014 | Guo et al. |
| 2014/0228613 A1 | 8/2014 | Mazin et al. |

(56) References Cited

U.S. PATENT DOCUMENTS

| | | |
|---|---|---|
| 2014/0239204 A1 | 8/2014 | Orton et al. |
| 2014/0257096 A1 | 9/2014 | Prevrhal et al. |
| 2014/0341351 A1 | 11/2014 | Berwick et al. |
| 2014/0355735 A1* | 12/2014 | Choi .................. A61B 6/022 378/54 |
| 2014/0371581 A1 | 12/2014 | Mostafavi et al. |
| 2015/0018673 A1 | 1/2015 | Rose et al. |
| 2015/0035942 A1 | 2/2015 | Hampton et al. |
| 2015/0060685 A1 | 3/2015 | Maad et al. |
| 2015/0076357 A1 | 3/2015 | Frach |
| 2015/0078528 A1 | 3/2015 | Okada |
| 2015/0126801 A1 | 5/2015 | Matteo et al. |
| 2015/0131774 A1 | 5/2015 | Maurer, Jr. et al. |
| 2015/0168567 A1 | 6/2015 | Kim et al. |
| 2015/0177394 A1 | 6/2015 | Dolinsky et al. |
| 2015/0190658 A1 | 7/2015 | Yu |
| 2015/0265852 A1 | 9/2015 | Meir et al. |
| 2015/0276947 A1 | 10/2015 | Hoenk et al. |
| 2015/0285922 A1 | 10/2015 | Mintzer et al. |
| 2015/0301201 A1 | 10/2015 | Rothfuss et al. |
| 2016/0023019 A1* | 1/2016 | Filiberti ............... A61N 5/107 600/1 |
| 2016/0073977 A1 | 3/2016 | Mazin |
| 2016/0097866 A1 | 4/2016 | Williams |
| 2016/0146949 A1 | 5/2016 | Frach et al. |
| 2016/0155228 A1 | 6/2016 | Sakata et al. |
| 2016/0206203 A1 | 7/2016 | Yu et al. |
| 2016/0209515 A1 | 7/2016 | Da Silva Rodrigues et al. |
| 2016/0219686 A1 | 7/2016 | Nakayama et al. |
| 2016/0266260 A1 | 9/2016 | Preston |
| 2016/0273958 A1 | 9/2016 | Hoenk et al. |
| 2016/0287347 A1* | 10/2016 | Meier .................. A61B 6/4007 |
| 2016/0299240 A1 | 10/2016 | Cho et al. |
| 2016/0325117 A1 | 11/2016 | Arai |
| 2016/0361566 A1 | 12/2016 | Larkin et al. |
| 2016/0374632 A1* | 12/2016 | David .................. A61B 6/4423 378/161 |
| 2017/0014648 A1* | 1/2017 | Mostafavi ............ A61N 5/1081 |
| 2017/0036039 A1 | 2/2017 | Gaudio |
| 2017/0052266 A1 | 2/2017 | Kim et al. |
| 2017/0065834 A1 | 3/2017 | Liu |
| 2017/0082759 A1 | 3/2017 | Lyu et al. |
| 2017/0199284 A1 | 7/2017 | Silari et al. |
| 2017/0220709 A1* | 8/2017 | Wan .................... A61N 5/1048 |
| 2017/0242136 A1 | 8/2017 | O'Neill et al. |
| 2017/0281975 A1 | 10/2017 | Filiberti et al. |
| 2018/0133508 A1 | 5/2018 | Pearce et al. |
| 2018/0292550 A1 | 10/2018 | Xu et al. |
| 2019/0070437 A1 | 3/2019 | Olcott et al. |
| 2019/0126069 A1 | 5/2019 | Nord et al. |
| 2019/0357859 A1 | 11/2019 | Mazin |
| 2020/0164230 A1 | 5/2020 | Larkin et al. |
| 2020/0215355 A1 | 7/2020 | Olcott et al. |
| 2020/0222724 A1 | 7/2020 | Mazin et al. |
| 2020/0368551 A1 | 11/2020 | Bassalow et al. |
| 2020/0368557 A1 | 11/2020 | Harper et al. |
| 2021/0196212 A1 | 7/2021 | Mazin |
| 2021/0267683 A1 | 9/2021 | Brown |
| 2021/0327560 A1 | 10/2021 | Carmi |
| 2022/0093285 A1 | 3/2022 | Burns |
| 2022/0096867 A1 | 3/2022 | Mazin et al. |
| 2022/0143422 A1 | 5/2022 | Harper |
| 2022/0193451 A1 | 6/2022 | Duval et al. |
| 2022/0296929 A1 | 9/2022 | Laurence, Jr. et al. |
| 2022/0342095 A1 | 10/2022 | Olcott et al. |
| 2022/0395707 A1 | 12/2022 | Laurence, Jr. et al. |
| 2023/0218928 A1 | 7/2023 | Maolinbay |
| 2023/0256268 A1 | 8/2023 | Olcott et al. |
| 2023/0337991 A1 | 10/2023 | Mazin |
| 2023/0393292 A1 | 12/2023 | Olcott et al. |

FOREIGN PATENT DOCUMENTS

| | | |
|---|---|---|
| CN | 1960780 A | 5/2007 |
| CN | 101297759 A | 11/2008 |
| CN | 101378805 A | 3/2009 |
| CN | 101803929 A | 8/2010 |
| CN | 101970043 A | 2/2011 |
| CN | 103071241 A | 5/2013 |
| CN | 103648392 A | 3/2014 |
| CN | 103650095 A | 3/2014 |
| CN | 103932789 A | 7/2014 |
| CN | 105073188 A | 11/2015 |
| CN | 106461801 A | 2/2017 |
| DE | 10-2008-053321 A1 | 5/2010 |
| DE | 10-2013-205606 A1 | 10/2014 |
| EP | 0 437 434 A1 | 7/1995 |
| EP | 0 817 978 A1 | 8/2001 |
| EP | 0 984 393 B1 | 3/2007 |
| EP | 1 762 177 A2 | 3/2007 |
| EP | 1 501 604 B1 | 12/2009 |
| EP | 1 898 234 B1 | 4/2010 |
| EP | 2 188 815 B1 | 11/2011 |
| EP | 2 535 086 A1 | 12/2012 |
| EP | 2 687 259 A1 | 1/2014 |
| EP | 2 872 913 B1 | 2/2016 |
| EP | 2 874 702 B1 | 9/2016 |
| EP | 1 664 752 B1 | 6/2017 |
| EP | 3 720 554 B1 | 7/2021 |
| FR | 2839894 A1 | 11/2003 |
| GB | 69634119 T2 | 2/2006 |
| GB | 2513596 A | 11/2014 |
| IL | 208396 | 12/2010 |
| JP | H-01-156830 A | 6/1989 |
| JP | H-09-122110 A | 5/1997 |
| JP | 9-189769 A2 | 7/1997 |
| JP | H-11-290466 A | 10/1999 |
| JP | 2002-263090 A | 9/2002 |
| JP | 2003-534823 A | 11/2003 |
| JP | 2005-261941 A | 9/2005 |
| JP | 2007-502166 A | 2/2007 |
| JP | 2007-507246 A | 3/2007 |
| JP | 2008-107326 A | 5/2008 |
| JP | 2008-173184 A | 7/2008 |
| JP | 2008-173299 A | 7/2008 |
| JP | 2009-544101 A | 12/2009 |
| JP | 2010-500910 A | 1/2010 |
| JP | 2011-508654 A | 3/2011 |
| JP | 2011-514213 A | 5/2011 |
| JP | 2012-042344 A | 3/2012 |
| JP | 2012-129984 A | 7/2012 |
| JP | 2012-254146 A | 12/2012 |
| JP | 2013-257320 A | 12/2013 |
| JP | 2013-545560 A | 12/2013 |
| JP | 2014-521370 A | 8/2014 |
| JP | 2017-199876 A | 11/2017 |
| NL | 9520013 A | 2/1997 |
| WO | WO-89/10090 A1 | 11/1989 |
| WO | WO-95/22241 A1 | 8/1995 |
| WO | WO-00/15299 A1 | 3/2000 |
| WO | WO-2004/017832 A2 | 3/2004 |
| WO | WO-2004/017832 A3 | 3/2004 |
| WO | WO-2005/018734 A2 | 3/2005 |
| WO | WO-2005/018734 A3 | 3/2005 |
| WO | WO-2005/018735 A2 | 3/2005 |
| WO | WO-2005/018735 A3 | 3/2005 |
| WO | WO-2005/110495 A1 | 11/2005 |
| WO | WO-2006/051531 A2 | 5/2006 |
| WO | WO-2006/051531 A3 | 5/2006 |
| WO | WO-2006/086765 A2 | 8/2006 |
| WO | WO-2006/086765 A3 | 8/2006 |
| WO | WO-2007/045076 A1 | 4/2007 |
| WO | WO-2007/094002 A2 | 8/2007 |
| WO | WO-2007/094002 A3 | 8/2007 |
| WO | WO-2007/120674 A2 | 10/2007 |
| WO | WO-2007/120674 A3 | 10/2007 |
| WO | WO-2007/124760 A1 | 11/2007 |
| WO | WO-2008/019118 A2 | 2/2008 |
| WO | WO-2008/019118 A3 | 2/2008 |
| WO | WO-2008/024463 A2 | 2/2008 |

(56) References Cited

FOREIGN PATENT DOCUMENTS

| | | |
|---|---|---|
| WO | WO-2008/024463 A3 | 2/2008 |
| WO | WO-2008/127368 A2 | 10/2008 |
| WO | WO-2008/127368 A3 | 10/2008 |
| WO | WO-2009/114117 A2 | 9/2009 |
| WO | WO-2009/114117 A3 | 9/2009 |
| WO | WO-2010/015358 A1 | 2/2010 |
| WO | WO-2010/018477 A2 | 2/2010 |
| WO | WO-2010/018477 A3 | 2/2010 |
| WO | WO-2010/109585 A1 | 9/2010 |
| WO | WO-2010/110255 A1 | 9/2010 |
| WO | WO-2012/135771 A1 | 10/2012 |
| WO | WO-2013/168043 A2 | 11/2013 |
| WO | WO-2013/168043 A3 | 11/2013 |
| WO | WO-2015/038832 A1 | 3/2015 |
| WO | WO-2015/042510 A1 | 3/2015 |
| WO | WO-2015/103564 A1 | 7/2015 |
| WO | WO-2015/134953 A1 | 9/2015 |
| WO | WO-2015/161036 A1 | 10/2015 |
| WO | WO-2016/097977 A1 | 6/2016 |
| WO | WO-2016/203822 A1 | 12/2016 |
| WO | WO-2017/220116 A1 | 12/2017 |

OTHER PUBLICATIONS

Chang, J.Y. et al. (2008). "Image-guided radiation therapy for non-small cell lung cancer," *J. Thorac. Oncol.* 3(2):177-186.
Chen, Y. et al. (2011). Dynamic tomotherapy delivery, *Am. Assoc. Phys. Med.* 38:3013-3024.
Corrected Notice of Allowability dated Jan. 29, 2020, for U.S. Appl. No. 16/100,054, filed Aug. 9, 2018, 4 pages.
Corrected Notice of Allowability dated Feb. 3, 2021, for U.S. Appl. No. 16/425,416, filed May 29, 2019, 2 pages.
Corrected Notice of Allowability dated May 17, 2022, for U.S. Appl. No. 16/191,131, filed Nov. 14, 2018, 8 pages.
Corrected Notice of Allowability dated Feb. 14, 2023, for U.S. Appl. No. 17/697,828, filed Mar. 17, 2022, 4 pages.
Corrected Notice of Allowability dated Feb. 23, 2023, for U.S. Appl. No. 17/697,828, filed Mar. 17, 2022, 2 pages.
Corrected Notice of Allowability dated Mar. 16, 2023, for U.S. Appl. No. 17/203,532, filed Mar. 16, 2021, 2 pages.
Dieterich, S. et al. (2003). "Skin respiratory motion tracking for stereotactic radiosurgery using the CyberKnife," *Elsevier Int'l Congress Series* 1256:130-136.
Erdi, Y.E. (2007). "The use of PET for radiotherapy," *Curr. Medical Imaging Reviews* 3(1):3-16.
Extended European Search Report dated Oct. 7, 2015, for European Application No. 12 763 280.0, filed on Mar. 30, 2012, 11 pages.
Extended European Search Report dated Mar. 31, 2017, for European Application No. 09 719 473.2, filed on Mar. 9, 2009, 8 pages.
Extended European Search Report dated Jun. 9, 2020, for EP Application No. 17 871 349.1, filed on Nov. 15, 2017, 6 pages.
Extended European Search Report dated Oct. 30, 2020, for EP Application No. 20 179 036.7, filed on Mar. 9, 2009, 12 pages.
Extended European Search Report dated May 26, 2021, for EP Application No. 18 832 571.6, filed on Jul. 11, 2018, 9 pages.
Extended European Search Report dated Mar. 30, 2022, for EP Application No. 21 195 331.0, filed on Nov. 15, 2017, 11 pages.
Fan, Q. et al. (2012). "Emission Guided Radiation Therapy for Lung and Prostrate Cancers: A Feasibility Study on a Digital Patient," *Med. Phys.* 39(11):7140-7152.
Fan, Q. et al. (2013). "Toward a Planning Scheme for Emission Guided Radiation Therapy (EGRT): FDG Based Tumor Tracking in a Metastatic Breast Cancer Patient," *Med. Phys.* 40(8): 12 pages.
Final Office Action dated Aug. 15, 2012, for U.S. Appl. No. 13/209,275, filed Aug. 12, 2011, 8 pages.
Final Office Action dated Aug. 10, 2021, for U.S. Appl. No. 16/887,896, filed May 29, 2020, 66 pages.
Final Office Action dated Jan. 11, 2022, for U.S. Appl. No. 16/191,131, filed Nov. 14, 2018, 25 pages.

Freeman, T. (2015). "Radiotherapy needs preclinical research," Medical Physics Web, 4 total pages.
Galvin, J.M. (2018). "The multileaf collimator—A complete guide," 17 total pages.
Gibbons, J.P. (2004). "Dose calculation and verification for tomotherapy," 2004 ACMP Meeting, Scottsdale, AZ., 71 total pages.
Glendinning, A.G. et al. (2001). "Measurement of the response of $Gd_2O_2S$:Tb phosphor to 6 MV x-rays," Phys. Mol. Biol. 46:517-530.
Handsfield, L.L. et al. (2014). "Phantomless patient-specific TomoTherapy QA via delivery performance monitoring and a secondary Monte Carlo dose calculation," *Med. Phys.* 41:101703-1-101703-9.
International Search Report dated May 4, 2009, for PCT Application No. PCT/US2009/01500, filed on Mar. 9, 2009, 3 pages.
International Search Report dated Mar. 7, 2018, for PCT Application No. PCT/US2017/061848, filed on Nov. 15, 2017, 4 pages.
International Search Report dated Oct. 2, 2018, for PCT Application No. PCT/US2018/041700, filed on Jul. 11, 2018, 2 pages.
International Search Report dated Oct. 24, 2018, for PCT Application No. PCT/US2018/046132, filed on Aug. 9, 2018, 2 pages.
International Search Report dated Mar. 13, 2018, for PCT Application No. PCT/US2017/061855, filed on Nov. 15, 2017, 4 pages.
International Search Report dated Jun. 20, 2018, for PCT Application No. PCT/US2018/025252, filed on Mar. 29, 2018, 2 pages.
International Search Report dated Jan. 30, 2019, for PCT Application No. PCT/US2018/061099, filed on Nov. 14, 2018, 4 pages.
Kapatoes, J.M. et al. (2001). "A feasible method for clinical delivery verification and dose reconstruction in tomotherapy," *Med. Phys.* 28:528-542.
Keall, P.J. et al. (2001). "Motion adaptive x-ray therapy: a feasibility study," *Phys. Med. Biol.* 46:1-10.
Keyence (2019). Ultra-high speed in-line profilometer—LJV7000 series, 3 total pages.
Kim, H. et al. (2009). "A multi-threshold method for the TOF-PET Signal Processing," Nucl. Instrum. Meth. Phys. Res. A. 602:618-621.
Krouglicof, N. et al. (2013). "Development of a Novel PCB-Based Voice Coil Actuator for Opto-Mechatronic Applications," *presented at IEEE/RSJ International Conference on Intelligent Robots and Systems (IROS)*, Tokyo, Japan, Nov. 3-7, 2013, pp. 5834-5840.
Langen, K.M. et al. (2010). "QA for helical tomotherapy: report of the AAPM Task Group 148," *Med. Phys.* 37:4817-4853.
Li, X. et al. (2016). "Timing calibration for Time-of-Flight PET using positron-emitting isotopes and annihilation targets," IEEE Transactions on Nuclear Science 63:1351-1358.
Lu, W. (2009). "Real-time motion-adaptive-optimization (MAO) in tomotherapy," Phys. Med. Biol. 54:4373-4398.
Lu, W. (2008). "Real-time motion-adaptive delivery (MAD) using binary MLC: I. Static beam (topotherapy) delivery," Phys. Med. Biol. 53:6491-6511.
Mackie, T.R. et al. (Nov.-Dec. 1993). "Tomotherapy: A New Concept for the Delivery of Dynamic Conformal Radiotherapy," *Med. Phys.* 20(6):1709-1719.
McMahon, R. et al. (2008). "A real-time dynamic-MLC control algorithm for delivering IMRT to targets undergoing 2D rigid motion in the beam's eye view," Med. Phys. 35:3875-3888.
Mazin, S. R. et al. (2010). "Emission-Guided Radiation Therapy: Biologic Targeting and Adaptive Treatment," *Journal of American College of Radiology* 7(12):989-990.
Non-Final Office Action dated Jan. 10, 2011, for U.S. Appl. No. 12/367,679, filed Feb. 9, 2009, 9 pages.
Non-Final Office Action dated Feb. 28, 2012, for U.S. Appl. No. 13/209,275, filed Aug. 12, 2011, 9 pages.
Non-Final Office Action dated Sep. 19, 2013, for U.S. Appl. No. 13/895,255, filed May 15, 2013, 8 pages.
Non-Final Office Action dated Jan. 7, 2020, for U.S. Appl. No. 15/814,222, filed Nov. 15, 2017, 13 pages.
Non-Final Office Action dated Oct. 5, 2020, for U.S. Appl. No. 16/887,896, filed May 29, 2020, 62 pages.
Non-Final Office Action dated Nov. 3, 2020, for U.S. Appl. No. 16/818,325, filed Mar. 13, 2020, 9 pages.

(56) References Cited

OTHER PUBLICATIONS

Non-Final Office Action dated Mar. 12, 2021, for U.S. Appl. No. 16/887,896, filed May 29, 2020, 64 pages.
Non-Final Office Action dated Apr. 26, 2021, for U.S. Appl. No. 16/191,131, filed Nov. 14, 2018, 28 pages.
Non-Final Office Action dated Jul. 5, 2022, for U.S. Appl. No. 17/203,532, filed Mar. 16, 2021, 13 pages.
Non-Final Office Action dated Dec. 14, 2022, for U.S. Appl. No. 16/887,852, filed May 29, 2020, 12 pages.
Non-Final Office Action dated Jan. 17, 2023, for U.S. Appl. No. 17/837,900, filed Jun. 10, 2022, 12 pages.
Notice of Allowance dated Jul. 25, 2011, for U.S. Appl. No. 12/367,679, filed Feb. 9, 2009, 7 pages.
Notice of Allowance dated Apr. 9, 2014, for U.S. Appl. No. 13/895,255, filed May 15, 2013, 7 pages.
Notice of Allowance dated Oct. 27, 2015, for U.S. Appl. No. 14/278,973, filed May 15, 2014, 8 pages.
Notice of Allowance dated Mar. 27, 2013, for U.S. Appl. No. 13/209,275, filed Aug. 12, 2011, 9 pages.
Notice of Allowance dated Oct. 5, 2017, for U.S. Appl. No. 14/951,194, filed Nov. 24, 2015, 11 pages.
Notice of Allowance dated Apr. 4, 2019, for U.S. Appl. No. 15/807,383, filed Nov. 8, 2017, 11 pages.
Notice of Allowance dated Dec. 4, 2019, for U.S. Appl. No. 16/100,054, filed Aug. 9, 2018, 13 pages.
Notice of Allowance dated Apr. 10, 2020, for U.S. Appl. No. 16/033,125, filed Jul. 11, 2018, 18 pages.
Notice of Allowance dated Apr. 30, 2020, for U.S. Appl. No. 15/814,222, filed Nov. 15, 2017, 10 pages.
Notice of Allowance dated Jan. 12, 2021, for U.S. Appl. No. 16/425,416, filed May 29, 2019, 13 pages.
Notice of Allowance dated Feb. 22, 2021, for U.S. Appl. No. 16/818,325, filed Mar. 13, 2020, 7 pages.
Notice of Allowance dated Dec. 22, 2021, for U.S. Appl. No. 16/887,896, filed May 29, 2020, 11 pages.
Notice of Allowance dated Apr. 29, 2022, for U.S. Appl. No. 16/191,131, filed Nov. 14, 2018, 11 pages.
Notice of Allowance dated Jul. 12, 2022, for U.S. Appl. No. 17/238,113, filed Apr. 22, 2021, 9 pages.
Notice of Allowance dated Aug. 1, 2022, for U.S. Appl. No. 17/238,113, filed Apr. 22, 2021, 8 pages.
Notice of Allowance dated Dec. 15, 2022, for U.S. Appl. No. 17/203,532, filed Mar. 16, 2021, 8 pages.
Notice of Allowance dated Feb. 7, 2023, for U.S. Appl. No. 17/697,828, filed Mar. 17, 2022, 10 pages.
North Shore LIJ (2008). IMRT treatment plans: Dosimetry measurements & monitor units validation, 133 total pages.
Olivera, G.H. et al. (2000). "Modifying a plan delivery without re-optimization to account for patient offset in tomotherapy," Proceedings of the 22$^{nd}$ Annual EMBS International Conference, Jul. 23-28, 2000, Chicago, IL, pp. 441-444.
Papanikolaou, N. et al. (2010). "MU-Tomo: Independent dose validation software for helical tomo therapy," *J. Cancer Sci. Ther.* 2:145-152.
Parodi, K. (2015). "Vision 20/20: Positron emission tomography in radiation therapy planning, delivery, and monitoring," *Med. Phys.* 42:7153-7168.
Partial Supplementary European Search Report dated Jun. 25, 2015, for European Application No. 12 763 280.0, filed on Mar. 30, 2012, 6 pages.
Prabhakar, R. et al. (2007). "An Insight into PET-CT Based Radiotherapy Treatment Planning," *Cancer Therapy* (5):519-524.
Schleifring (2013). Slip Ring Solutions—Technology, 8 total pages.
Tashima, H. et al. (2012). "A Single-Ring Open PET Enabling PET Imaging During Radiotherapy," *Phys. Med. Biol.* 57(14):4705-4718.

TomoTherapy® (2011). TOMOHD Treatment System, Product Specifications, 12 total pages.
Varian Medical Systems (2004). "Dynamic Targeting™ Image-Guided Radiation Therapy—A Revolution in Cancer Care," *Business Briefing: US Oncology Review*, Abstract only, 2 pages.
ViewRay's MRIDIAN LINAC enables radiosurgery with MRI vision for cancer therapy, (2017). YouTube video located at https://www.youtube.com/watch?v=zm3g-BISYDQ, PDF of Video Screenshot Provided.
Wang, D. et al. (2006). "Initial experience of FDG-PET/CT guided IMRT of head-and-neck carcinoma," Int. J. Radiation Oncology Biol. Phys. 65:143-151.
Wikipedia (2016). "Scotch yoke," Retrieved from https://en.wikipedia.org/wiki/Scotch_yoke, 3 pages.
Willoughby, T. et al. (2012). "Quality assurance for nonradiographic radiotherapy localization and positioning systems: Report of task group 147," Med. Phys. 39:1728-1747.
Written Opinion of the International Searching Authority dated May 4, 2009, for PCT Application No. PCT/US2009/01500, filed on Mar. 9, 2009, 5 pages.
Written Opinion of the International Searching Authority dated Jul. 20, 2012, for PCT Patent Application No. PCT/US2012/031704, filed on Mar. 30, 2012, 10 pages.
Written Opinion of the International Searching Authority dated Mar. 7, 2018, for PCT Application No. PCT/US2017/061848, filed on Nov. 15, 2017, 5 pages.
Written Opinion of the International Searching Authority dated Oct. 2, 2018, for PCT Application No. PCT/US2018/041700, filed on Jul. 11, 2018, 19 pages.
Written Opinion of the International Searching Authority dated Oct. 24, 2018, for PCT Application No. PCT/US2018/046132, filed on Aug. 9, 2018, 7 pages.
Written Opinion of the International Searching Authority dated Mar. 13, 2018, for PCT Application No. PCT/US2017/061855, filed on Nov. 15, 2017, 6 pages.
Written Opinion of the International Searching Authority dated Jun. 20, 2018, for PCT Application No. PCT/US2018/025252, filed on Mar. 29, 2018, 12 pages.
Written Opinion of the International Searching Authority dated Jan. 30, 2019, for PCT Application No. PCT/US2018/061099, filed on Nov. 14, 2018, 11 pages.
Yamaya, T. et al. (2008). "A proposal of an open PET geometry," *Physics in Med. and Biology* 53:757-773.
Final Office Action dated Sep. 19, 2023, for U.S. Appl. No. 17/837,900, filed Jun. 10, 2022, 16 pages.
Non-Final Office Action dated Aug. 3, 2023, for U.S. Appl. No. 18/053,874, filed Nov. 9, 2022, 8 pages.
Notice of Allowance dated Jun. 30, 2022, for U.S. Appl. No. 16/582,286, filed Sep. 25, 2019, 10 pages.
Notice of Allowance dated Jul. 21, 2022, for U.S. Appl. No. 16/582,286, filed Sep. 25, 2019, 7 pages.
Corrected Notice of Allowability mailed on Jan. 30, 2024, for U.S. Appl. No. 16/887,852, filed May 29, 2020, 2 pages.
Extended European Search Report mailed on Jan. 24, 2024, for EP Application No. 23 160 060.2, filed Mar. 9, 2009, 12 pages.
Non-Final Office Action mailed on Dec. 13, 2023, for U.S. Appl. No. 18/056,188, filed Nov. 16, 2022, 7 pages.
Non-Final Office Action mailed on Jan. 16, 2024, for U.S. Appl. No. 18/178,431, filed Mar. 3, 2023, 16 pages.
Notice of Allowance mailed on Dec. 22, 2023, for U.S. Appl. No. 18/053,874, filed Nov. 9, 2022, 8 pages.
Notice of Allowance mailed on Dec. 28, 2023, for U.S. Appl. No. 16/887,852, filed May 29, 2020, 9 pages.
Notice of Allowance mailed on Feb. 7, 2024, for U.S. Appl. No. 18/311,134, filed May 2, 2023, 11 pages.

* cited by examiner

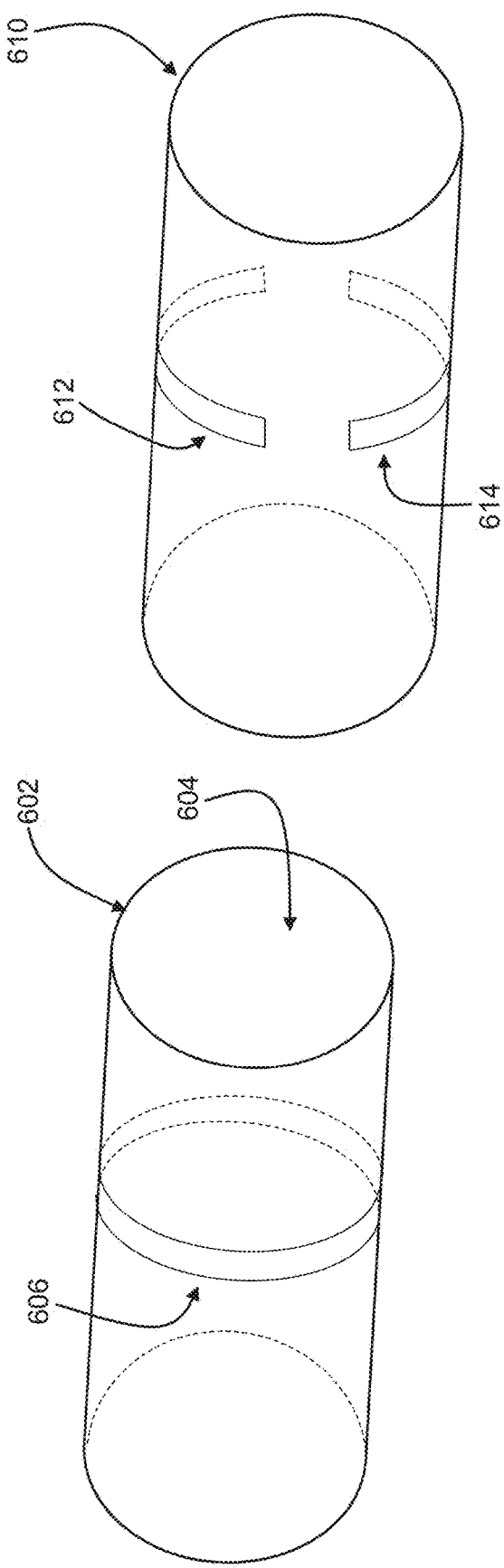
FIG. 6B
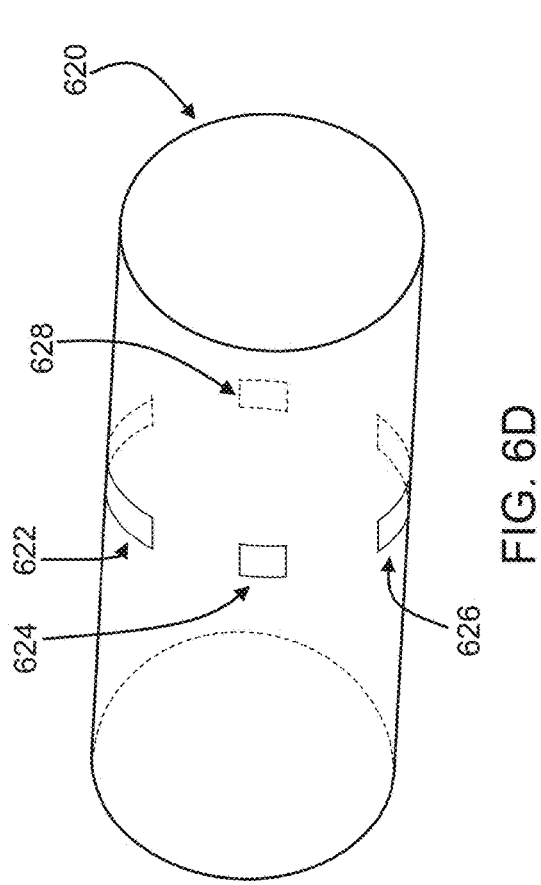
FIG. 6C
FIG. 6D

SYSTEMS AND METHODS FOR PATIENT MONITORING FOR RADIOTHERAPY

CROSS-REFERENCE TO RELATED APPLICATIONS

This application is a continuation of U.S. patent application Ser. No. 16/191,131, filed on Nov. 14, 2018, which claims priority to U.S. Provisional Patent Application Ser. No. 62/585,772, filed on Nov. 14, 2017, each of which are hereby incorporated by reference in their entirety.

TECHNICAL FIELD

This disclosure relates to devices and methods for acquiring image data of a patient within a bore of a radiation therapy system. Acquired patient images may be used to determine and/or monitor the location and/or position of a patient inside and outside the bore.

BACKGROUND

During a radiation treatment session, a patient is placed on a patient platform which moves the patient into a beam path or treatment plane of a therapeutic radiation source of a radiation therapy system. Radiation is applied to the patient in a prescribed manner based on a treatment plan. In many radiation therapy systems, both the patient platform and the therapeutic radiation source can move relative to each other so that radiation can be delivered to tumors while limiting radiation delivery to surrounding healthy tissue.

While the movement of the patient platform and/or other radiation therapy system components may be calculated or predicted in advance, patient movements are often difficult to predict. For example, patients may change their position on the platform voluntarily or involuntarily (e.g., breathing, fidgeting, shifting due to discomfort, etc.). Because treatment plans are calculated based on assumed patient position(s), location(s), and/or patient geometry (e.g., size, shape, etc.), patient movement can impact the quality and efficacy of a treatment session. For example, if radiation is applied without accounting for changes in patient position, location, and/or geometry relative to the therapeutic radiation source, radiation may be delivered to non-target regions and target regions may not receive the radiation dose prescribed by the treatment plan.

Typically, the position and/or location of a patient in a radiation therapy system is monitored using one or more cameras mounted on the walls or ceilings of the treatment system bunker. Images from these cameras may be viewed by a practitioner to identify any large changes in position and/or location. However, depending on the geometry of the radiation therapy system, views of the patient may be obstructed. For example, the robotic arms or partial ring gantry or full-ring gantry may prevent a camera from acquiring a clear view of the patient. Some systems include a camera that is mounted at the foot of the patient platform. In some radiation therapy systems, the therapeutic radiation source may be located within a bore, and as the patient is moved deeper into the bore, ceiling and/or wall-mounted cameras are less able to provide a clear view of the patient. As such, improvements to monitoring changes in patient position and/or location are desirable.

SUMMARY

Disclosed herein are systems and methods for real-time monitoring of patient position and/or location during a radiation treatment session. Images acquired of a patient during a treatment session may be used to calculate the patient's position and/or location with respect to the components of the radiation therapy system. Depending on the characteristics of the changes in patient position and/or location, the radiation therapy system may determine whether to adjust radiation delivery. Real-time monitoring of patient position and/or location may confirm that the patient is correctly positioned (e.g., set up) at the start of a treatment session and throughout the duration of the treatment session. Patient position and/or location information calculated from image data acquired during the treatment session may also help prevent collisions between the patient and components of the radiation therapy system. Some of the radiation therapy systems described herein may comprise a controller that is configured to generate a patient 3-D model (e.g., full or partial 3-D model) and/or patient 2-D surface throughout the duration of a treatment session based on the images acquired during the treatment session. While the examples described herein may refer to generating a 3-D patient model, it should be understood that similar methods and/or devices may be used to generate a 2-D patient surface.

One variation of a radiation therapy system may comprise a rotatable gantry having a longitudinal bore therethrough, and a patient-monitoring imaging system comprising one or more sensors (such as a camera or any image detector) that may be attached to the rotational gantry within the bore. The sensors may acquire image data as the gantry rotates and may generate a 360° view of the patient. Image data from the one or more sensors may be used to calculate the current location of a patient relative to radiation therapy system components and to compare the current location of a patient with previous patient locations (e.g., from previous scans or session, from earlier in the same treatment session, etc.). For example, image data may be used to register the patient in the same coordinate system as the radiation therapy system. Image data may also be used to detect undesirable patient movement during a radiation treatment session, diagnostic CT or localization CT scan (e.g., any one or more imaging modalities used to acquire one or more treatment planning images). Patient position and/or location data acquired by the rotating sensors that are located within the bore region of the radiation therapy system may be used to confirm patient position before and during radiation treatment sessions to help reduce setup variations and facilitate delivery of the prescribed radiation dose to tumor regions. Patient position and/or location data may optionally be used to help guide movement of the patient platform and/or generate a notification of any possible patient-system collisions.

One variation of a radiation therapy system may comprise a circular gantry comprising a stationary frame and a rotatable ring coupled to the stationary frame, a therapeutic radiation source coupled to the rotatable ring, an optical imaging system coupled to the rotatable ring, wherein the optical system is configured to acquire images of a patient area during rotation of the ring, and a controller in communication with the optical imaging system, wherein the controller is configured to process the acquired images to calculate information relating to the radiation therapy system. The optical imaging system may comprise an image sensor having a field-of-view. The image sensor may be located adjacent to the therapeutic radiation source. Alternatively or additionally, the optical imaging system may further comprise an emission source located on the rotatable ring and configured to illuminate the field-of view of the image sensor. The therapeutic radiation source may have a treatment plane defined by its field-of-view and the optical imaging system may have an imaging plane defined by its field-of-view, and the treatment plane may be coplanar with the imaging plane or may be distinct from the imaging plane. The optical imaging system may comprise a laser profiler, and/or a time-of-flight reflectometer, and/or a monoscopic or stereoscopic camera. In some variations, the optical imaging system has a field-of-view that includes the patient area that is outside of the bore. The optical imaging system may be located within the bore and may have a field-of view that includes the patient area that is inside the bore.

In some variations, the rotatable ring may be configured to rotate at a rate of at least about 10 RPM, and may be configured to rotate at a rate of at least about 60 RPM and even up to 200 RPM. The rotatable ring may define a longitudinal bore and the optical system may be located within the bore. The system may further comprise a housing disposed over the circular gantry where the housing may comprise a longitudinal lumen that corresponds with the bore and may comprise a light-transmitting region along an inner surface of the housing that corresponds with a field-of-view of the optical imaging system. The light-transmitting region is a strip along an inner circumference of the bore, and/or may comprise two or more windows located along an inner circumference of the bore. The system may comprise a patient platform that is movable within the patient area.

In some variations, the controller may be configured to generate a 3-D model of a patient within the patient area at a specified time interval using images acquired at the specific time interval. The controller may be configured to compare the 3-D model of the patient at the specified time interval and a 3-D model of the patient at an earlier time interval to identify a positional difference in the 3-D models. For example, the identified positional difference in the 3-D models may correspond with the patient's respiratory cycle and optionally, the controller may be configured to identify the portion of the respiratory cycle with which the identified difference corresponds and may cease activation of the therapeutic radiation source if the identified portion of the respiratory cycle does not match with a predetermined activation portion of the respiratory cycle. Alternatively or additionally, the controller may be configured to compare the identified difference in the 3-D models with a predetermined movement threshold and to cease activation of the therapeutic radiation source if the identified difference exceeds the movement threshold. The controller may be configured to identify surface points on the patient 3-D model and to track the position of the identified surface points over time. The controller may be configured to generate a 3-D model of the patient platform and to compare the generated 3-D model of the patient platform with a reference 3-D model of the patient platform to calculate a deviation from the reference 3-D model. The reference 3-D model of the patient platform may be a 3-D model of the patient platform generated before the patient is loaded on the platform. The controller may adjust the position of the patient platform to compensate for the calculated deviation. Optionally, the controller may be configured to generate a surface model of the patient at a specified time interval using images acquired at the specific time interval.

In some variations, the controller may be configured to compare the identified difference in the 3-D models with a motion envelope and to generate a notification if the identified difference exceeds the motion envelope. The motion envelope may be determined based on whether the therapeutic radiation source is emitting radiation, and the motion envelope may have a first range of motion when the therapeutic radiation source is not emitting radiation and a second range of motion when the therapeutic radiation source is emitting radiation, e.g., the first range of motion may be greater than the second range of motion. Alternatively or additionally, the motion envelope may be determined based on whether a patient platform movable within the patient region is moving or stationary, and motion envelope may have a first range of motion when the patient platform is moving and a second range of motion when the patient platform is stationary, e.g., the first range of motion may be greater than the second range of motion.

In some variations, the controller may be configured to calculate a range of motion of a patient located on the patient platform based on the acquired image data. Some systems may comprise a display and the controller may be configured to output a graphic representing the calculated range of motion to the display. The controller may be further configured to compare the calculated range of motion with a motion envelope and to generate a notification if the calculated range of motion exceeds the motion envelope. For example, the motion envelope may be determined based on whether the therapeutic radiation source is emitting radiation, and the motion envelope has a first range of motion when the therapeutic radiation source is not emitting radiation and has a second range of motion when the therapeutic radiation source is emitting radiation, e.g., the first range of motion may be greater than the second range of motion. The motion envelope may be determined based on whether the patient platform is moving or stationary, and the motion envelope has a first range of motion when the patient platform is moving and has a second range of motion when the patient platform is stationary, e.g., the first range of motion may be greater than the second range of motion.

In some variations, the controller is configured to process the acquired images to calculate information relating to the radiation therapy system, and the information may comprise positional information of a patient within the patient area. The system may comprise a patient platform that is movable within the patient area, and the controller may be configured to calculate a difference between positional information of the patient at a specified time point and reference positional information of the patient, and calculate a set of patient platform adjustments that compensate for the patient positional information difference. The controller may be further configured to move the patient platform in accordance with the calculated set of patient platform adjustments. The controller may be configured to compare positional information of the patient and positional information of the rotatable ring and to generate a notification if an overlap is detected between patient positional information and rotatable ring positional information. In some variations, the information relating to the radiation therapy system comprises positional information of the patient platform and/or positional information of a patient positioning device located in the patient area.

Some variations of a patient and/or system monitoring imaging system may comprise an optical detector comprising a plurality of sensor pixels, and the controller may be configured to calibrate the optical detector by identifying faulty sensor pixels and to generate a notification when a faulty sensor pixel is identified. Identifying faulty sensor pixels may comprise recording output signals from each sensor pixel, calculating a difference between the output signal of each sensor pixel and its respective expected output signal, and tagging a sensor pixel as faulty if its calculated difference exceeds its respective pixel error threshold. The pixel error threshold for each sensor pixel may include a maximum acceptable pixel intensity difference. Calculating a difference between the output signal of each sensor pixel and its respective expected output signal may comprise calculating a difference between noise levels of the output signal of each sensor pixel with a threshold noise levels, and the pixel errors threshold may include a maximum acceptable pixel noise level. The controller may be further configured to substitute the output signal of an identified faulty sensor pixel with a signal derived by interpolating output signals of non-faulty sensor pixels located within a predetermined distance from the identified faulty sensor pixel. Optionally, any of the systems described herein may comprise a calibration phantom with predetermined dimensions and having one or more surface contour indicia with predetermined 3D geometric markings having predetermined width, height and length values. For example, at least one of the patient platform, a portion of the patient area, and a calibration phantom may have at least one calibration reference marking that has one or more predetermined width, and/or height, and/or length values.

Alternatively or additionally, the controller may be configured to calculate a pixel degradation rate for each sensor pixel by calculating changes in the calculated difference of each sensor pixel output signal over a specified interval of time, and to generate a detector replacement notification if the pixel degradation rate exceeds a threshold degradation rate. For example, calculating the pixel degradation rate may comprise generating a regression model using the calculated changes of each sensor pixel over the specified interval of time to generate a prediction of a time duration when each sensor pixel will exceed its respective pixel error threshold.

Also described herein are methods for generating a 3-D patient model. One variation of a method may comprise positioning a patient on a patient platform of a radiation therapy system, the radiation therapy system further comprising a circular gantry having a rotatable ring about a bore, a therapeutic radiation source coupled to the rotatable ring, and an optical imaging coupled to the rotatable ring inside the bore, acquiring 2-D images of the patient and the patient platform using the optical imaging system while rotating the optical imaging system, generating a 3-D model of the patient and the patient platform using the acquired 2-D images, and generating a 3-D model of the patient by subtracting a pre-calculated 3-D model of the patient platform from the generated 3-D model of the patient and the patient platform. The patient platform may be movable within a patient area that is at least partly located within the bore. Acquiring 2-D images may comprise acquiring 2-D images during at least one rotation of the ring about the patient area and may optionally comprise acquiring 2-D images at four or more pre-defined locations about the patient area. The 3-D model of the patient platform may be calculated based on position sensor data and patient platform geometry. Generating a 3-D model of the patient and the patient platform may comprise depth-sensing methods, such as stereovision methods, and/or laser scanning or triangulation methods, and/or time-of-flight methods, and/or projected light methods.

Also disclosed herein are methods for generating a collision notification for a radiation therapy system. One variation of a method may comprise deriving a 3-D model of a rotatable ring of a radiation therapy system based on positional sensor data, generating a 3-D patient model using any of the methods described above, comparing the generated 3-D patient model with the 3-D model of the rotatable ring to determine a location of the patient relative to the rotatable ring, and if the generated 3-D patient model is located within a pre-determined safety margin of the 3-D model of the rotatable ring, generating a notification to alert an operator of the radiation therapy system. The method may further comprise generating a notification to stop motion of the patient platform if the generated 3-D patient model is located within a pre-determined collision margin of the 3-D model of the rotatable ring. The generated 3-D patient model is a partial 3-D patient model that includes patient position data acquired from a subset of circumferential locations about the patient area.

BRIEF DESCRIPTION OF THE DRAWINGS

FIG. 6B provides a partial perspective view of one variation of a bore of a radiation therapy system housing.

FIG. 6C provides a partial perspective view of one variation of a bore of a radiation therapy system housing.

FIG. 6D provides a partial perspective view of one variation of a bore of a radiation therapy system housing.

DETAILED DESCRIPTION

Figure 1:
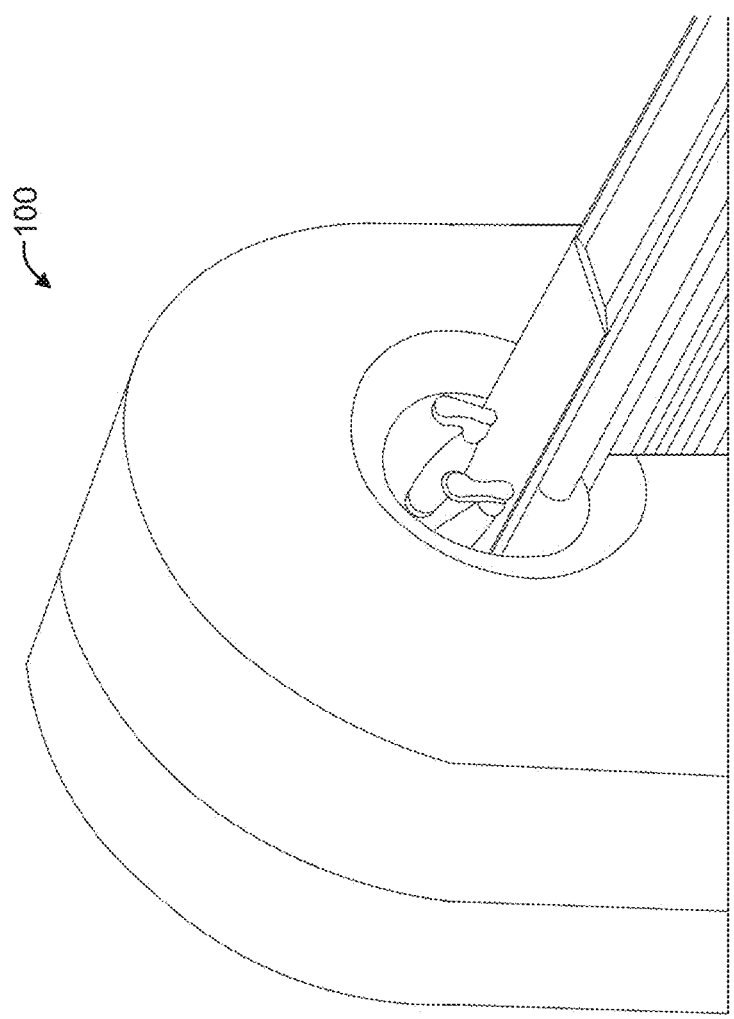
FIG. 1 is a perspective view of one variation of a radiation therapy system.

Described herein are systems and methods for monitoring the position and/or location of a patient inside and/or outside a bore of a radiation therapy system. The systems and methods disclosed herein may also be used for calculating information relating to the radiation therapy system A radiation therapy system may comprise a gantry rotatable about a bore having an interior volume, a therapeutic radiation source coupled to the rotatable gantry, a patient platform that is movable within the interior volume of the bore, and a patient-monitoring imaging system coupled to the rotatable gantry such that the imaging system has a field-of-view that includes at least a portion of the volume of the bore and acquires image data as the gantry rotates. The patient-monitoring imaging system may comprise an optical imaging device such as a camera. The sensors or camera of the patient-monitoring imaging system may be mounted on the rotatable gantry in a bore region of the radiation therapy system. In some variations, the entire field-of-view of the patient-monitoring imaging system may be within the bore volume, while in other variations, the field-of-view of the imaging system may include both the interior volume of the bore and a region located outside of the bore. Alternatively, the field-of-view of the patient-monitoring imaging system may include only a region outside of the bore. A radiation therapy system may also comprise a housing disposed over the rotatable gantry such that the volume of the bore is bounded by an exterior portion of the housing. The image data acquired by the imaging system may be used to calculate information relating to the radiation therapy system. Examples of information relating to the radiation therapy system and/or information that may be calculated based on image data acquired by the monitoring imaging system may include, but are not limited to, patient positioning device position relative to the therapy system components, patient position and/or motion relative to the therapy system components, patient platform position, and the like.

Some radiation therapy systems may comprise a non-rotating patient-monitoring imaging system. The stationary patient-monitoring imaging system may be coupled to the exterior portion of the housing instead of the rotatable gantry on which the therapeutic radiation source is mounted. For example, the imaging system may be located on the exterior portion of the housing at the edge of the bore and have a field-of-view that includes a region outside of the bore (e.g., at the top or 12:00 position) and/or a bore volume. The stationary patient-monitoring imaging system may be located on the exterior portion of the housing within the bore (or along the length of the bore) such that the imaging system has a field-of-view that includes the bore volume. For the purposes of this document, a patient-monitoring imaging system with a sensor located in the bore and/or rotatable above the bore volume may be referred to as an in-bore imaging system.

Patient-monitoring imaging systems for any of the radiation therapy systems described herein may comprise imaging devices of different imaging modalities. In some variations, the imaging system may comprise an optical imaging device, such as one or more light emitters (e.g., emitting light in the visible spectrum, infrared wavelength range, and/or UV wavelength range), such as scanning lasers (e.g., laser profiler), and/or time-of-flight reflectometers, and/or monoscopic or stereoscopic cameras, optical detectors having one or more CCD sensors and/or CMOS sensors, and the like. Alternatively or additionally, imaging systems may comprise ultrasound systems, and/or X-ray systems, and/or CT systems, and/or terahertz and backscatter X-ray imaging systems, and the like. Other types of imaging devices that may be included in any of the patient-monitoring imaging systems described herein include infrared cameras, video cameras with speckle patterns, radiofrequency (RF) tracking systems comprising a transponder and receiver, projection cameras, ultrasonic transmitter (e.g., an ultrasonic transmitter array) and ultrasonic range sensor, a laser displacement sensor having an emitter and a sensor head, any range-measuring system, and the like. While the variations and features described below and depicted in the drawings relate to an optical imaging system, it should be understood that any one or more of the features and methods described herein may pertain to any other imaging modality or system, such as any non-ionizing imaging modality comprising one or more of the imaging devices listed above.

Also described herein are methods for generating 3-D models of a patient (and any patient-positioning devices or accessories) and/or determining the location and/or position of the patient relative to the components of the radiation therapy system. Some methods may comprise comparing a 3-D model generated during an imaging or treatment session with a 3-D model generated during patient set up (e.g., just before the session) to confirm that the patient has not deviated substantially from the initial set up position. Some methods may also determine whether the patient is on "collision course" with any components of the radiation therapy system, and generate a notification to inform the operator of any possible collision. For example, a method may comprise comparing the location and/or position of a patient with the location of the radiation therapy system components and generating a notification if the location and/or position of the patient is within a pre-determined safety margin of the radiation therapy system. A patient 3-D model may be compared with a machine 3-D model to define a patient platform motion allowance or envelope within which the platform may move without contacting the patient to any radiation therapy system components.

The motion allowance or envelope may vary depending on the position and/or motion of the patient platform. The patient platform may be configured to continuously move through the treatment plane while therapeutic radiation is emitted to the patient, and/or may be configured to stopped in the treatment plane at a discrete location while therapeutic radiation is emitted to the patient. In the latter variation, the therapeutic radiation emission may be paused while the patient platform is moved to the next discrete location and may resume radiation emission after the platform is stopped at the next discrete location. Such discrete stepping of the patient platform through the treatment plane may be referred to as beam station delivery, where therapeutic radiation is emitted when the patient platform is stopped at one of a plurality of beam stations during a treatment session. The motion allowance or envelope may be smaller or tighter when the platform is stopped as compared to when the platform is moving. Additionally or alternatively, the motion allowance or tolerance may be smaller during therapeutic radiation emission as compared to when therapeutic radiation is paused. In the variation where radiation may be delivered to the patient while the patient platform moves continuously through the treatment beam (e.g., helical delivery), the same motion allowance or tolerance may apply throughout the treatment session. Optionally, if the speed of the patient platform varies during a treatment session, the motion allowance may also vary during the treatment session. For example, the motion allowance or tolerance may increase as the speed of the platform increases, and the motion allowance or tolerance may decrease as the speed of the platform decreases. If the patient position or motion exceeds the motion envelope and/or acceptable range of motion, a notification (e.g., a visual or graphical output to the system display and/or an audio output) may be generated to alert the clinician. If the patient position and/or motion calculated based on the acquired image data indicates a significant change (e.g., on the order of a quarter of a body length or more, motions consistent with the patient getting off the platform, high-frequency motion suggestive of involuntary muscle motion or a seizure), the therapy system may automatically pause radiation delivery until the clinician can confirm the state of the patient.

In some variations, the optical image device may acquire a greater quantity of image data when the platform is stopped, which may facilitate the precise detection of patient motion, and may acquire a smaller quantity of image data when the platform is moving. Optionally, the system may be configured to allocate computational resources or processor bandwidth to the calculation of a patient 3-D model when therapeutic radiation is paused (e.g., while the patient platform is moving between beam stations), which may result in a high-resolution 3-D model. During the emission of therapeutic radiation (e.g., while the patient platform is stopped at a beam station), computational resources may be prioritized for controlling and monitoring the therapeutic radiation source, and a portion of the remaining computational resources may be allocated for calculating a low-resolution 3-D model.

The patient-monitoring systems and methods described herein may facilitate precise and dynamic monitoring of patient position and location. For radiation therapy systems having a bore or tunnel through which a patient may be moved in the course of a radiation session, it may be challenging to monitor the patient using imaging devices mounted on the ceiling and/or wall of the radiation therapy system bunker. The field-of-view of these bunker-mounted imaging devices may not include a significant portion of the internal volume of the bore, and therefore, the ability to monitor the location and/or position of a patient inside the bore may be limited, especially as the patient is moved deeper into the bore or tunnel and is obscured by the housing of the radiation therapy system. The inability to view the patient is especially pronounced for therapy systems that have long bores (e.g., having a length of over about 100 cm, or over about 120 cm, or over about 150 cm) and/or have closed bores. An example of such a radiation therapy system (100) is depicted in FIG. 1. Even placing an imaging device such as a camera in the plane of the patient platform or couch top would still have a restricted view and have limitations detecting patient movement (e.g., limited monitoring of respiratory motion). The radiation therapy systems described herein comprise a patient-monitoring imaging system that is mounted on the radiation therapy system itself, and comprises one or more sensors (e.g., detectors) that have a field-of-view that includes the interior volume of the bore. In some variations, the imaging system may be rotatable and/or may be mounted on the same gantry as the therapeutic radiation source. Alternatively or additionally, the imaging system may be mounted on the portion of the housing that forms the sidewalls of the bore. In-bore imaging systems mounted on a gantry or housing of a radiation therapy system having a field-of-view that includes at least a portion of the internal volume of the bore may be configured to acquire image data sufficient for extracting patient respiratory information and/or deriving a 3-D model of the patient. Image data may be acquired before, during and/or after the treatment session (i.e., before the first radiation pulse, during the emission of radiation pulses, and/or after the last radiation pulse). Dynamic or real-time patient, location, and/or geometry data may facilitate the localization workflow, as the operator is not limited to a fixed patient platform margin for localization. Instead, the patient platform limits for localization may be based on the real-time/dynamic patient position and geometry, and hence, may also provide more confidence to the operator to make the corrections remotely. Optionally, reflective fiducials may be placed on the patient to help facilitate tracking by the imaging system.

Systems

A radiation therapy system may comprise a circular gantry having a stationary frame and a rotatable ring coupled to the stationary frame, a therapeutic radiation source coupled to the rotatable ring, and an imaging system configured to acquire image data of a patient during a treatment session. The rotatable ring may have a circumference and a longitudinal length (e.g., parallel to its axis of rotation). The therapeutic radiation source may be mounted at a specified circumferential location and a specified longitudinal location. Circumferential locations may be designated, for example, by an angle from about 0 degrees to about 360 degrees, where the 0°/360° position is at the top of the gantry (e.g., the 12:00 position) and the 180° position is at the bottom of the gantry (e.g., the 6:00 position). The longitudinal location may be specified as a distance from an edge of an opening of the ring, for example, if the length of the rotatable ring is $L_R$, a longitudinal location may be designated as a distance from about 0 units to about $L_R$ units from the edge. A patient treatment region may comprise a bore that extends along the length of the rotatable ring (e.g., along IEC-Y axis), around which the ring rotates. Similar to the rotatable ring, the bore may also have a bore longitudinal length and a bore circumference. The length of the bore may correspond to the length of the rotatable ring and/or may be longer than the length of the ring. The radiation therapy system may further comprise a patient platform that is movable within the bore of the patient treatment region. The radiation therapy system may further comprise a housing that encloses the circular gantry and the therapeutic radiation source in an internal volume of the housing. The surface of the housing may form the sidewalls of the bore, and may, for example, circumscribe the bore forming a tunnel through which the patient platform may be moved during a patient scan and/or treatment session. Optionally, the radiation therapy system may comprise one or more PET detectors and/or a kV CT imaging system.

The patient-monitoring imaging system may comprise one or more sensors or cameras of a variety of imaging modalities that are mounted on the gantry or housing of the radiation therapy system. A patient-monitoring imaging system may comprise infrared, visible, and/or ultraviolet light sensors (e.g., optical detectors having one or more CCD sensors and/or CMOS sensors), ultrasound sensors, radar sensors such as terahertz sensors (from about 100 GHz to about 800 GHz), MRI sensors, and/or x-ray detectors (e.g., configured to detect backscattered x-rays and/or low intensity x-rays). Imaging systems may, for example, comprise one or more time-of-flight reflectometers, and/or one or more monoscopic stereoscopic cameras. A patient-monitoring imaging system may comprise an infra-red laser profiler, which may include a camera which may be used in conjunction with a linear scanner to generate 3-D patient profile (e.g., Ultra-High Speed In-line Profilometer LJ-V7000 series by KEYENCE©). An imaging system may comprise one or more light emitters located on the gantry or housing such that the emitted light illuminates a patient (and any patient positioning devices) within the bore of the therapy system and one or more light detectors or cameras located on the gantry or housing to measure the light that is reflected and/or transmitted through the patient (and any patient positioning devices). The imaging system may be configured to acquire image data using structured light surface mapping. An imaging system configured for structured light scanning may comprise one or more emitters that project a pattern of light on the patient (e.g., stripes and/or a grid) and one or more cameras or detectors or sensors that capture the distortion of the pattern of light on the patient. The data from the one or more cameras or detectors located at various locations about the patient treatment area or bore may be transmitted to a controller or processor that reconstructs the surface of the patient using laser scanning or triangulation methods. The one or more emitters may emit light of any desired wavelength, including infrared light, and/or red light, and/or green light and/or blue light, and/or white light, etc. Other types of imaging devices that may be included in any of the patient-monitoring imaging systems described herein include infrared cameras, video cameras with speckle patterns, radiofrequency cameras, projection cameras, and the like. Imaging devices may comprise sensors (e.g., amorphous silicon (a-Si) sensors) that are radiation hard and/or able to operate in the presence of elevated levels of ionizing radiation. A patient-monitoring imaging system may comprise a controller for processing image data acquired by the one or more sensors or cameras. The controller may be in communication with the one or more sensors via one or more data buses or wires. The patient-monitoring controller may be the same as the radiation therapy system controller or may be a separate controller, as may be desirable. The patient-monitoring system controller may comprise one or more memories that are configured to store raw and/or processed image data as well as patient and machine models.

In some variations, a radiation therapy system may comprise one or more patient-monitoring imaging systems coupled to the rotatable ring of the circular gantry and configured to acquire patient image data while the ring is rotating (e.g., during a imaging and/or treatment session). In some variations, the therapeutic radiation source and the patient-monitoring imaging system may both be mounted on the rotatable ring, while other variations may have multiple rotatable rings and the therapeutic radiation source and imaging system may be mounted on separate rotatable rings. Each rotatable ring may define a rotational plane, and the rotational planes of the separate rings may be coplanar or may not be coplanar. A patient-monitoring imaging system of the radiation therapy system may be mounted at any longitudinal location and/or any circumferential location on the rotatable ring. In some variations, a rotatable patient-monitoring imaging system may be located at the same circumferential location as the therapeutic radiation source, but at a different longitudinal location (which may be described as the patient-monitoring imaging system being non-coplanar with the therapeutic radiation source). In other variations, the patient-monitoring imaging system may be located at a different circumferential location as the therapeutic radiation source, but at the same longitudinal location (which may be described as the patient-monitoring imaging system being coplanar with the therapeutic radiation source). Alternatively, the patient-monitoring imaging system may be located at a different circumferential location and longitudinal location from the therapeutic radiation source. The circumferential location of the imaging system relative to the therapeutic radiation source may be selected to help reduce the exposure of the imaging system sensors to ionizing radiation from the radiation source. For example, the imaging system may be located at the same circumferential location as the therapeutic radiation source so that the radiation beams emitted by the radiation source are directed away from the imaging system. Imaging systems with radiation-hard or radiation-robust sensor elements may be located at regions of elevated radiation levels (e.g., opposite a therapeutic radiation source or about 180 degrees from a therapeutic radiation source) while imaging systems with radiation-sensitive or radiation damage-prone sensors may be located at regions with lowered radiation levels (e.g., at the same circumferential location as a therapeutic radiation source). While the examples of radiation therapy systems described and depicted herein show a single patient-monitoring imaging system, radiation therapy systems may have a plurality of imaging systems located at various circumferential and longitudinal locations along a gantry ring or bore. The imaging systems may be mounted on a common gantry or may be mounted on separate gantries (e.g., gantries that may be moved independent of each other). For example, the radiation therapy system may have a first rotatable gantry and a second rotatable gantry that is separate from the first rotatable gantry and the therapeutic radiation source may be mounted to the first gantry while the imaging system may be mounted to the second gantry. The axes of rotation for the first and second gantries may be collinear.

Several system parameters may affect the quality and quantity of acquired imaging data, and such parameters may be adjusted in order to ensure a sufficient quantity of imaging data is acquired for generating 3-D patient models or 2-D patient surface renderings in real-time. Examples of parameters may include (1) the gantry rotation rate; (2) the number of imaging sensor (for example, placed 90 or 180° apart to effectively double or quadruple the acquisition rate); (3) the IEC-Y field-of-view (FOV) of the imaging sensor; (4) the couch-top velocity; (5) the number beam stations and/or the spacing between each beam station. For example, a patient-monitoring imaging system for a radiation therapy system with a slower rotating gantry (e.g., less than about 30 RPM, less than about 20 RPM, less than about 10 RPM) may comprise a patient-monitoring imaging system with a longer IEC-Y FOV imaging sensor or may comprise a plurality of imaging sensors with a relatively shorter IEC-Y FOV (e.g., such that their cumulative FOV approximates the FOV of an imaging sensor with a relatively longer IEC-Y FOV). In some variations, a patient-monitoring imaging system may be used to check patient positioning and breathing during a CT scan. A CT scan typically involves breath-hold techniques to help reduce motion artifacts (especially for CT scans of the chest region), where typical breathing has frequency components between 0.1 Hz to 0.3 Hz. For a gantry capable of rotating at a speed of about 60 RPM, a patient-monitoring imaging system comprising a single sensor or camera with an IEC-Y FOV twice than the table travel distance per rotation may acquire sufficient imaging data to capture patient position and confirm proper breathing. For example, rotating an imaging system optical sensor at about 60 RPM or faster may allow for the acquisition of image data to detect patient position changes or uncontrolled breathing. A radiation therapy system comprising a gantry rotating at a slower rate (e.g., about 10 RPM, about 15 RPM, about 20 RPM, about 30 RPM) may comprise an imaging system having two sensor(s) or camera(s) that are mounted across from each other (e.g., about 180° apart), or orthogonal to each other (e.g., about 90° apart), which increases the effective frame rate to capture patient breathing motion similar to a single-sensor imaging system rotating at about twice the rate. Rotating the sensor(s) or camera(s) of an imaging system may allow for the acquisition of image data for confirming patient movement and generating 3-D patient models. Patient 3-D models in real-time may help to mitigate artifacts encountered in 2-D images (and/or images acquired by an imaging system located outside of the radiation therapy system bore), artifacts such as parallax error, limited patient treatment area or bore views, affects from ambient light, contrast variation, limited depth of focus and/or target contrast distortions.

The system may be configured to analyze or process image data to generate 3-D models (e.g., surface models or volumes) and/or measure patient and/or couch motion at varying degrees of precision at various times during a treatment session. For example, patient location, motion, and/or geometry data may be calculated with a greater degree of accuracy and precision when the therapeutic radiation source is emitting radiation (e.g., beam-on) than when the therapeutic radiation source is not emitting radiation (e.g., beam-off). In some variations, the system controller may be configured to generate a high-resolution and/or high-precision 3-D model during beam-off periods of time, and during beam-on, to calculate the incremental changes from the high-resolution 3-D model (e.g., motion, location, and/or geometry changes). During beam-on, the imaging system may continue to acquire image data but the controller may not use this data for 3-D model generation (which may be computationally intensive) and may instead use this data for monitoring motion and/or positional changes (which may be less computationally intensive than generating a 3-D model). This may help to relieve the computational load on the controller during beam-on, when computational resources (e.g., controller processor bandwidth) may be allocated for monitoring and controlling radiation emission from the therapeutic radiation source. Motion and/or position data calculated during beam-on may be compared with a predetermined motion envelope that includes a range of motion deemed acceptable during the delivery of radiation and/or may be calculated based on 3-D models and/or image data of the patient taken during the acquisition of treatment planning images. The acceptable motion envelope and/or range of motion during radiation delivery may be specified on a per-patient, per-clinician, and/or per-clinic basis. As described herein, the acceptable motion envelope may vary depending on whether the therapeutic radiation source is emitting radiation or not, and/or whether the patient platform is moving or not. At beam-off, those computational resources may then be shifted back to generating 3-D models and/or high-precision calculations using the acquired image data. Optionally, the controller may be configured to receive user input regarding the quality (e.g., resolution, precision, etc.) of the 3-D model such that higher or lower quality models may be generated as desired. The system may optionally comprise a display, and the motion envelope and/or range of motion and/or 3-D models and/or image data may be graphically represented on the display.

A rotatable patient-monitoring imaging system may be mounted at a longitudinal location of the rotatable ring such that the cumulative field-of-view (FOV) over all of the sensors or cameras is entirely within the internal volume of the bore (i.e., does not extend outside of the bore). For example, the imaging system may be mounted on the rotatable ring or housing in a central portion of the bore (e.g., where the longitudinal length of the bore is $L_B$, the longitudinal location may be $L_B/2$) and/or may be longitudinally offset from the location of the therapeutic radiation source. The cumulative FOV of the patient-monitoring imaging system may not overlap with a portion of the irradiation field of the therapeutic radiation source. Alternatively, the cumulative FOV of the patient-monitoring imaging system may overlap with a portion of the irradiation field of the therapeutic radiation source. For example, in some variations, about half of the cumulative FOV of the patient-monitoring imaging system may overlap with the irradiation field of the therapeutic radiation source. The proportion of the irradiation field that overlaps with the FOV of the patient-monitoring imaging system may be about 50% or more. In some variations, the FOV of the patient-monitoring system may be at least twice as large as the irradiation field of the therapeutic radiation source.

Alternatively or additionally, a rotatable imaging system may be mounted on the rotatable ring at or near the longitudinal location of an edge or opening of the bore. For example, an imaging system may be mounted on the rotatable ring at a longitudinal location that is just within the bore or just outside the bore. In some variations, an imaging system may be located at or near a bore opening, at the edge of the bore opening. The cumulative FOV of a patient-monitoring imaging system that is mounted at the periphery of a bore (either just inside or just outside the bore opening) may include regions that are within the bore volume and regions that are outside of the bore. For example, an imaging system may be mounted on the rotatable ring at a longitudinal location such that about half of the FOV of the imaging system is within the bore and about half of the FOV is outside of the bore. Alternatively, the FOV of the patient-monitoring imaging system may be mostly within the bore (e.g., about 60% or more, about 70% or more, about 85% or more, about 90% or more, about 95% or more, about 99% or more) or mostly outside of the bore (e.g., about 60% or more, about 70% or more, about 85% or more, about 90% or more, about 95% or more, about 99% or more).

One or more regions of the radiation system housing may be transparent or translucent, allowing for the passage of light, so that an optical patient-monitoring imaging system mounted on the rotatable gantry enclosed within the housing can acquire images of the patient, platform and/or patient positioning devices within the bore volume (e.g., the patient treatment region). The portions of the housing that are transparent or translucent may correspond to the movement trajectory of the sensors or cameras of the patient-monitoring imaging system. For example, in a radiation therapy system having an optical patient-monitoring imaging system mounted on a rotatable ring of a circular gantry enclosed in a housing, the movement trajectory of the one or more cameras may include at least a portion of the circumference of the bore. For a continuously rotating gantry, the one or more cameras may acquire image data from around the entire circumference (i.e., 0°-360°) of the bore. Alternatively, for a limited-rotating gantry where the gantry may move in arcs that are a subset of the entire circumference (e.g., arcs that span from about 0° to about 180°, arcs that span from about 0° to about 270°, etc.), the one or more cameras may acquire image data at positions along the arc. A radiation therapy system comprising an optical imaging system mounted on a rotatable gantry may comprise a housing having a transparent portion or window that wraps around at least a portion of the circumference of the bore. The location, size, and shape of the transparent portion or window may correspond to the movement trajectory of the optical imaging system as it rotates with the gantry, as well as the field-of-view of the optical imaging system. For example, the transparent portion of the housing may circumscribe the bore of a radiation therapy system, which may be preferred in a system with a continuously rotatable bore. Alternatively, the transparent portion of the housing may extend along an arc along the bore that corresponds to the arc trajectory of the rotatable gantry. In some variations, the transparent portion of the housing may correspond to predetermined locations at which the cameras of the patient-monitoring imaging system acquire images. While patient-monitoring imaging systems may be configured to continuously acquire image data while the ring of the circular gantry rotates (e.g., may comprise a high-bandwidth and/or high-data rate bus to transfer the acquired image data to a controller processor), imaging systems may also be configured to acquire image data at pre-determined or select gantry locations. For example, an imaging system may be configured to acquire image data when the one or more sensors or cameras are located at four circumferential locations (e.g., 0°/360°, 90°, 180°, 270°) as the gantry rotates. Accordingly, the housing may have four transparent portions or windows at four locations that correspond to the four circumferential locations. Similarly, an imaging system may be configured to acquire image data when the one or more sensors or cameras are located at two circumferential locations (e.g., 0°/360° and 180°), or at three circumferential locations (e.g., 0°/360°, 120°, and 240°) as the gantry rotates. Accordingly, the housing may have two or three transparent portions or windows, at two or three locations that correspond to the two or three circumferential locations, respectively. The transparent portion(s) or window(s) of the housing may be made of any transparent or translucent material, for example, acrylic. Some radiation therapy systems may comprise more than one optical patient-monitoring imaging system mounted on more than one rotatable gantry. For example, a first rotatable gantry for a CT system and a second rotatable gantry for a PET system, with a first imaging system mounted on the first rotatable gantry and a second imaging system mounted on the second rotatable gantry. The first and second rotatable gantries may each define rotational planes that may be coplanar or not coplanar (e.g., separated by a distance in the IEC-Y direction). The housing of a radiation therapy system having two rotatable optical imaging systems may comprise a first transparent portion corresponding to the movement trajectory of the first imaging system and a second transparent portion corresponding to the movement trajectory of the second imaging system, where the first and second transparent portions may be separated by a distance in the IEC-Y axis. For example, each transparent portion may comprise a clear window strip that allows optical imaging sensors of the first and second optical imaging systems to acquire optical data as the gantry rotates. Radiation therapy systems having patient-monitoring imaging systems comprising terahertz sensors may comprise a housing with one or more portions or windows made of a material that is transparent to the wavelength of the terahertz sensors. Examples of such terahertz-transparent materials may include silicon, and polymers such as polytetrafluoroethylene (PFTE, aka Teflon) and TPX (polymethylpentene film), polypropylene (PP), polyethylene (PE) and high density PE (HDPE).

Figure 6A:
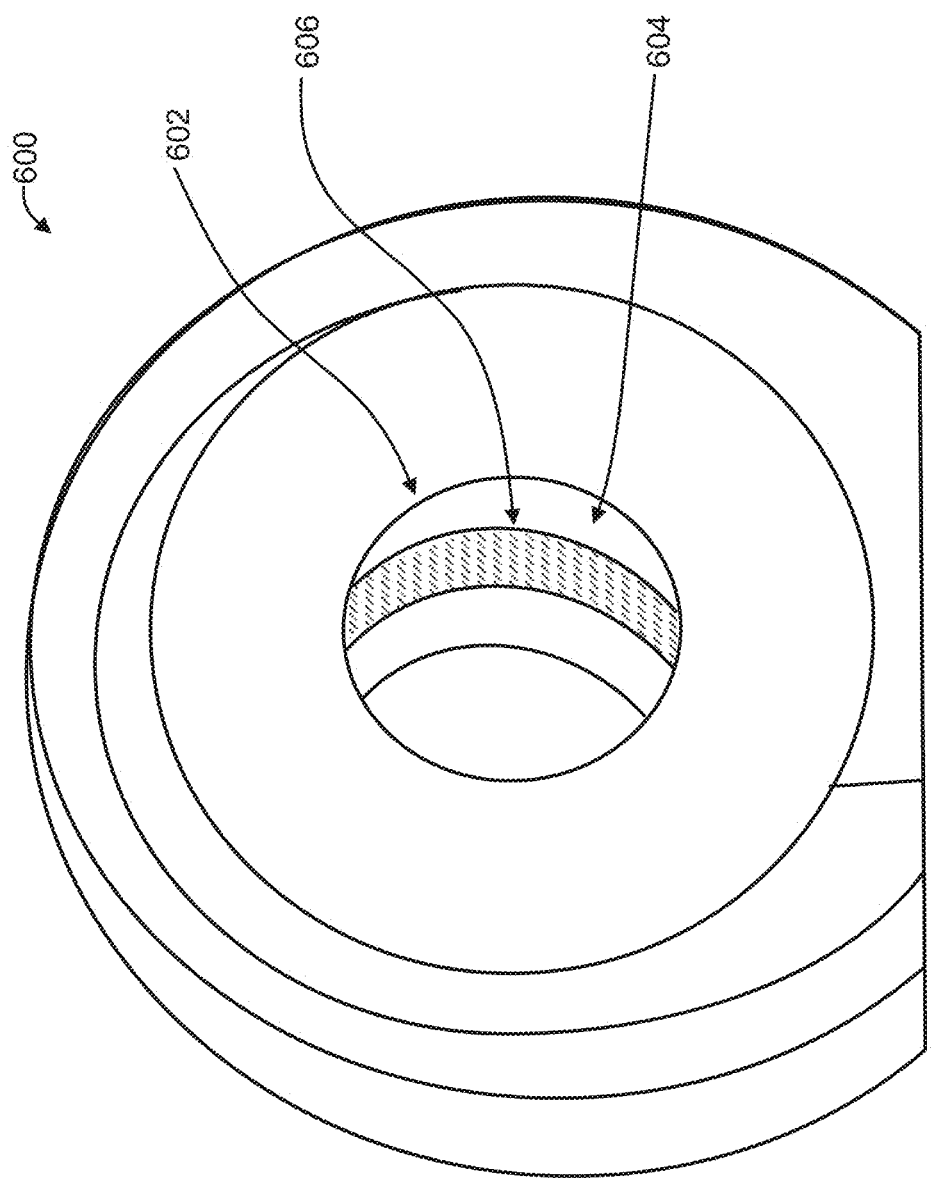
FIG. 6A provides a schematic perspective view of one variation of a radiation therapy system housing.
Figure 6E:
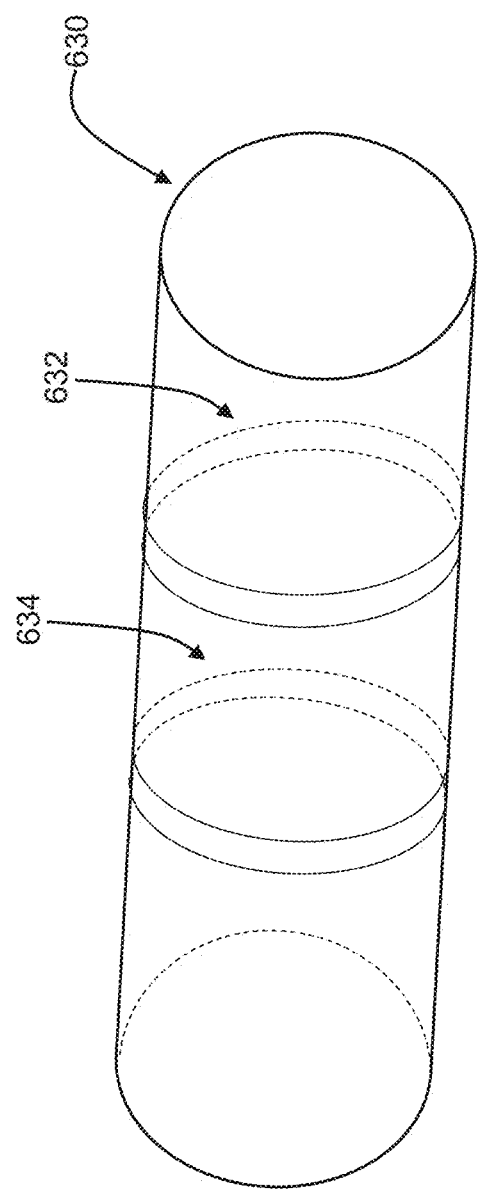
FIG. 6E provides a partial perspective view of one variation of a bore of a radiation therapy system housing.

One variation of a radiation system housing comprising a transparent or translucent region is depicted in FIGS. 6A-6B. The gantry housing (600) may comprise a longitudinal lumen (602) that corresponds with the patient treatment region or bore (604) and a light-transmitting window or region (606) along an inner surface of the housing. The light-transmitting region (606) may correspond to the FOV of the optical imaging system and/or movement trajectory of the one or more optical sensors or cameras. As depicted in FIGS. 6A and 6B, the light-transmitting region (606) may be located along the inner diameter of the longitudinal lumen (602). In this variation, the light-transmitting region (606) circumscribes the entire inner diameter of the lumen, but in other variations, the light-transmitting region may extend along a segment or arc of the inner diameter of the lumen, and not the entire circumference. The light-transmitting region may be one continuous or contiguous region or window, such as the strip depicted in FIGS. 6A and 6B, or may comprise a plurality of light-transmitting segments that extend along a sub-portion of the circumference, as is depicted in FIGS. 6C and 6D. The location of each of the light-transmitting segments or windows may correspond with each of the circumferential locations around the bore where the patient-monitoring imaging system is programmed to acquire images and/or which correspond to the locations of light emitters and/or detectors or sensors during image acquisition. For example, a housing lumen (610) may comprise two windows (612, 614) located at two circumferential locations (e.g., 0°/360° and 180°) as shown in FIG. 6C. Alternatively, a housing (620) may comprise four windows (622, 624, 626, 628) located at four circumferential locations (e.g., 0°/360°, 90°, 180°, 270°) as depicted in FIG. 6D. Each of the windows may span across an arc angle, where the angular spread of each window may correspond with the FOV of the image sensor(s) or detector(s), and may be, for example, from about 5° to about 85°, e.g., about 15°, about 30°, about 45°, about 60°, etc. A system comprising more than one patient-monitoring imaging system may include multiple light-transmitting regions along different planes or slices of the longitudinal lumen. FIG. 6E depicts one variation of a longitudinal lumen of a housing for a radiation therapy system having two rotatable optical imaging systems. The housing (630) may comprise a first transparent region or window (632) corresponding to the movement trajectory of the first imaging system and a second transparent region or window (634) corresponding to the movement trajectory of the second imaging system, where the first and second transparent portions may be separated by a distance in the IEC-Y axis. The first and second transparent regions (632, 634) may each comprise a single continuous or contiguous strip (as in FIG. 6B) or a plurality of windows (as in FIGS. 6C and 6D). As described above with regard to the position of the monitoring imaging system relative to the therapeutic radiation source, the light-transmitting or transparent regions may be coplanar with the therapeutic radiation source or may non-coplanar with the therapeutic radiation source.

Figure 2A:
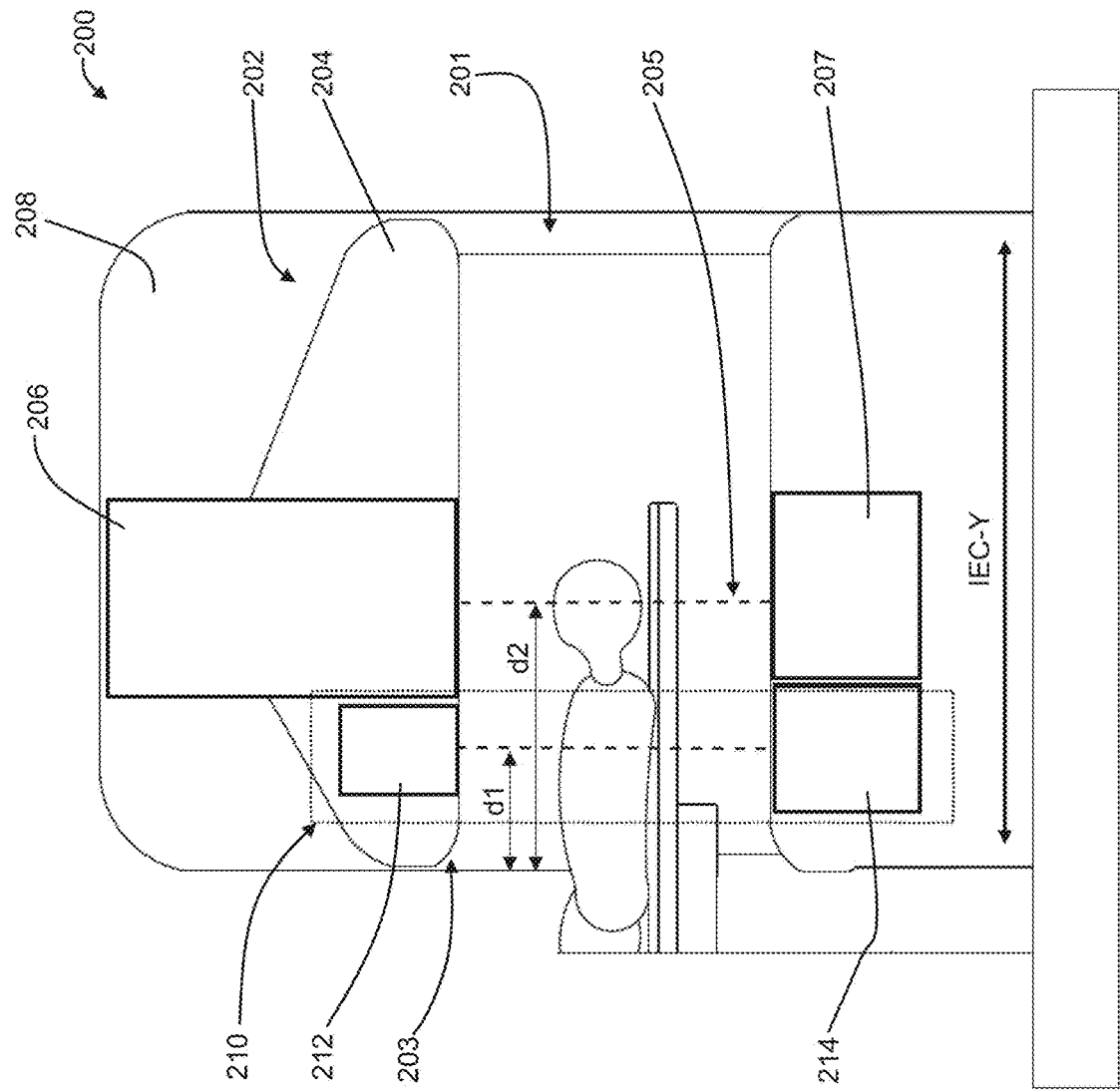
FIG. 2A is a schematic cross-sectional side view of one variation of a radiation therapy system having a patient-monitoring imaging system.

FIG. 2A is a schematic side cross-sectional view of one variation of a radiation therapy system comprising a patient-monitoring imaging system located on a rotatable ring of a circular gantry. The radiation therapy system (200) may comprise a circular gantry (202) having a rotatable ring (204) that is rotatable about a patient treatment region within a bore (201), a therapeutic radiation source (206) mounted on the rotatable ring (204), and an imaging system (210) mounted on the rotatable ring (204). The rotatable ring (204) of the circular gantry may be coupled to a stationary frame (not shown). The circular gantry (202) may be enclosed within a system housing (208). The surface of the housing may form the sidewalls of the bore. The patient-monitoring imaging system (210) may comprise an emitter (212) and a detector (214) that are mounted across from each other on the rotatable ring (204). The emitter (212) may be an X-ray source (e.g., backscatter X-ray emitter), a light source such as a LED (e.g., emitting light of any spectrum, including infrared light, visible light, UV light, etc.), as well as laser profiler emitters (with or without structured light), ultrasound emitters, terahertz wave emitters. The detector (214) may be an X-ray detector, an image sensor or detector (e.g., photon detector such as an optical detector having one or more CCD sensors and/or CMOS sensors), monoscopic or stereoscopic cameras, ultrasound detector, terahertz detector, and/or any range-measurement device. Alternatively, the patient-monitoring imaging system (210) may not have an emitter or illumination source, but may have a detector that comprises one or more image sensors that acquire image data using ambient light. In some variations, a light emitter or illumination source may be located around an optical assembly of the detector or light sensor. For example, an optical assembly may be disposed over the detector or light sensor, and the optical assembly may comprise a focusing lens that may be located over the detector and a light emitter having a circular shape that circumscribes (i.e., located around the perimeter of) the lens. This may help to provide additional illumination to the patient regions within the FOV of the imaging system detector. If a light emitter or illumination source is located around or adjacent to the detector, a light emitter located opposite the detector may be optional. The therapeutic radiation source (206) and the patient-monitoring imaging system (210) may located at different longitudinal locations along the IEC-Y axis (i.e., the therapeutic radiation source and the imaging system are not coplanar). For example, the patient-monitoring imaging system (210) may be located such that the center of the patient-monitoring imaging system is a first distance d1 from an opening (203) of the bore (e.g., bore entrance opening) while the therapeutic radiation source (206) may be located such that the center of the therapeutic radiation source is at a second distance d2 from the opening (203), where d2 is greater than d1 (for example, d1 may be about 60 cm and d2 may be about 110 cm). In this configuration, as the patient is advanced into the bore from the bore entrance opening (203), image data of a patient region may be acquired before that region crosses a treatment plane (205) of the therapeutic radiation source (which may or may not coincide with the center of the therapeutic radiation source).

Figure 2B:
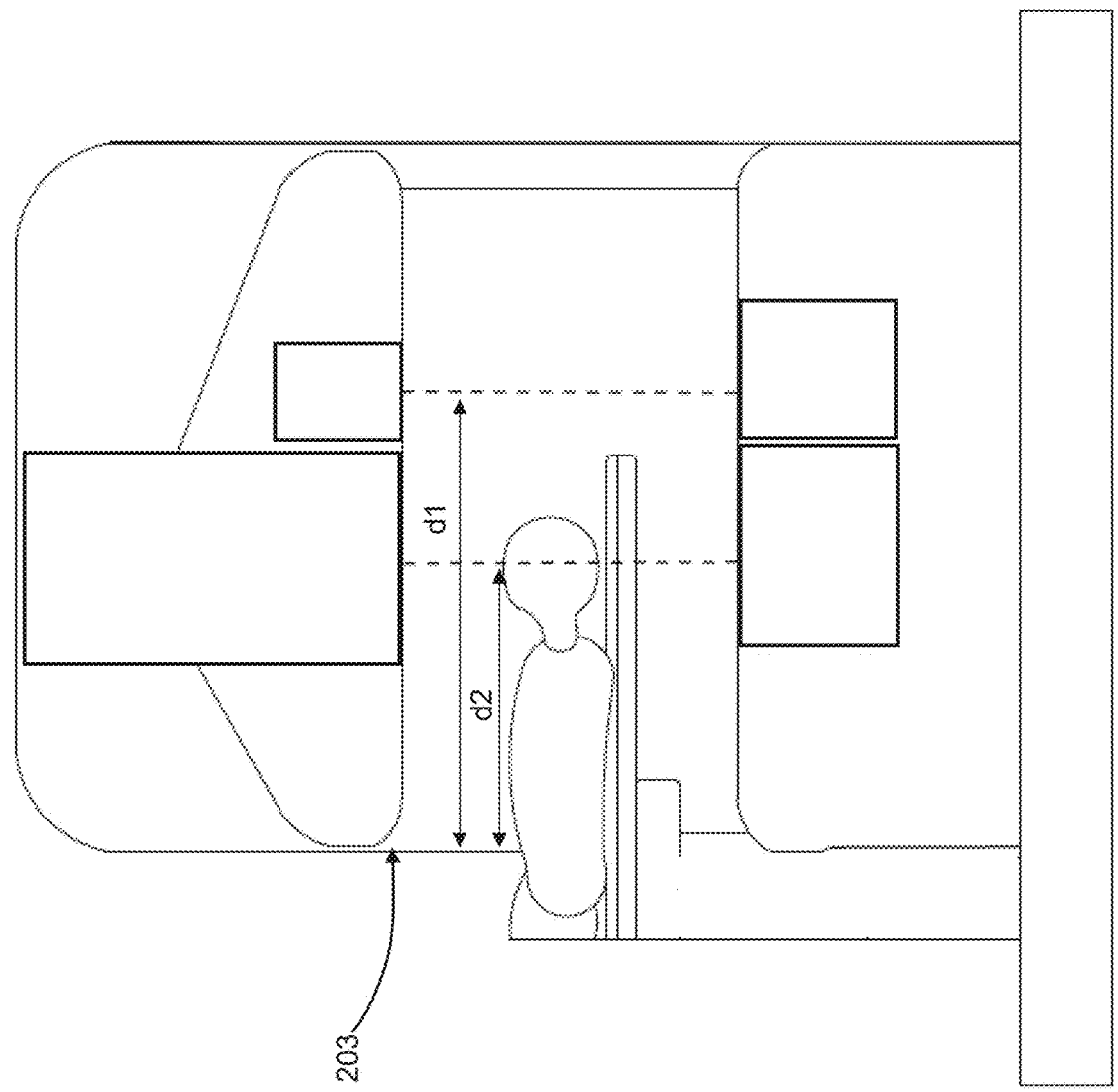
FIG. 2B is a schematic cross-sectional side view of one variation of a radiation therapy system having a patient-monitoring imaging system.

Alternatively, as depicted in FIG. 2B, distance d1 may be greater than d2. In this configuration, as the patient is advanced into the bore from the entrance opening (203), a patient region may cross the treatment plane before imaging data of that region is acquired. While FIGS. 2A and 2B depict radiation therapy systems comprising an imaging system that is at the same circumferential location as the therapeutic radiation source (which may help to reduce or limit radiation damage to the sensors of the imaging system), in other variations, the imaging system may be located at a different circumferential location as the therapeutic radiation source. In some variations, the patient-monitoring imaging system may be radially offset at an angle from the therapeutic radiation source and/or circumferentially offset by an arc length from the therapeutic radiation source. For example, the patient-monitoring imaging system may be radially offset by about 1°, about 3°, about 10°, about 15°, about 20°, about 30°, or about 45° from the therapeutic radiation source. The patient-monitoring imaging system may be circumferentially offset by an arc length that is from about 10% to about 50% of the circumference of the gantry. In some variations, the imaging system may be mounted at the same longitudinal location as the therapeutic radiation source (e.g., d1 is approximately the same as d2, the imaging system and the therapeutic radiation source are coplanar), however, may be located at a different circumferential location as the therapeutic radiation source.

Figure 2C:
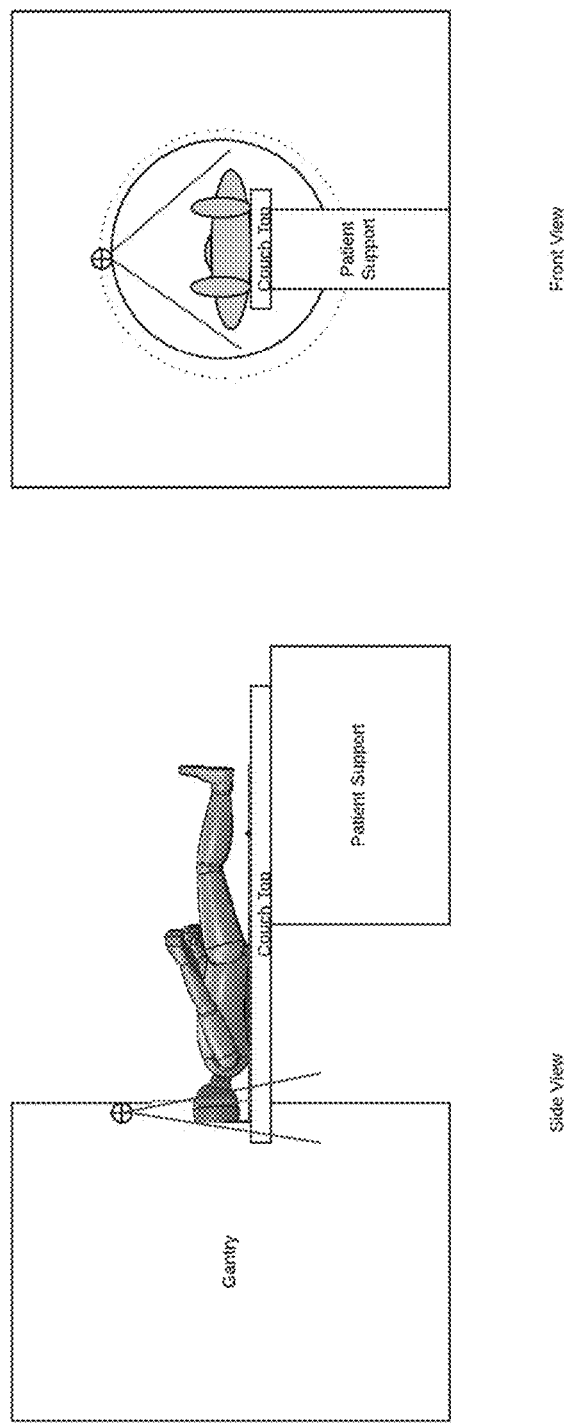
FIG. 2C provides schematic side and end views of one variation of a radiation therapy system having a patient-monitoring imaging system.
Figure 3A:
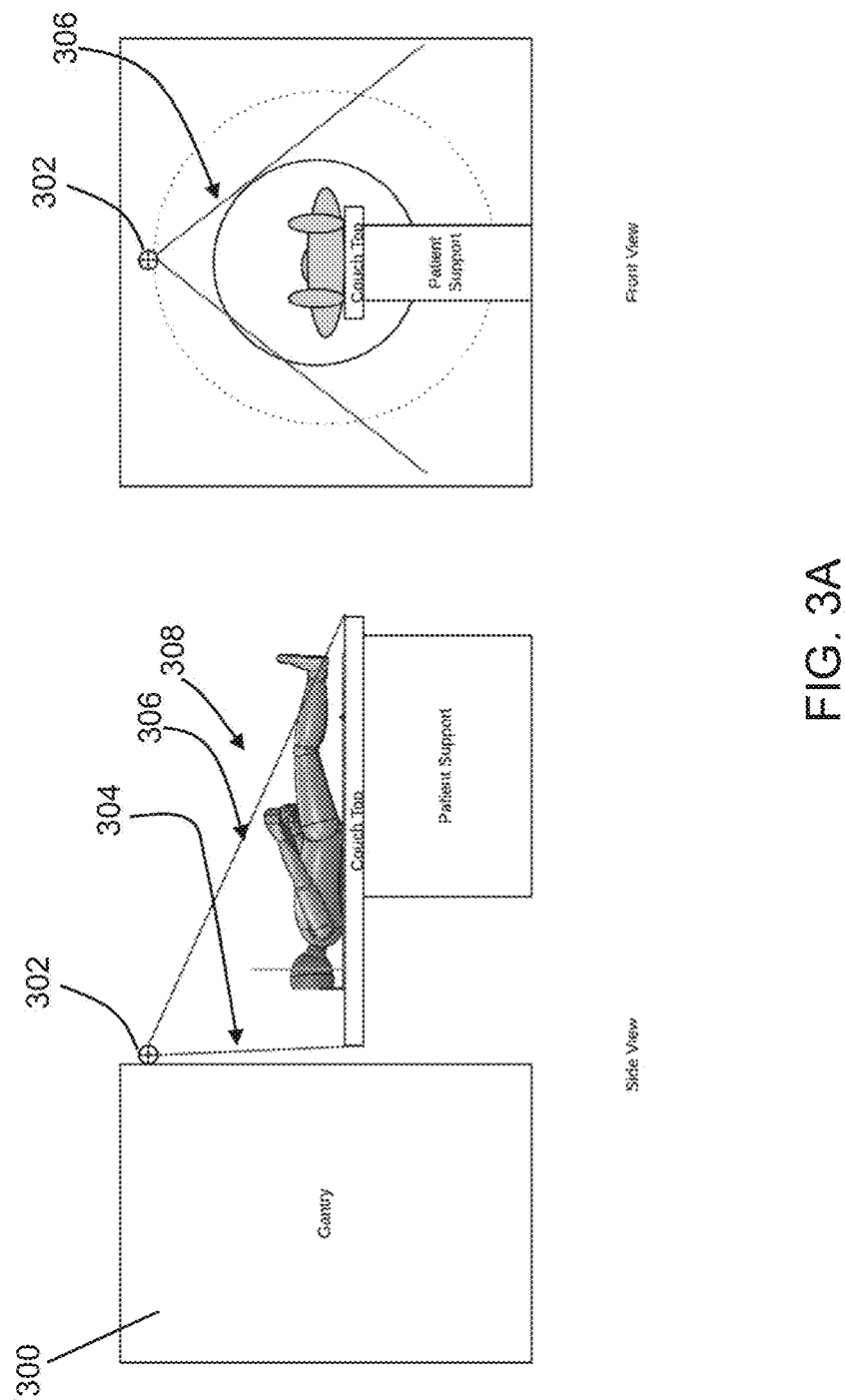
FIG. 3A provides schematic side and end views of one variation of a radiation therapy system having a patient-monitoring imaging system.
Figure 3B:
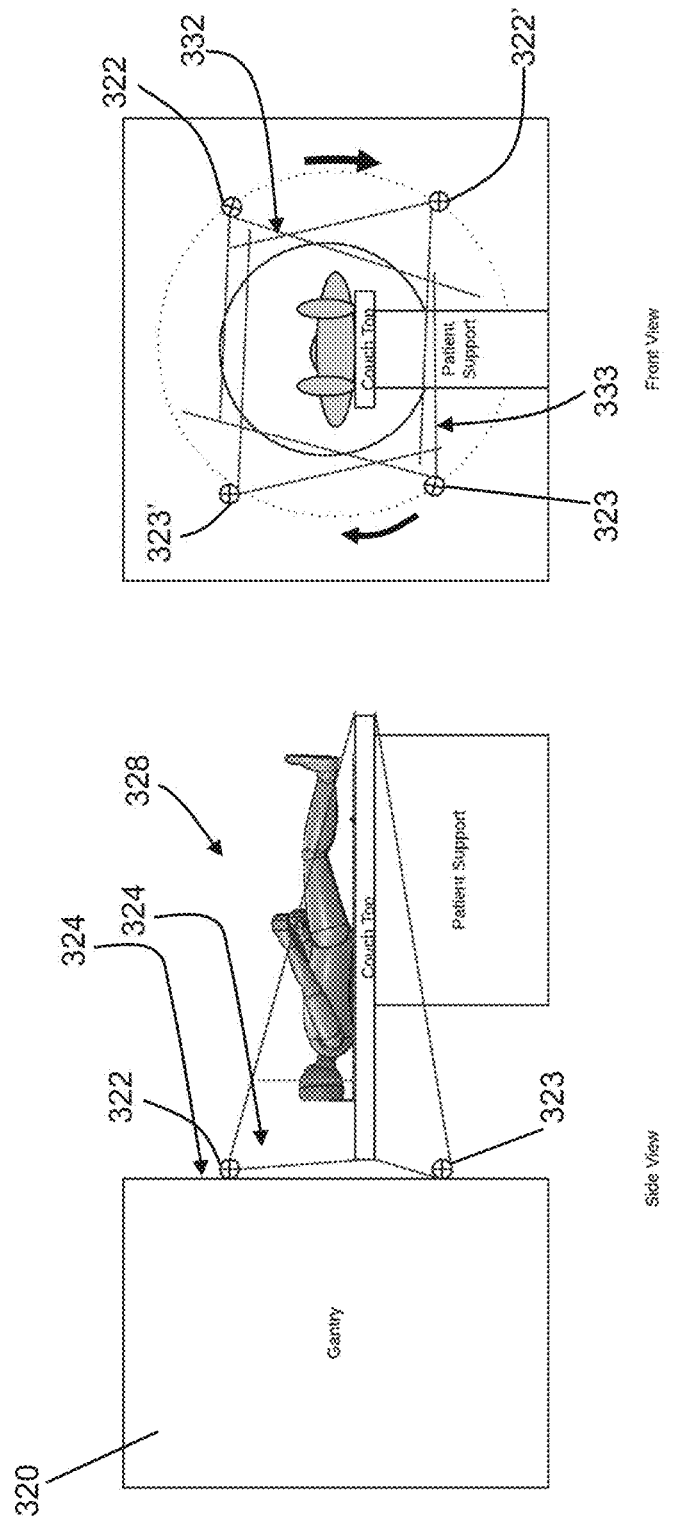
FIG. 3B provides schematic side and end views of one variation of a radiation therapy system having a patient-monitoring imaging system.

While the patient-monitoring imaging systems of the radiation therapy systems in FIGS. 2A and 2B are mounted on the rotatable circular gantry such that the imaging plane or FOV is substantially within a volume of the bore (e.g., the majority of the FOV is within the bore volume), in other variations, the patient-monitoring imaging system may be mounted toward the periphery of the bore such that the imaging plane or field-of-view include regions outside of the bore (e.g., patient setup region). FIG. 2C depicts one variation of a radiation therapy system comprising an imaging system mounted on a rotatable gantry near the entrance opening of the bore. The imaging system may be mounted within about 10 cm of the entrance opening of the bore. The FOV of the imaging system may include a boundary region between the internal and external volumes of the bore, which provides patient image data to the system controller as the patient is moved into the bore. Since this imaging system captures images of a patient region before it enters the bore, a model (e.g., a 3-D model and/or 2-D surface) may be generated for the patient region that is currently within the bore, as well as for the patient region that has not yet moved to the imaging plane. This may help to mitigate collision of patient region with the housing of the radiation therapy system (e.g., housing, and/or gantry and/or bore walls) even at the entrance to the bore. Alternatively, the majority of the FOV of the imaging system may include the patient setup region outside the bore, which may include the patient support system (e.g., the platform), the patient, and/or any patient positioning devices. FIG. 3A depicts one variation of a radiation therapy system comprising a rotatable circular gantry (300) and a patient-monitoring imaging system (e.g., an optical imaging system) comprising an image sensor (302) mounted on the rotatable ring of the gantry (300), at or near the edge of a bore (304) (e.g., at or near a bore entrance opening). The image sensor (302) may be an optical image sensor, such as any described above. In the example depicted in FIG. 3A, the image sensor (302) may have a FOV (306) that includes a patient treatment setup region (308). In some variations, the image sensor (302) may be mounted to the gantry via a pivot joint or ball bearing, allowing the FOV to be adjusted to cover various areas of the patient treatment region and/or setup region, as may be desirable. As the image sensor (302) rotates with the gantry (300), the FOV may sweep around the setup region, which may include the patient, the patient platform or couch, the patient platform support, and/or any patient positioning devices. FIG. 3B depicts another variation of a radiation therapy system comprising a rotatable circular gantry (320) and an imaging system (e.g., an optical imaging system) comprising a first image sensor (322) and a second image sensor (323) both mounted on a rotatable ring of the gantry (320), at or near the edge of a bore (324) (e.g., at or near a bore entrance opening). The first and second image sensors (322, 323) may be located across from each other (e.g., about 180° apart from each other) on the gantry. FIG. 3B depicts a front view of the radiation therapy system, where the FOV (332) of the first image sensor (322) and the FOV (333) of the second image sensor (323) capture opposite sides of the patient treatment setup region. The FOV of each of the image sensors may have an angular sweep of about 90° and together, may capture about 180° of the setup region. As the gantry (320) rotates such that the first and second image sensors move about the setup region (e.g., to locations 322' and 323' respectively, about 90° from their original locations), the FOV of the image sensors may capture another 180° of the setup region, complementary to the first set of image data. In some cases, a patient-monitoring imaging system with one sensor or camera may rotate faster to attain a similar image data acquisition rate as a patient-monitoring imaging system with more than one sensor or camera. For example, a single-camera monitoring system may need to rotate at 60 RPM for an image data acquisition rate similar to a two-camera monitoring system that rotates at 30 RPM. By rotating the gantry quickly (e.g., about 30 RPM or more, about 40 RPM or more, about 60 RPM or more, etc.), the patient-monitoring imaging system can acquire image data from multiple points-of-view at a rate that is faster than most patient movement, a patient's position and/or location and/or geometry may be determined in real-time.

Moreover, image data (which may be used for 2-D image reconstruction and/or 3-D patient modeling) acquired while rotating the imaging system of the patient setup region may help facilitate registration of the patient with the radiation therapy system coordinate system before a treatment session, and may form a baseline patient position and/or location with which images acquired during the treatment session may be compared. The patient may be monitored throughout the session to confirm that they have not substantially deviated from the initial set up configuration. If the patient-monitoring imaging system detects a substantial deviation from the initial set up configuration or position (e.g., movement beyond a pre-determined threshold), a notification or alert may be generated. In some variations, the notification may be transmitted visually (e.g., to a display, lighting, etc.) and/or audibly (e.g., one or more tones) to the system operator. The operator may then pause the session in order to assess the condition of the patient and the system, and determine whether to proceed with the session (e.g., imaging and/or treatment). For example, if the operator is able to identify and address any patient and/or system issues, the session may be continued. If the issue(s) cannot be resolved, the session may be terminated. The imaging data acquired during a session may be stored and/or transmitted to a treatment planning system, and can be used to determine whether a radiation therapy treatment plan should be updated or adjusted in order to accommodate changes in patient geometry (e.g., size and shape) and/or patient positioning accessories for future sessions. For example, a radiation therapy treatment plan may be adjusted to account for increases or decreases in patient size, and/or patient positioning accessories included during treatment setup but not anticipated during treatment planning, and/or patient breathing patterns.

In some variations, a radiation therapy system may comprise a patient-monitoring imaging system that is stationary, and does not rotate about the patient treatment region and/or bore. In some variations, a stationary patient-monitoring imaging system may comprise one or more non-rotating sensor(s) or camera(s) mounted on the housing of the radiation therapy system inside the bore. Imaging data acquired by an in-bore stationary patient-monitoring imaging system may be used to generate a 2D surface map of a patient within the bore. Alternatively or additionally, a stationary imaging system may comprise one or more non-rotating sensor(s) or camera(s) mounted on the system housing just outside of the bore, where the FOV includes the patient treatment setup region. In some variations, the entire FOV of a stationary patient-monitoring imaging system may is entirely external to the bore or at least more than about 50% of the FOV is external to the bore.

While radiation therapy systems described above and herein are depicted as having a single patient-monitoring imaging system, it should be understood that a radiation therapy system may have more than one patient-monitoring imaging system. For example, some variations may have a first patient-monitoring imaging system that acquires position and/or location data of a patient region before it crosses the treatment plane, and a second patient-monitoring imaging system that acquires position and/or location data of the patient region after it crosses the treatment plane. One or both of the first and second patient-monitoring imaging systems may be rotatable. In some variations, a first patient-monitoring imaging system may be mounted on the rotatable gantry while a second patient-monitoring imaging system is stationary. A first patient-monitoring imaging system may be mounted on the rotatable gantry and located within a bore region of the system such that FOV includes the bore volume and a second patient-monitoring imaging system may be mounted on the rotatable gantry and located outside the bore region of the system (e.g., at the bore entrance opening, just outside the bore entrance opening) such that the FOV includes the patient setup region. A radiation therapy system may have one or more of the patient-monitoring imaging systems described herein, in any combination as may be desirable.

Optionally, visual markers projected onto, or worn by, the patient may provide reference points for image processing and/or reconstruction (2-D and/or 3-D) methods. For example, one or more retroreflectors or optical fiducials attached to the patient. Optionally, a patient may wear fitted clothing during a treatment planning or diagnostic imaging session and wear the same fitted clothing during a treatment session to help promote a more uniform visual field (e.g., uniform texture, spatial frequency, colors, etc.) to facilitate image processing by the patient-monitoring imaging system. Alternatively or additionally, an imaging system may comprise one or more emitters that may project structured light patterns or striped light patterns onto the patient, where contours of the patient may be highlighted or accentuated by distortions in the light patterns.

Figure 4A:
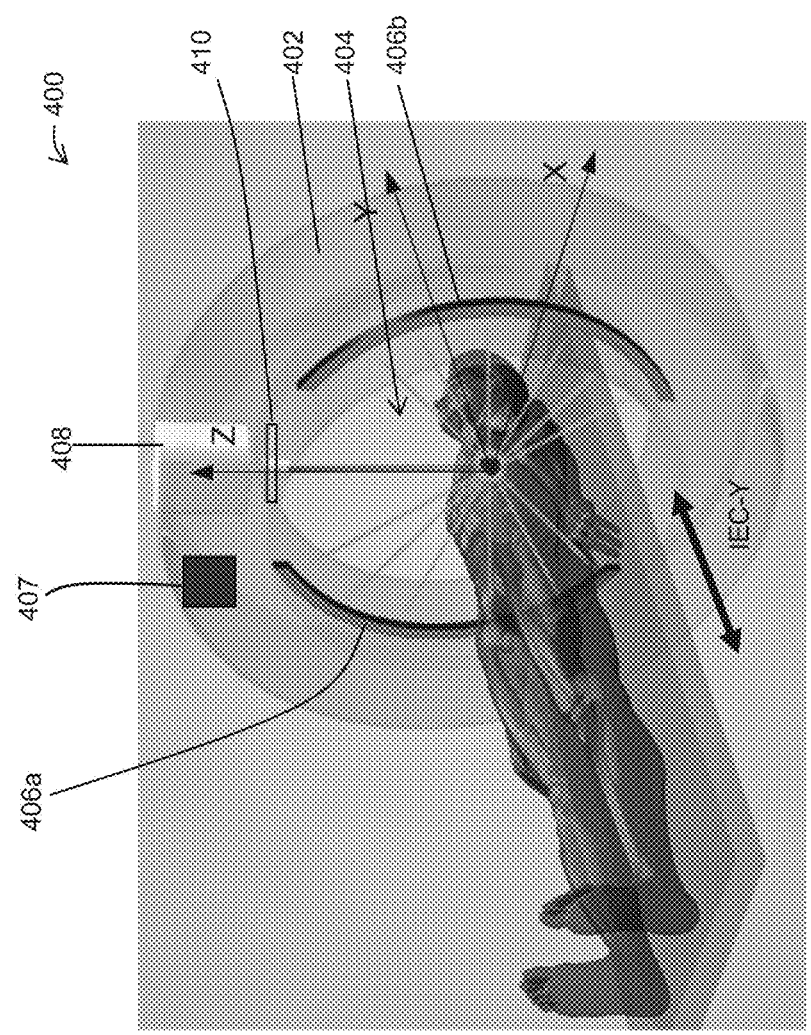
FIG. 4A is one variation of a radiation therapy system comprising a patient-monitoring imaging system.

One example of a radiation therapy system that may comprise any of the imaging systems described herein is depicted in FIG. 4A. The radiation therapy system (400) may comprise a gantry (402) rotatable about a patient area (404), one or more PET detectors (406) mounted on the gantry, a therapeutic radiation source (408) mounted on the gantry, and a dynamic multi-leaf collimator (410) disposed in the beam path of the therapeutic radiation source. The radiation therapy system (400) may also comprise a patient-monitoring imaging system (407) mounted on the rotatable gantry (402). The position of the imaging system (407) relative to the therapeutic radiation source (408) may be similar to any of those depicted in FIGS. 2A-2C and 3A-3B. In some variations, the radiation therapy system may comprise a first array of PET detectors (406a) and a second array of PET detectors (406b) disposed across from the first array, a linear accelerator (408) or linac, and a dynamic binary multi-leaf collimator (410). The system may further comprise a controller that is in communication with the gantry, PET detectors, linac, imaging system, and MLC, where the controller has one or more memories that may store treatment plans, radiation-firing matrices, fluence maps, system instructions/commands, patient image data, and a processor configured to execute the calculations and methods described herein. A patient disposed within the patient treatment region may have been injected with a PET tracer that emits positrons, and the PET tracer may accumulate at particular regions of the patient (e.g., irradiation-target regions such as tumor regions). The annihilation of a positron with a nearby electron may result in the emission of two photons traveling in opposite directions to define a line. The PET detectors may detect one or more positron annihilation emission paths (i.e., lines of response or LORs, emission paths). In some variations, the PET detectors may be time-of-flight PET detectors, which may help to identify the location of the positron annihilation event. A previously-calculated treatment plan P may be updated in accordance with the PET imaging data acquired by the PET detectors and/or image data acquired by the imaging system to update the fluence map such that the linac and MLC leaf configuration/beamlet selection account for tumor and/or patient movement. The fluence map may be updated using image data or LOR data as the patient is moved through the patient treatment region (e.g., stepped or otherwise moved through the gantry bore). Optionally, radiation therapy system (400) may comprise a CT system mounted on the same gantry as the therapeutic radiation source or mounted on a separate gantry. Additional details and examples of PET-based radiation therapy systems are described in U.S. patent application Ser. No. 15/814,222, filed Nov. 15, 2017 which is hereby incorporated by reference in its entirety.

Figure 4B:
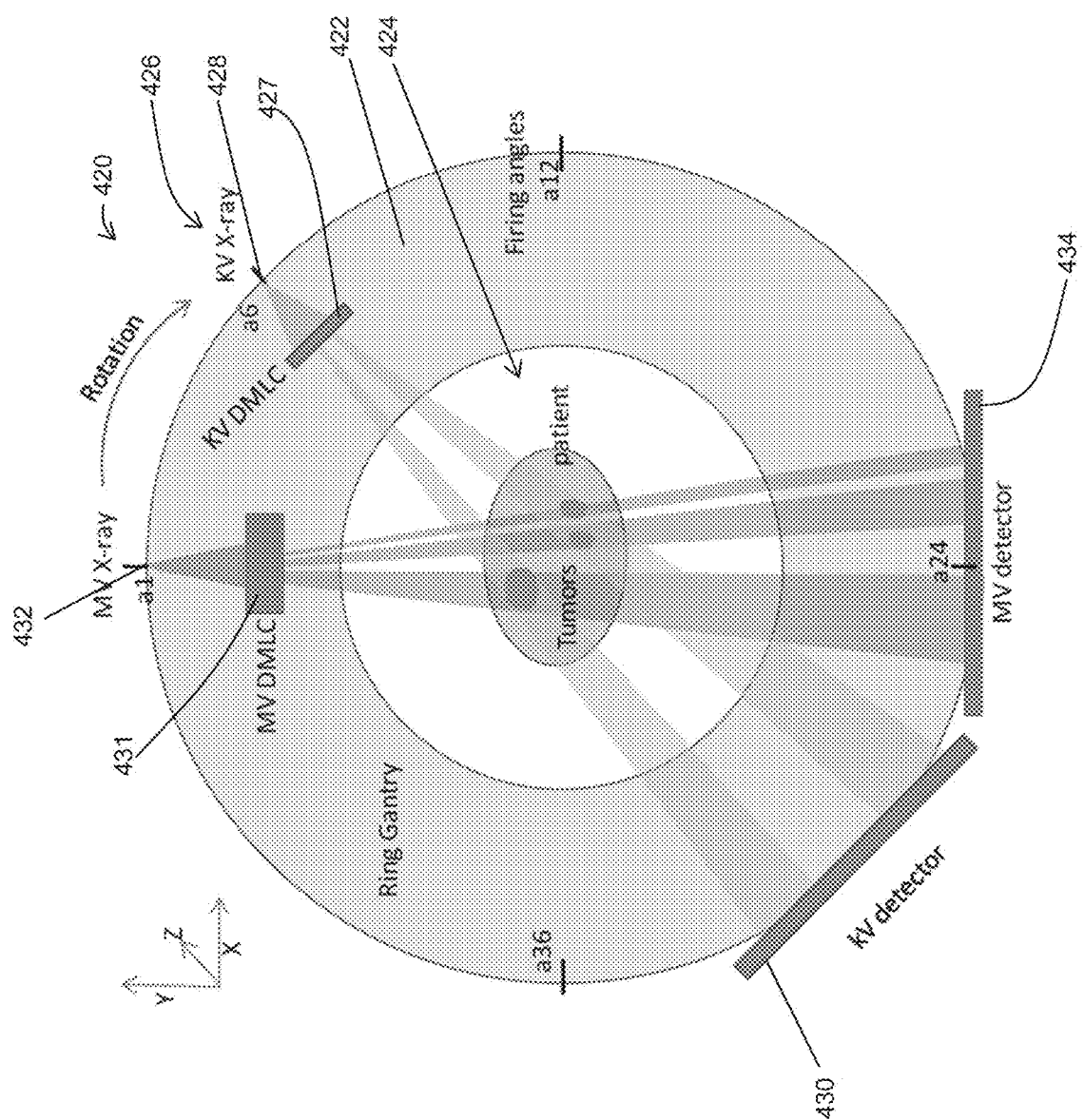
FIG. 4B depicts a cross-sectional view of another variation of a radiation therapy system comprising a patient-monitoring imaging system.

One example of a radiation therapy system that may comprise any of the imaging systems described herein is depicted in FIG. 4B. The radiation therapy system (420) may comprise a gantry (422) rotatable about a patient treatment region (424), an imaging system (426) having a kV X-ray source (428) and a kV detector (430) mounted on the gantry, and a therapeutic radiation source (432) (e.g., MV X-ray source) and a MV detector (434) mounted on the gantry (422). The kV detector (430) may be located across the kV X-ray source (428) and the MV detector (434) may be located across the MV X-ray source (432). Alternatively, the position of the imaging system (426) relative to the therapeutic radiation source (432) may be similar to any of those depicted in FIGS. 2A-2C and 3A-3B. Optionally, the kV imaging system may comprise a dynamic MLC (427) over the kV X-ray source (428). The system may comprise a dynamic MLC (431) disposed over the MV X-ray source (432). Imaging data may comprise image data acquired by the kV detector after each kV X-ray source pulse (e.g., X-ray projection image data, such as 2D projection data). A previously-calculated treatment plan P may be updated in accordance with the kV X-ray imaging data acquired by the kV detector to update the fluence map such that the linac and MLC leaf pattern/beamlet selection account for patient and/or tumor movement. The fluence map may be updated using imaging data as the patient is moved through the patient area (e.g., stepped or otherwise moved through the gantry bore). Alternatively or additionally, partial MV X-ray images or data acquired by the MV detector may be used to update the fluence map and/or treatment plan and/or delivery instructions. Additional details and examples of radiation therapy systems are described in PCT Appl. No. PCT/US2018/025252, filed Mar. 29, 2018, which is hereby incorporated by reference in its entirety.

The imaging systems disclosed herein may not be limited to monitoring patient position and/or location for radiation therapy. For example, the imaging systems described herein may be used to monitor patient position and/or location in CT, PET, and/or MRI scanning systems that do not have therapeutic radiation sources to monitor patient position and/or location across multiple scan sessions. For example, patient position and/or location data from a previous imaging session may be used to help setup and register the patient for a subsequent imaging session. This may facilitate consistent patient positioning for each of a plurality of imaging sessions, and may help the alignment, comparison, and/or stitching of images acquired during different scan sessions. Alternatively or additionally, the imaging systems disclosed herein may be included in imaging systems (e.g., CT, PET, and/or MRI scanning systems) that are used to acquire images for radiation therapy treatment planning. In one variation, a scan of the patient on a patient platform (optionally, with patient fixation devices that may be used during a treatment session) may be acquired at the time the treatment planning images are acquired. The image data acquired from the scan may be used to generate a patient plan profile (e.g., a 3-D model such as a surface profile), which may include the position, geometry (e.g., anatomical size and shape), and/or any patient motion during the acquisition of treatment planning images. After the treatment plan is developed and the patient is set up for the treatment session (and with any patient fixation devices that were used in treatment planning) in a system that has a therapeutic radiation source and any of the patient-monitoring imaging systems described herein, image data may be acquired and then processed to generate a patient treatment profile. The patient treatment profile may be compared with the patient plan profile to evaluate whether the differences are acceptable for proceeding with radiation delivery and/or whether radiation delivery needs to be modified to compensate for any differences. The range of acceptable positional and/or geometrical differences of the patient and/or patient platform (e.g., registration envelope tolerance) may be determined by a clinician and/or clinic, and may optionally depend on patient-specific parameters such as their disease-state, size, age, and the like. The differences between the patient treatment profile and the patient plan profile may represent baseline, acceptable differences and patient scans, 3-D models, and/or motions during the treatment session may be compared with the baseline level of differences to determine whether the patient continues to be in position (i.e., remains in their set-up or designated positions) for radiation delivery.

Optionally, any of the monitoring imaging systems described herein may comprise one or more calibration phantoms that may be used at system setup to confirm correct system installation, and/or may be used on a daily, weekly, monthly, and/or yearly basis to confirm that the imaging devices, sensors, detectors (e.g., optical imaging devices, detectors, and/or sensors) are performing within an acceptable tolerance. A calibration phantom may comprise surface contour indicia having 3-D geometric structures or calibration reference markings of varying (but known or predetermined) radii of curvature, widths, heights, and lengths, some of which may be in the range of the radii of curvature, widths, heights, and lengths of a patient's body. Some calibration phantoms may be sized and shaped to mimic the size and contours of an adult patient or a child patient, and/or a patient with male anatomical features or a patient with female anatomical features. The surface contours of a phantom may have patterns of curves or ridges with known spatial characteristics (e.g., length or width, radius of curvature, spacing or distances between raised or protruding features, etc.), and may comprise, for example, steps (e.g., a saw tooth pattern with different tooth angles, spacing between steps, etc.), concave portions, convex portions, and/or difference raised or recessed shapes (i.e., circular, cylindrical, rectangular, etc.). The calibration phantom may be built into the patient platform at a non-treatment region (e.g., at either end of the platform, and/or at an underside of the platform) and/or may be removable from the patient platform (i.e., may be temporarily affixed to the patient platform or simply placed along indicia or other markings on the platform). For example, an underside region of the patient platform (i.e., the surface of the platform that is opposite the patient-contacting surface) may comprise one or more surface contour indicia (e.g., calibration reference markings) with known geometric parameters so that for each revolution of the camera, the surface contour(s) derived from the acquired image data of the platform underside may be compared with the known surface contour(s) of the surface contour indicia. If the difference between the calculated surface contour(s) and the surface contour indicia exceeds a threshold, a notification may be generated indicating the imaging system may need to be re-calibrated, serviced, and/or the imaging system detector(s) need to be replaced. By incorporating the calibration phantom as a fixture on the underside of the patient platform, the calibration and/or registration of the imaging system may be monitored regularly throughout a treatment and/or imaging session (e.g., checking calibration/registration at a rate of once every revolution, once every 2 revolutions, once every 5 revolutions, once every 10 revolutions, once every second, once every 2 seconds, once every 5 seconds once every 10 seconds, once every 30 seconds, once every minute, once every 3 minutes, once every 5 minutes, once every 10 minutes, etc.), and if the imaging system is no longer calibrated or registered within the desired tolerance, the user may be notified.

The imaging system may rotate about a phantom while acquiring image data, and then generate a 3-D model using the acquired image data. The generated 3-D model may be compared with the known geometry and location of the phantom and any differences may be recorded. The system may then determine whether the differences are within the uncertainty limit and/or an acceptable error range. Depending on the nature of the differences, the imaging system may adjust calibration factors (e.g., gain and/or sensitivity of the detector(s), corrections or offsets for distance measurements, or alignment of the detector(s) with one or more light sources, etc.) to reduce those differences. Alternatively or additionally, the inner surface of the bore region of the system housing and/or the patient platform may comprise one or more of the surface contours described above that may be used to calibrate the imaging system. For example, the surface of the bore that is located within the FOV of the imaging system (e.g., along the inner circumference of the bore) and/or a non-treatment region of a patient platform may comprise raised or recessed regions with known spatial and geometric characteristics and/or other such surface landmarks or fiducials that may be distinguished or extracted by the monitoring imaging system. The spatial and geometric characteristics of these surface contours calculated based on the acquire image data may be compared against the known properties of these contours to identify any discrepancies. If the identified discrepancies exceed an error threshold, then a notification may be generated indicating that the imaging system (e.g., the detector(s) or camera(s)) may need to be serviced or replaced. Images of fiducials or landmarks along the inner surface of a gantry housing within the bore may be acquired continuously during a treatment or imaging as the detector rotates around the bore and when a discrepancy is identified, a notification may be generated.

Methods

Image data acquired by any of the imaging systems described herein may be used to generate 2-D and/or 3-D patient models. For example, imaging data acquired by a rotatable patient-monitoring imaging system comprising a rotatable sensor may be used to generate a 3-D model of the patient, patient platform or couch, and any positioning or immobilization devices. The generated 3-D model may be used to monitor patient movements, including respiratory motion, to help tailor the delivery of therapeutic radiation. For example, a 3-D model generated based on image data acquired by an imaging system with a FOV that includes internal bore volume (and/or comprises sensor(s) or camera (s) that are located in the bore of the system) may provide precise and accurate position data that may be used to adjusting the fluence and/or timing of radiation pulses (e.g., respiratory gating). Image data acquired by an in-bore imaging system, whether it be a stationary or a rotatable imaging system, may also help confirm that patient positioning devices or fixtures remain in their designated locations even after the patient has been advanced into the system bore. For example, 3-D models may be used to confirm that a patient has not changed their position, and/or location, and/or geometry in the course of the session, and/or generate motion allowance or envelopes or ranges for the movement of the patient platform. The methods described herein may be used to monitor patient position and/or radiation therapy system position(s) for helical radiation delivery and/or beam station delivery. Furthermore, patient scans or models of varying degrees of resolutions or quality may be calculated at various time points during a treatment session. For example, during beam-on, acquired image data may be used to monitor patient motion and/or incremental changes from a previously-generated 3-D model and during beam-off, acquired image data may be used to generate an updated 3-D model.

One method for generating 2-D and/or 3-D patient model may comprise rotating the imaging system about the patient treatment region and/or patient setup region at least once. As the imaging system rotates, it acquires images of the treatment region and/or setup region. Some methods may comprise continuous rotation and continuous image acquisition. Alternatively or additionally, some methods may comprise stepped rotation and image acquisition. For example, the imaging system may rotate to predetermined locations about the circumference of the gantry (e.g., at the 0°, 90°, 180°, and 360°/0° circumferential locations), stop at those locations, and acquire one or more images at that location before advancing to the next location. Alternatively, the gantry may continuously rotate without stopping at any predetermined locations, but the imaging system may be configured to acquire images when located at predetermined locations. As described previously, the housing of a radiation therapy system may comprise one or more transparent portions that correspond with the motion trajectory of the imaging system, and/or the pre-determined locations where imaging system sensors acquire patient images.

After acquiring 2-D image data, the method may comprise generating a 3-D model of the patient and any other items in the patient treatment region (and/or setup region) based on the 2-D image data. For example, a 3-D reconstruction method may comprise depth sensing algorithms, and may comprise methods for calculating depth information based on image information of a 2-D image. Methods may comprise stereovision, laser scanning or triangulation, time-of-flight, and projected light methods.

After a 3-D model of the patient treatment region and/or setup region is generated (which may include data pertaining to both the patient and the platform), the known 3-D machine model of the patient platform may be subtracted from the 3-D model of the treatment region and/or setup region to derive the 3-D patient model, which may include a 3-D model, position and/or location of a patient and any attached accessories attached to the patient or the patient platform. In some variations, if the FOV of the imaging system is relatively narrow (e.g., size of the FOV is less than about half a body length of a patient), a 3-D patient model may be generated based on a series of partial 3-D models acquired sequentially as the patient is advanced into the radiation therapy system and the gantry rotates about the patient. Multiple partial 3-D patient models may be added/ registered together to form a patient 3-D model that approximates the geometry, position and/or location of the patient.

Some methods may comprise calculating or updating the patient 3-D model throughout the session and comparing the patient model to the system/machine 3-D model. The system/machine 3-D model at a particular time point may be determined based on the initial 3-D model (which is known at the time of manufacture) and the cumulative movements of the various components (e.g., platform, rotatably gantry, etc.) during the session. Continuous updates and re-registration of the patient 3-D model may be especially useful when the patient is advanced deeper into the bore. For example, an emission guided radiation therapy treatment session may comprise acquiring an initial set of imaging data using a rotatable optical patient-monitoring imaging system, acquiring a kV CT image of a patient on the patient platform, moving the patient into the bore, acquiring a PET image of the patient, and applying therapeutic radiation to the patient as the patient is moved through the bore. As the patient moves through the radiation therapy system, a rotatable optical patient-monitoring imaging system may continuously acquire image data to generate and update patient 3-D models.

In some variations, an updated patient 3-D model may be used to confirm that the patient has not deviated from their position during setup. For example, a cross-section of the patient 3-D model may be calculated to map the location of the patient within the cross-section of the bore. For example, a cross-section of a patient 3-D model may be calculated based on images acquired of a patient wearing form-fitted clothing during the treatment planning scan, if required. In some variations, the clothing may be substantially transparent to terahertz or lower energy X-ray backscatter sensors. At a later imaging scan and/or treatment session, the patient may wear the same form-fitted clothing, if required, and an updated cross-section of the patient 3-D model may be calculated and compared to the previous cross-section. If the patient is in a similar position as they were during the planning scan, the scan and/or treatment session may proceed. In some variations, an optical imaging system (or any non-ionizing imaging system) may acquire data and a patient 3-D model may be generated before the patient is exposed to any ionizing radiation. For example, after a patient is set up on the platform, an optical imaging system may acquire data and generate the patient 3-D model before a patient CT image is acquired. If the patient 3-D model indicates that the patient position and/or location and/or geometry is similar to the patient position and/or location and/or geometry during treatment planning, then the radiation therapy system may then perform a CT scan and/or proceed with radiation delivery. Optionally, a 3-D model of the patient's face may be used for verifying their identity (using various facial recognition techniques) prior to scanning and/or treatment.

In some variations, an updated patient 3-D model may be used to monitor patient motion in the bore. A patient 3-D model generated based on image data acquired in real-time may be used to register the patient to a volume image such as a kV CT image and/or to detect patient motion that may trigger a pause in radiation delivery. Patient 3-D models generated using image data acquired during a treatment session may optionally be compared with patient 3-D models acquired during the acquisition of treatment planning images, and this comparison may be used to determine whether to adjust the treatment plan and/or radiation delivery to compensate for any changes in patient positioning and/or geometry. In some variations, certain changes in the patient 3-D model may merit adjustments to the radiation delivery. For example, preset thresholds may define when there is a substantial difference in the patient 3-D model compared to a reference model (such as a patient 3-D model generated at an earlier time point, and/or at the start of a treatment session), and the radiation therapy system may generate one or more notification indicating the nature of the patient change. For example, the radiation therapy system may generate a notification indicating that the patient has moved, and/or that the patient is in a particular phase of the breathing cycle (and optionally, whether the patient is in a breathing cycle phase suitable for radiation delivery), etc. If the patient position and/or location and/or any characteristics of the patient 3-D model has changed beyond the preset thresholds, the radiation therapy system may prompt the operator to pause radiation delivery or may optionally automatically pause radiation delivery.

In some variations, an updated patient 3-D model may be used for defining a patient platform or couch motion allowance or envelope for tumor position corrections. During a patient localization session just after the patient is set up on the platform in preparation for a treatment session, kV CT images may be acquired to identify any tumor position corrections needed prior to treatment and image data may be acquired and a patient 3-D model may be generated. The radiation therapy system can compensate for tumor position errors by moving (e.g., rolling, pivoting, shifting, tilting, etc.) the patient platform so that the tumor is in a desired location or orientation for radiation delivery. The patient 3-D model may be used to calculate the motion allowance of the patient platform that is available for making any tumor position corrections safely (e.g., without moving the platform into contact with the radiation therapy system). For example, the patient 3-D model may be compared with the machine 3-D model during the patient localization session, and a platform motion allowance may be calculated by identifying the bore space available for safe platform motion. This may allow the radiation therapy system to tailor platform motion allowances or motion ranges to a patient's size and geometry, which may allow for greater degrees of freedom and motion for tumor position correction. Optionally, patient motion allowances and/or motion envelopes that include an acceptable range of motion, may vary depending on whether the patient platform is moving and/or whether the therapeutic radiation source is emitting radiation. For example, the patient platform motion allowance and the patient motion allowance may be tighter during beam-on than during beam-off. In beam station delivery, the patient platform motion allowance and the patient motion allowance may be tighter when the patient platform is stopped at a beam station (i.e., in anticipation of radiation deliver) than when the patient platform is moving between beam stations. The differences between the motion allowances or ranges between beam-on and beam-off (and/or between when the platform is moving or stationary) may be determined or selected on a patient-specific basis by a clinician and/or a clinic.

Some optical imaging systems may comprise a controller that is configured to mitigate image distortions that may arise from rapid rotation of the optical detector. Image distortions may include, but are not limited to, image wobble (e.g., "jello effect"), skew, spatial aliasing (e.g., causing objects in the FOV to appear smeared), and/or temporal aliasing (e.g., strobe-like effects). The optical imaging system controller may be configured to employ one or more of various methods for rolling shutter rectification/correction and/or image stabilization, and/or may be configured to combine image data acquired over multiple revolutions to counteract or reduce the effect of these motion-related artifacts. Alternatively or additionally, some variations of radiation therapy system may comprise calibration reference markings and/or structures located on stationary components, such as the inner surface of the gantry housing in the bore region. Some variations may comprise calibration references markings and/structures located on the top side (i.e., patient side) of the patient platform. These and other calibration reference markings and/or structures (such as any reference markings on the underside of the patient platform) may be used alone or together to correct for image distortions. Optionally, a gyroscope (e.g., a MEM gyroscope) may be mounted near or adjacent to the imaging system detectors and the vibration data from the gyroscope may be used with a compensatory algorithm to correct for motion-related artifacts.

In some variations, the controller may optionally be configured to sort or bin image data based on the gantry angle from which the image data was acquired. For example, image data collected from gantry angles where the detector FOV includes the top portion of the patient platform (i.e., the patient side) may be binned and analyzed separately from image data collected from gantry angles where the detector FOV includes the bottom portion of the patient platform (i.e., the underside of the platform). Image data collected from the platform underside may not provide much, if any, information pertinent to patient positioning and motion, but may instead be used to measure platform sag (i.e., deflection of the patient platform due to the cantilever effect). Image data acquired from either side of the platform (i.e., on the right and left side of a patient) may optionally be used to measure platform sage. In variations where the patient platform underside has calibration or registration reference markings or contours, image data collected from the platform underside may be used to confirm that the imaging system is functioning within specified tolerances. Image data collected from the top (i.e., patient-side) of the platform may be used to monitor patient positioning and/or motion. During therapeutic radiation source beam-on, when patient position should remain as steady as possible (i.e., where the motion envelope relatively tight or small), close monitoring of the patient position may be prioritized over system calibration. For example, during beam-on, the imaging system may acquire image data from the top side of the platform and not the underside of the platform, which may increase the data acquisition and processing bandwidth allocated to calculating models and/or images that depict the position and/or motion of the patient. During beam-off, image data acquisition from the underside of the platform may resume in order to confirm system calibration and/or calculate platform sag/deflections.

The imaging system controller may also be configured to combine and/or stitch images of a patient and/or patient platform across multiple slices as the patient moves (e.g., continuously or in steps) along IEC-Y through the therapeutic radiation beam plane. In beam station delivery, each image slice may correspond to a particular beam station, and to generate a model of the patient along IEC-Y (i.e., along the length or height of the patient, to help generate a full-body or partial-body length model of the patient), the controller may acquire multiple image slices that are then stitched together. The width (i.e., thickness) of each slice may be a width (or other dimension) of the detector FOV. For example, the FOV for an optical detector may be from about 1 cm to about 20 cm or more, e.g., about 1 cm, about 2 cm, about 3 cm, about 5 cm, about 10 cm, or more, resulting in an image slice width having the same or similar dimensions. Some optical detectors may have a FOV of upwards of 20 cm, for example, from about 20 cm to about 100 cm, e.g., about 50 cm, about 60 cm, about 75 cm, about 80 cm, or more. In some variations, the FOV may be greater than the distance between individual beam stations so that the images may have some overlap (e.g., about 10% overlap, about 20% overlap, about 25% overlap, about 30% overlap, etc.), which may facilitate stitching multiple image slices together. In some variations, the patient may remain at a beam station for multiple revolutions of the imaging system, which may help provide a greater degree of patient position and motion detail. One variation of a method for stitching two (or more) images may comprise aligning the images such that they are on the same coordinate system, identifying one or more distinctive features that are common in both images and/or identify image pixels in the two images that correspond to each other, and adjusting position of the two images relative to each other such that the common or corresponding features in the two images are overlapping. In some variations, the imaging system controller may be configured to stitch or otherwise combine images acquired while the platform is moving, and may be configured to detect discontinuities between images (e.g., discontinuous regions for which image data was not acquired or the position change(s) of a common feature between two images is not captured) and to generate a notification to the user to re-scan the patient to bridge the discontinuities. For example, discontinuities may occur while scanning the chest/abdomen region, where breathing motions (e.g., respiratory cycle) may introduce image data variabilities that may require additional image data (e.g., additional scans of the same patient chest region). Such breathing artifacts may be at least partially mitigated by instructing the patient to perform a breath hold during image acquisition.

Imaging systems may have multiple scan modes, and optionally, the scan mode may be selected based on the radiation delivery mode. For example, an imaging system may have a first mode where image data is acquired only when the patient platform is stopped, and a second mode where image data is continuously required regardless of the patient platform motion. The first mode may be selected if image data of a single patient region is desired, and multiple images (e.g., axial images) may be acquired of the same patient region (e.g., across multiple revolutions of an optical detector around the patient while the platform is stationary). The first mode may also be selected for beam-station radiation delivery (e.g., step-and-shoot), where multiple images or image slices are acquired over multiple beam stations with some overlap (e.g., 25% overlap) between images. Image data may be acquired only when the platform is stopped at one of a series of beam stations, and the multiple image slices may be stitched together to build-up a patient and/or system model along IEC-Y. The second mode of image acquisition may be selected for helical radiation delivery where radiation is delivered while the patient platform is in motion (e.g., continuously in motion). In some variations, the second mode of image acquisition may be selected for beam-station delivery, where image data may be acquire both when the platform is stationary and when the platform is moving.

In some variations, an updated patient 3-D model may be used for generating collision notifications. The updated patient 3-D models may be continuously compared with the current system/machine 3-D model. Based upon this comparison, a notification may be generated indicating whether a collision between the patient, patient platform, positioning devices and the system housing (or any other components of the therapy system) is likely and optional instructions for avoiding such a collision. In some variations, collision checks may be performed with a pre-defined safety margin and if the patient 3-D model is located within the safety margin, then a collision notification or alert may be generated.

Figure 5A:
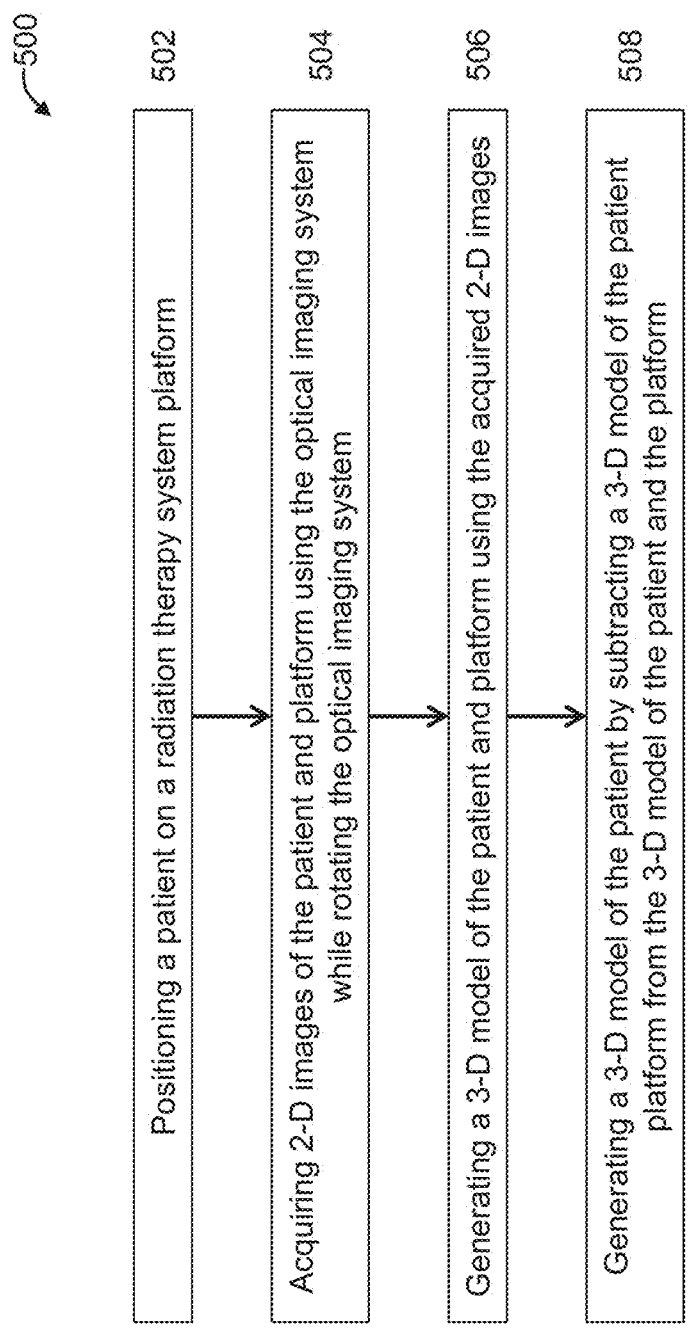
FIG. 5A depicts a flowchart representation of one variation of a method for generating a patient 3-D model.

FIG. 5A depicts a flow chart that represents one variation of a method for generating a patient 3-D model. Method (500) may comprise positioning (502) a patient on a radiation therapy platform, acquiring (504) 2-D optical images of the patient and platform while rotating the optical imaging system about the patient, generating (506) a 3-D model of the patient and platform using the acquired 2-D optical images, and generating (508) a 3-D model of the patient by subtracting a 3-D model of the patient platform from the 3-D model of the patient and the platform. The 2-D optical images of the patient and platform may also include any patient positioning devices, and the 3-D model of the patient and platform may also include the patient positioning devices. While the optical imaging system is rotating about the patient, the platform may be moving (e.g., along the IEC-Y axis) or may be stationary. The 3-D model of the patient platform may be generated based on CAD schematics of the structure of the platform and/or manufacturing log files, as well as any platform motion and may be stored in a memory of a system controller. As noted previously, the generation of a 3-D model may take place continuously during a treatment session or may take place at certain time points or system configuration changes during the treatment session. For example, in beam station delivery, a 3-D model may be generated using method (500) while the patient platform is moving between beam stations and the therapeutic radiation source is not emitting radiation. The generated 3-D model may be stored in a memory of the system controller. When the platform is stopped at a beam station and the therapeutic radiation source begins radiation delivery, the acquired image data may be used to calculate incremental deviations from the 3-D model generated while the platform was in motion. The acquired imaging data may optionally be used to calculate patient motion (e.g., rate at which a patient region or anatomical structure is moving) relative to the stored 3-D model.

Figure 5B:
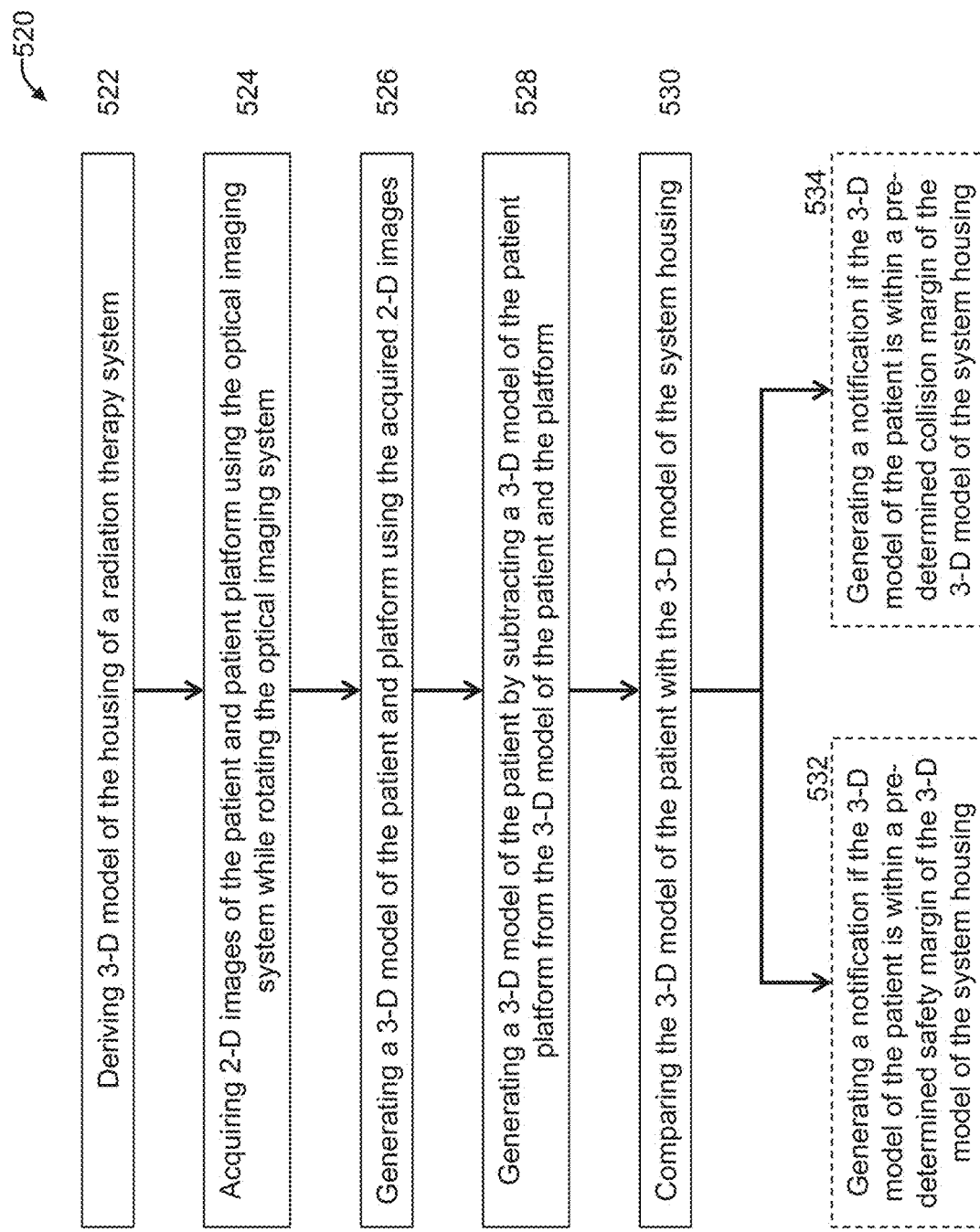
FIG. 5B depicts a flowchart representation of one variation of a method for generating a collision notification.

FIG. 5B depicts a flow chart that represents one variation of a method for generating a collision notification for a radiation therapy system. The radiation therapy system may comprise a rotatable gantry and a housing disposed over the rotatable gantry such that the volume of the bore is bounded by an exterior portion of the housing. Method (520) may comprise deriving (522) a 3-D model of the housing of the radiation therapy system. This may comprise generating the 3-D model based on CAD schematics of the structure of the housing and/or manufacturing log files, which may be stored in a memory of a system controller. Method (520) may further comprise acquiring (524) 2-D optical images of a patient and platform while rotating the optical patient-monitoring imaging system about the patient, generating (526) a 3-D model of the patient and platform using the acquired 2-D optical images, and generating (528) a 3-D model of the patient by subtracting a 3-D model of the patient platform from the 3-D model of the patient and the platform. The 2-D optical images of the patient and platform may also include any patient positioning devices, and the 3-D model of the patient and platform may also include the patient positioning devices. While the optical imaging system is rotating about the patient, the platform may be moving (e.g., along the IEC-Y axis) or may be stationary. Method (520) may further comprise comparing (530) the 3-D model of the patient with the 3-D model of the rotatable ring and generating (532) a notification if the 3-D model of the patient is located within pre-determined safety margin of the 3-D model of the system housing. Alternatively or additionally, the method (520) may comprise generating a notification if the 3-D model of the patient is located within pre-determined collision margin of the 3-D model of the system housing. The radiation therapy system may optionally automatically pause radiation delivery if any safety and/or collision notification is generated.

Calibration and Quality Assurance Methods

The system and patient monitoring imaging systems described herein may be calibrated at the time the systems are installed, and/or may be calibrated periodically according to a schedule or as desired (e.g., to troubleshoot any system errors or notifications that may have been generated during a treatment session). One variation of a calibration method may comprise moving a calibration phantom into the FOV of the monitoring imaging system, acquiring image data using the detectors and/or sensors and/or cameras of the monitoring imaging system, generating a model of the calibration phantom (e.g., a 3-D model, 2-D images, surface model, etc.), comparing the generated model of the calibration phantom with a reference model of the calibration phantom, and generating a notification (e.g., a visual or audio notification) that indicates whether the difference between the generated model and the reference model is within a registration envelope tolerance. Optionally, the method may comprise installing or placing the calibration phantom onto the platform (unless the phantom is built into the platform). Comparing the generated and reference models may comprise comparing their dimensions (e.g., length, width, height, depth, radius of curvature of each contour), relative position of different geometrical structures or landmarks along the surface, shapes and sizes of the geometrical structures or landmarks along the surface, and the like. The registration envelope tolerance may be determined by a clinician or may adhere to the standards of a clinic or hospital. If the difference between the generated model and the reference model is within the registration envelope tolerance, the system may generate a PASS notification. If the difference between the generated model and the reference model is outside of the registration envelope tolerance, the system may generate a FAIL or ERROR notification.

Since the monitoring imaging system is located in close proximity to a high-energy radiation source (i.e., the therapeutic radiation source), the sensitivity and/or precision of the detectors, as well as each of the sensor pixels of the detectors, may degrade over time. Daily, and/or weekly, and/or monthly quality assurance and/or calibration checks may provide information to a clinician and/or system administrator as to whether the detectors or sensors need to be replaced. Such checks may identify and/or count and/or locate sensor pixels on a detector that are faulty (e.g., elevated noise levels, non-responsive, drifting gain levels, intensity variations, etc.), and when the controller is analyzing the acquired image data, the data output from faulty pixels may be discarded or replaced with nearby pixel data outputs (e.g., by interpolation). In some variations, the output signals of each sensor pixel may be compared with expected output signals of that sensor pixel, and if the difference exceeds a pixel error threshold, that sensor pixel may be tagged as faulty. Similarly, noise levels (e.g., signal-to-noise ratio or SNR) may be calculated for each sensor pixel and if the noise levels exceed a maximum acceptable pixel noise level, that sensor pixel may be tagged as faulty.

One variation of a method for a quality assurance check of an imaging system that has at least one detector having one or more sensor pixels may comprise calibrating the gain and/or offset of the detector with nothing located in the patient treatment region (or FOV of the detector), acquiring N sets of image data using the detector as it rotates about the patient treatment region, and for each sensor pixel, calculating a difference from nearest neighbors (NND) and a standard deviation (STD) over the N sets of recorded image data. The method may comprise comparing each sensor pixel's calculated NND and/or STD values with a threshold NND and/or STD value. The threshold NND and/or STD values may be determined based upon the amount of variance that a clinician and/or technician deems acceptable, and/or may be derived by averaging all of the NND values (or STD values) over all of the sensor pixels in the detector. If the calculated NND and/or STD values of a sensor pixel exceeds the threshold NND and/or STD values, that sensor pixel may be marked or tagged as a faulty sensor pixel. Optionally, the quality assurance or calibration method may comprise checking whether the sensor pixels adjacent or near the faulty sensor pixels are also tagged as faulty, and if not, the output signal of the faulty sensor pixel may be substituted with a signal derived by interpolating the output signals of the nearby non-faulty sensor pixels. However, if the sensor pixels surrounding an identified faulty pixels have also been tagged as faulty and interpolation is intractable, then the method may comprise generating a notification such as an "ERROR (cannot interpolate)" signal, which may be a graphical element output to a display and/or an audio alert. The method may also comprise counting and storing a cumulative number of faulty sensor pixels in a detector, and if that number exceeds a predetermined limit, then the method may comprise generating a notification such as an "ERROR (number of faulty pixels exceeds limit)" signal, which may be a graphical element output to a display and/or an audio alert. In some variations, any error signal may indicate that the imaging system detector needs to be replaced while in other variations, only certain errors signals may require that the detector is replaced. For example, if the notification indicates that the number of faulty pixels has exceeded the limit, then the clinician and/or technician may be instructed to replace the detector. However, if the notification indicates that a faulty sensor pixel may not be interpolated, but the number of faulty pixels has not exceeded the limit (and the number of faulty sensor pixels that cannot be interpolated has not exceeded a predetermined limit), a clinician and/or technician may decide to proceed to test whether the image data is sufficient for calculating a 3-D model and/or for monitoring patient and/or platform motion. For example, the method may comprise moving a calibration phantom into the FOV of the monitoring imaging system, for example, by installing or placing the calibration phantom onto the platform, and acquiring image data using the detectors and/or sensors and/or cameras of the monitoring imaging system. The 3-D model of the surface contours and/or geometry of the phantom may be calculated based on the acquired image data and compared to a reference 3-D model of the phantom, and if the difference is within an error tolerance, the method may comprise generating a notification that the imaging system has a PASS status. If the difference is outside of the error tolerance, the method may comprise generating a notification that the imaging system has a FAIL status.

The calibration methods described herein may be performed daily, weekly, monthly, and/or yearly according to a schedule, and/or whenever the clinician wishes to troubleshoot or test the imaging system (e.g., in response to one or more error notifications). In variations where the radiation therapy system patient platform comprises one or more calibration reference indicia, these calibration methods may be performed as often as every single revolution, if desired. As described above, in some variations, the controller may be configured to monitor the calibration frequently (e.g., once every revolution, once every 2 revolutions, once every 5 revolutions, once every 10 revolutions, once every second, once every 2 seconds, once every 5 seconds once every 10 seconds, once every 30 seconds, once every minute, once every 3 minutes, once every 5 minutes, once every 10 minutes, etc.) during therapeutic radiation source beam-off, and may be configured to stop monitoring the calibration during beam-on.

An imaging system may be configured to calculate the rate at which the imaging system detector(s) are degrading in order to provide an estimate of when the detector(s) may need to be replaced or serviced. Detector degradation may be represented by drifts or shifts in detector sensor pixel gain and/or offset, and optionally, the noise levels of the gain and/or offset. For example, increased or widened noise levels or uncertainties may indicate that the imaging system detector is less reliable, and when detector sensor pixel gain and/or offset values have deviates past an acceptable (predetermined) threshold or limit, notifications or warnings may be generated to advise servicing or replacement. For example, there may be various levels of thresholds or limits for sensor pixel gain, offset, and/or noise values, and as the detector degrades, notifications indicating increasing levels of urgency and/or indicating increasing levels of degradation severity may be generated (e.g., detector is showing moderate levels of quality degradation to increased levels of quality degradation to severe levels of quality degradation to unacceptable levels of degradation, etc.). When a sensor pixel is entirely unresponsive to a light input, the system may generate a FAIL notification and may optionally lock operation of the imaging system and/or radiotherapy system until the detector is replaced or serviced/re-calibrated. In some variations, the imaging system controller may be configured to calculate the degradation rate of detector sensor pixels using calibration data acquired over time (e.g., a specified interval of time) where the pixel calibration may be represented by a gain and offset. The controller may be configured to calculate changes in sensor pixel noise over one or more sensor pixels of a detector and to monitor the rate of noise increase over increments of time. The controller may be configured to output an estimated length of time remaining until the detector is recommended for servicing and replacing by calculating the rate of a degradation factor (e.g., gain drift, offset drift, noise level increase, uncertainty increase) and extrapolating the time it would take for the value/level of that degradation factor to reach a threshold level indicating that such detector quality degradation is unacceptable and needs to be serviced or replaced. For example, the controller may be configured to calculate the rate at which the noise level of a detector (e.g., one or more of the sensor pixels on the detector) increase, and extrapolating or otherwise predicting or estimating the time it would take for the noise level to reach a maximum threshold level. The estimated remaining length of time for the detector before it exceeds the noise threshold and/or "expiration date" may be output to a system display for viewing by the clinician or user. Alternatively or additionally, a controller may calculate a pixel degradation rate based on a regression model and applying the regression model to the acquired image data. While some methods may comprise estimating the remaining life time until detector replacement or servicing based on sensor pixel noise levels (e.g., signal-to-noise ratio or SNR), some methods comprise estimating the remaining life time by measuring the differences between the expected sensor pixel output and the actual sensor pixel output when scanning a calibration phantom. For example, calculating the differences in the actual output signal of each sensor pixel and its respective expected output signal may comprise calculating the difference between intensity values of the output signal and intensity values of the respective expected output signal, and the pixel degradation rate is calculated or regression model based on changes in the calculated intensity differences over the specified interval of time. Alternatively or additionally, the imaging system may comprise one or more radiation measurement devices (i.e., dosimeters and the like) and may provide a recommendation to service or replace the imaging system detectors once a threshold level of radiation has been emitted by the therapeutic radiation source. Notifications of detector degradation and/or recommendations for servicing and/or replacing components (e.g., detector(s)) of the imaging system may comprise audio alerts and/or graphical notifications output to the system display.

Figure 7A:
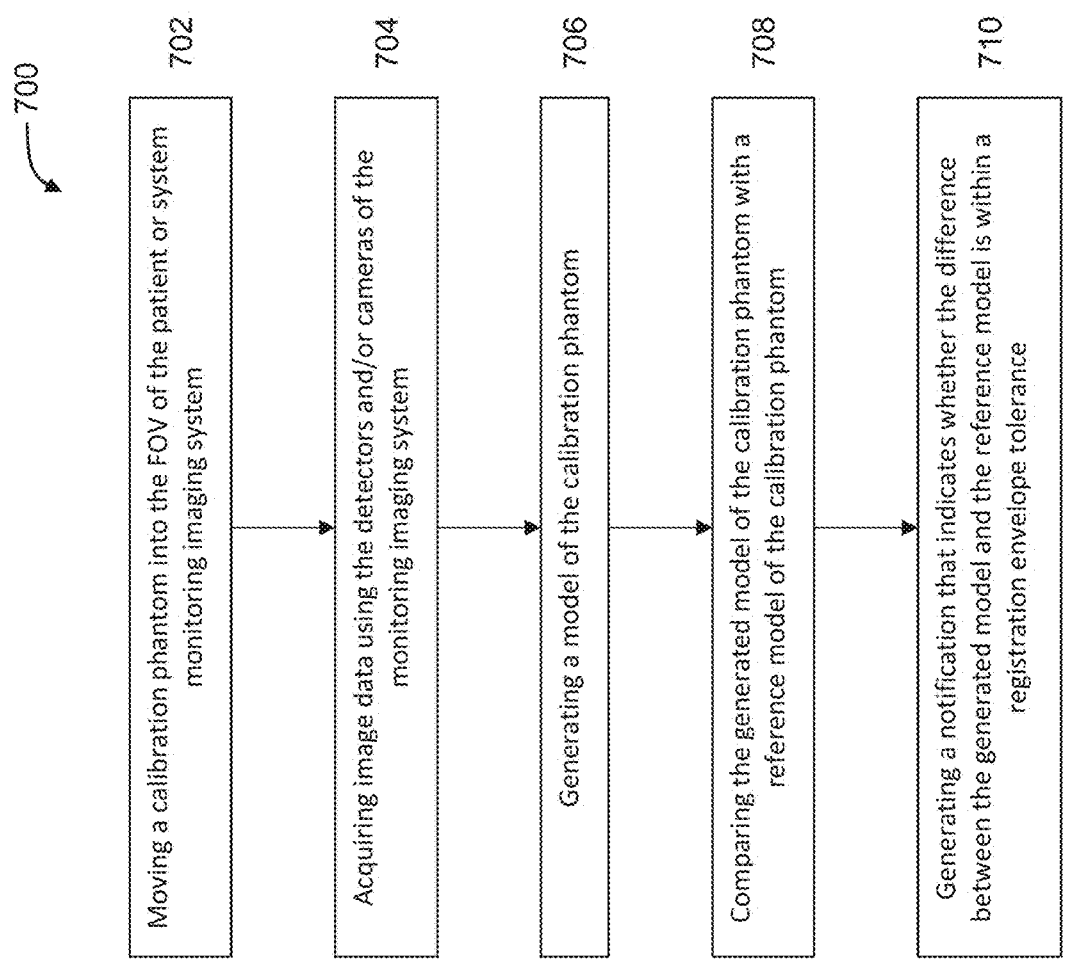
FIG. 7A depicts a flowchart representation of one variation of a method for calibrating a system or patient monitoring imaging system.

FIG. 7A depicts a flowchart representation of one variation of a calibration or quality assurance check that may be performed on, for example, a daily basis. The calibration method (700) may comprise moving (702) a calibration phantom into the FOV of the monitoring imaging system, acquiring (704) image data using the detectors and/or sensors and/or cameras of the monitoring imaging system, generating (706) a model of the calibration phantom (e.g., a 3-D model, 2-D images, surface model, etc.), comparing (708) the generated model of the calibration phantom with a reference model of the calibration phantom, and generating (710) a notification (e.g., a visual or audio notification) that indicates whether the difference between the generated model and the reference model is within a registration envelope tolerance. Optionally, the method may comprise installing or placing the calibration phantom onto the platform (unless the phantom is built into the platform). Comparing the generated and reference models may comprise comparing their dimensions (e.g., length, width, height, depth, radius of curvature of each contour), relative position of different geometrical structures or landmarks along the surface, shapes and sizes of the geometrical structures or landmarks along the surface, and the like. The registration envelope tolerance may be determined by a clinician or may adhere to the standards of a clinic or hospital. If the difference between the generated model and the reference model is within the registration envelope tolerance, the system may generate a PASS notification. If the difference between the generated model and the reference model is outside of the registration envelope tolerance, the system may generate a FAIL or ERROR notification. In some variations, an imaging system that has failed calibration may be serviced or replaced. For example, the detector(s) and/or camera(s) of the imaging system may be replaced.

Figure 7B:
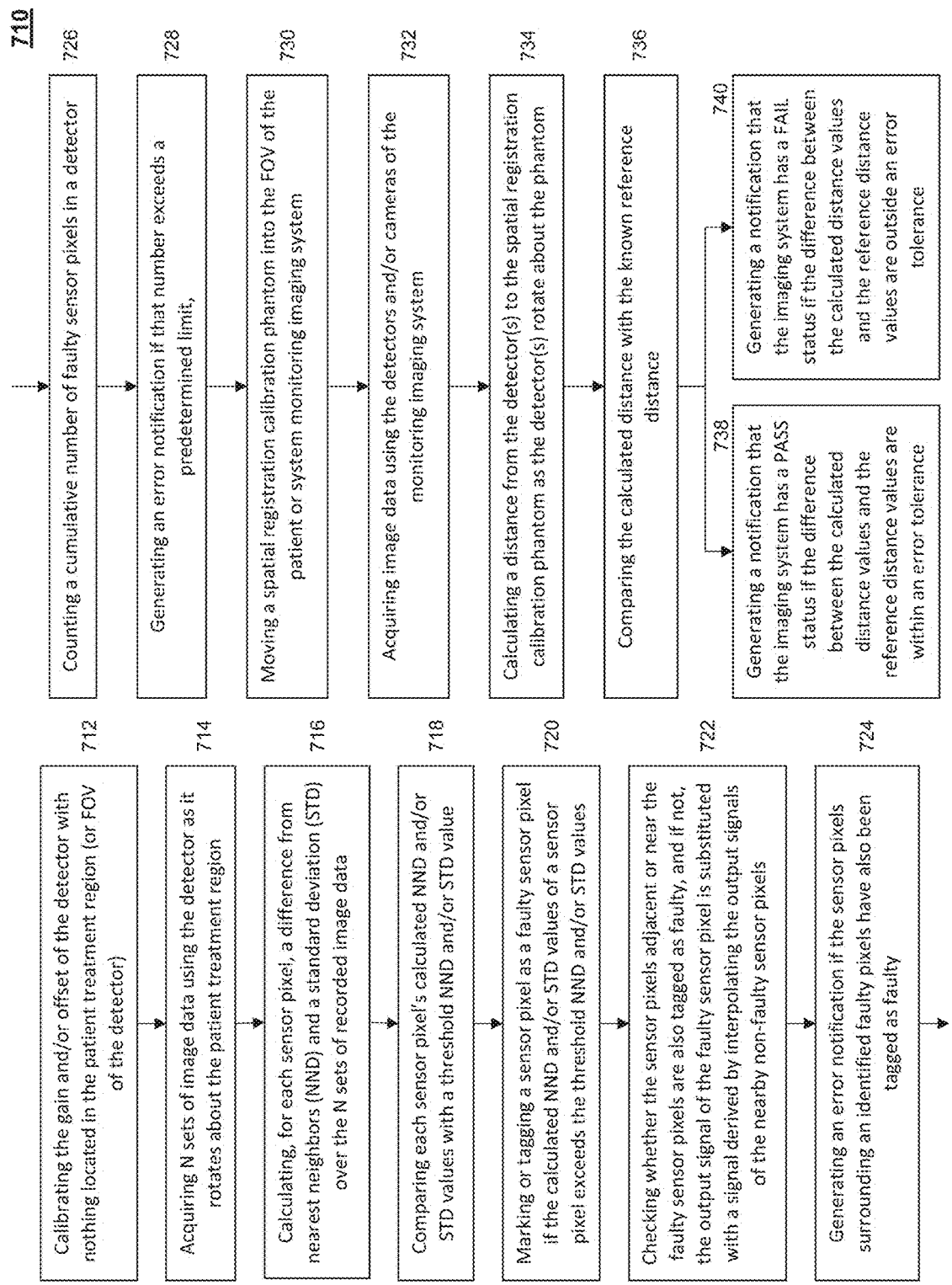
FIG. 7B depicts a flowchart representation of one variation of a method for calibrating a system or patient monitoring imaging system.

FIG. 7B depicts a flowchart representation of one variation of a method for a quality assurance check of patient and/or system monitoring imaging system. The imaging system may comprise at least one detector having one or more sensor pixels (e.g., a sensor pixel array). The method (710) may comprise calibrating (712) the gain and/or offset of the detector with nothing located in the patient treatment region (or FOV of the detector), acquiring (714) N sets of image data using the detector as it rotates about the patient treatment region, and for each sensor pixel, calculating (716) a difference from nearest neighbors (NND) and a standard deviation (STD) over the N sets of recorded image data. The method (710) may comprise comparing (718) each sensor pixel's calculated NND and/or STD values with a threshold NND and/or STD value. The threshold NND and/or STD values may be determined based upon the amount of variance that a clinician and/or technician deems acceptable, and/or may be derived by averaging all of the NND values (or STD values) over all of the sensor pixels in the detector. If the calculated NND and/or STD values of a sensor pixel exceeds the threshold NND and/or STD values, the method (710) may comprise marking or tagging (720) that sensor pixel as a faulty sensor pixel. Optionally, the quality assurance or calibration method may comprise checking (722) whether the sensor pixels adjacent or near the faulty sensor pixels are also tagged as faulty, and if not, the output signal of the faulty sensor pixel may be substituted with a signal derived by interpolating the output signals of the nearby non-faulty sensor pixels. However, if the sensor pixels surrounding an identified faulty pixels have also been tagged as faulty and interpolation is intractable, then the method may comprise generating (724) a notification such as an "ERROR (cannot interpolate)" signal, which may be a graphical element output to a display and/or an audio alert. The method may also comprise counting (726) and storing a cumulative number of faulty sensor pixels in a detector, and if that number exceeds a predetermined limit, then the method may comprise generating (728) a notification such as an "ERROR (number of faulty pixels exceeds limit)" signal, which may be a graphical element output to a display and/or an audio alert. Optionally, the method (710) may comprise moving (730) a spatial registration calibration phantom into the FOV of the monitoring imaging system, for example, by installing or placing the spatial registration calibration phantom onto the platform, and acquiring (732) image data using the detectors and/or sensors and/or cameras of the monitoring imaging system. A spatial registration calibration phantom may have a greater length along the IEC-Y axis and/or greater variability in surface contours than a daily QA phantom. This may help to confirm the accuracy of imaging along the IEC-Y axis and/or patient platform positioning. The method (710) may comprise calculating (734) a distance from the detector(s) to the spatial registration calibration phantom as the detector(s) rotate about the phantom, and comparing (736) the calculated distance with the known reference distance. If the difference between the calculated distance values and the reference distance values are within an error tolerance, the method (710) may comprise generating (738) a notification that the imaging system has a PASS status. If the difference is outside of the error tolerance, the method may comprise generating (740) a notification that the imaging system has a FAIL status. The calibration methods described herein may be performed daily, weekly, monthly, and/or yearly according to a schedule, and/or whenever the clinician wishes to troubleshoot or test the imaging system (e.g., in response to one or more error notifications).

In some variations, any error signal may indicate that the imaging system detector needs to be replaced while in other variations, only certain errors signals may require that the detector is replaced. For example, if the notification indicates that the number of faulty pixels has exceeded the limit, then the clinician and/or technician may be instructed to replace the detector. However, if the notification indicates that a faulty sensor pixel may not be interpolated, but the number of faulty pixels has not exceeded the limit (and the number of faulty sensor pixels that cannot be interpolated has not exceeded a predetermined limit), a clinician and/or technician may decide to proceed to test whether the image data is sufficient for calculating a 3-D model and/or for monitoring patient and/or platform motion.

System Controller

The radiation therapy systems and/or patient-monitoring imaging systems described herein may each comprise a controller having a processor and one or more memories. In some variations, the radiation therapy system and the patient-monitoring imaging system(s) may share a controller, as may be desirable. A controller may comprise one or more processors and one or more machine-readable memories in communication with the one or more processors. The controller may be connected to a radiation therapy system and/or a patient-monitoring imaging system and/or other systems by wired or wireless communication channels. In some variations, the controller may be coupled to a patient platform or disposed on a trolley or medical cart adjacent to the patient and/or operator.

The controller may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks.

Examples of portable computing devices include smartphones, personal digital assistants (PDAs), cell phones, tablet PCs, phablets (personal computing devices that are larger than a smartphone, but smaller than a tablet), wearable computers taking the form of smartwatches, portable music devices, and the like.

Processor

In some embodiments, a processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), or the like. The processor may be configured to run and/or execute application processes and/or other modules, processes and/or functions associated with the system and/or a network associated therewith. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, or the like.

Memory

In some embodiments, memory may include a database and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory may store instructions to cause the processor to execute modules, processes and/or functions associated with the system, such as one or more treatment plans, imaging data acquired by one or more patient-monitoring imaging systems (e.g., during a previous treatment session and/or current treatment session, real-time imaging data), updated or adapted treatment plans, updated or adapted dose delivery instructions, radiation therapy system instructions (e.g., that may direct the operation of the gantry, therapeutic radiation source, multi-leaf collimator, and/or any other components of a radiation therapy system and/or patient-monitoring imaging system), and image and/or data processing associated with radiation delivery and/or patient-monitoring.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other embodiments described herein relate to a computer program product, which may include, for example, the instructions and/or computer code disclosed herein.

A user interface may serve as a communication interface between an operator or clinician and the radiation therapy system. The user interface may comprise an input device and output device (e.g., touch screen and display) and be configured to receive input data and output data from one or more of the support arm, external magnet, sensor, delivery device, input device, output device, network, database, and server. Sensor data from one or more sensors may be received by user interface and output visually, audibly, and/or through haptic feedback by one or more output devices. As another example, operator control of an input device (e.g., joystick, keyboard, touch screen) may be received by user and then processed by processor and memory for user interface to output a control signal to one or more support arms, external magnets, intracavity devices, and delivery devices.

Some variations of a radiation therapy system and/or patient-monitoring imaging system may comprise a display device that may allow an operator to view graphical and/or textual representations of fluence maps, and/or dose distributions, and/or regions of interest, and/or volumes of interest, and/or patient anatomical images (e.g., geometry, motion, position, location relative to radiation therapy system components), and/or patient data (e.g., physiological and/or biological), and the like. In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

Communication

In some embodiments, a radiation therapy system and/or patient-monitoring imaging system may be in communication with other computing devices via, for example, one or more networks, each of which may be any type of network (e.g., wired network, wireless network). A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some embodiments, the systems, apparatuses, and methods described herein may include a radiofrequency receiver, transmitter, and/or optical (e.g., infrared) receiver and transmitter to communicate with one or more devices and/or networks.

The invention claimed is:

1. A radiation therapy system comprising:
   a circular gantry comprising a stationary frame and a rotatable ring coupled to the stationary frame;
   a therapeutic radiation source coupled to the rotatable ring;
   an imaging system coupled to the rotatable ring, wherein the imaging system comprises a reflectometer configured to acquire image data of a patient area during rotation of the ring;
   a patient platform movable in the patient area;
   a controller in communication with the imaging system, wherein the controller is configured to process and store the acquired image data, calculate a range of motion of a patient located on the patient platform based on the acquired image data, compare the calculated range of motion with a motion envelope, and generate a notification if the calculated range of motion exceeds the motion envelope,
   wherein the motion envelope is determined based on whether the patient platform is moving or stationary, and wherein the motion envelope has a first range of motion when the patient platform is moving and has a second range of motion when the patient platform is stationary.

2. The system of claim 1, wherein the reflectometer is a time-of-flight reflectometer.

3. The system of claim 2, wherein the reflectometer image sensor is located adjacent to the therapeutic radiation source.

4. The system of claim 1, wherein the reflectometer comprises a radar sensor.

5. The system of claim 4, wherein the radar sensor comprises a terahertz sensor.

6. The system of claim 1, wherein the rotatable ring is configured to rotate at a rate of at least 10 RPM.

7. The system of claim 6, wherein the rotatable ring is configured to rotate at a rate from about 60 RPM to about 200 RPM.

8. The system of claim 1, wherein the rotatable ring defines a longitudinal bore and the imaging system is located within the bore.

9. The system of claim 8, further comprising a housing disposed over the circular gantry having a longitudinal lumen that corresponds with the bore and comprising a light-transmitting region along an inner surface of the housing that corresponds with a field-of-view of the imaging system.

10. The system of claim 9, wherein the light-transmitting region is a strip along an inner circumference of the bore.

11. The system of claim 9, wherein the light-transmitting region comprises two or more windows located along an inner circumference of the bore.

12. The system of claim 8, wherein the imaging system has a field-of-view that includes the patient area that is outside of the bore.

13. The system of claim 8, wherein the imaging system is located within the bore and has a field-of view that includes the patient area that is inside the bore.

14. The system of claim 1, wherein the controller is configured to generate a surface model of the patient at a specified time interval using images acquired during the specified time interval.

15. The system of claim 1, wherein the controller is configured to generate a 3-D model of the patient platform and to compare the generated 3-D model of the patient platform with a reference 3-D model of the patient platform to calculate a deviation from the reference 3-D model.

16. The system of claim 15, wherein the reference 3-D model of the patient platform is a 3-D model of the patient platform generated before the patient is loaded on the platform.

17. The system of claim 16, wherein the controller adjusts a position of the patient platform to compensate for the calculated deviation.

18. The system of claim 1, further comprising a display and the controller is configured to output a graphic representing the calculated range of motion to the display.

19. The system of claim 1, wherein the motion envelope is determined based on whether the therapeutic radiation source is emitting radiation, wherein the motion envelope has a first range of motion when the therapeutic radiation source is not emitting radiation and has a second range of motion when the therapeutic radiation source is emitting radiation.

20. The system of claim 19, wherein the first range of motion is greater than the second range of motion.

21. The system of claim 1, wherein the first range of motion is greater than the second range of motion.

22. The system of claim 1, wherein the controller is further configured to calculate positional information of a patient within the patient area.

23. The system of claim 22, further comprising a patient platform that is movable within the patient area, and wherein the controller is configured to:

calculate a difference between positional information of the patient at a specified time point and reference positional information of the patient; and calculate a set of patient platform adjustments that compensate for the patient positional information difference.

24. The system of claim 23, wherein the controller is further configured to move the patient platform in accordance with the calculated set of patient platform adjustments.

25. The system of claim 22, wherein the controller is configured to compare positional information of the patient and positional information of the rotatable ring and to generate a notification if an overlap is detected between patient positional information and rotatable ring positional information.

26. The system of claim 1, wherein the controller is further configured to calculate positional information of the patient platform.

27. The system of claim 1, wherein the controller is further configured to calculate positional information of a patient positioning device located in the patient area.

28. The system of claim 1, wherein the imaging system comprises a laser profiler.

29. The system of claim 1, wherein the imaging system comprises a monoscopic or stereoscopic camera.

30. The system of claim 1, further comprising a calibration phantom with predetermined dimensions and having one or more surface contour indicia with predetermined 3D geometric markings having predetermined width, height and length values.

31. The system of claim 1, wherein at least one of the patient platform, a portion of the patient area, and a calibration phantom having at least one calibration reference marking that has one or more predetermined width, and/or height, and/or length values.

32. The systm of claim 1, wherein the first range of motion is greater than the second range of motion.

33. A radiation therapy sustem comprising:
a circular gantry comprising a stationary frame and a rotatable ring coupled to the stationary frame;
a therapeutic radiation source coupled to the rotatable ring;
an imaging system coupled to the rotatable ring, wherein the imaging system comprises a reflectometer configured to acquire image data of a patient area during rotation of the ring;
a patient platform movable in the patient area;
a controller in communication with the imaging system, wherein the controller is configured to process and store the acquired image data, generate a 3-D model of a patient within the patient area at a specified time interval using images acquired during the specified time interval, compare the 3-D model of the patient at the specified time interval and a 3-D model of the patient at an earlier time interval to identify a positional difference in the 3-D models, compare the identified difference in the 3-D models with a motion envelope, and generate a notification if the identified difference exceeds the motion envelope,
wherein the motion envelope is determined based on whether the patient platform is moving or stationary, wherein the motion envelope has a first range of motion when the patient platform is moving and has a second range of motion when the patient platform is stationary.

34. The system of claim 33, wherein the controller is configured to compare the identified difference in the 3-D models with a predetermined movement threshold and to cease activation of the therapeutic radiation source if the identified difference exceeds the movement threshold.

35. The system of claim 33, wherein the controller is configured to identify surface points on the patient 3-D model and to track a position of the identified surface points over time.

36. The system of claim 33, wherein the motion envelope is determined based on whether the therapeutic radiation source is emitting radiation, wherein the motion envelope has a first range of motion when the therapeutic radiation source is not emitting radiation and has a second range of motion when the therapeutic radiation source is emitting radiation.

37. The system of claim 36, wherein the first range of motion is greater than the second range of motion.

38. The system of claim 33, wherein the first range of motion is greater than the second range of motion.

39. The system of claim 33, wherein the identified positional difference in the 3-D models corresponds with the patient's respiratory cycle.

40. The system of claim 39, wherein the controller is configured to identify the portion of the respiratory cycle with which the identified difference corresponds, and to cease activation of the therapeutic radiation source if the identified portion of the respiratory cycle does not match with a predetermined activation portion of the respiratory cycle.

* * * * *